(12) United States Patent
Hauser et al.

(10) Patent No.: US 10,179,194 B2
(45) Date of Patent: Jan. 15, 2019

(54) SELF-ASSEMBLING PEPTIDES, PEPTIDOMIMETICS AND PEPTIDIC CONJUGATES AS BUILDING BLOCKS FOR BIOFABRICATION AND PRINTING

(71) Applicant: Agency for Science, Technology and Research, Singapore (SG)

(72) Inventors: Charlotte Hauser, Singapore (SG); Yihua Loo, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 15/039,952

(22) PCT Filed: Dec. 1, 2014

(86) PCT No.: PCT/SG2014/000569
§ 371 (c)(1),
(2) Date: May 27, 2016

(87) PCT Pub. No.: WO2015/080671
PCT Pub. Date: Jun. 4, 2015

(65) Prior Publication Data
US 2016/0375177 A1    Dec. 29, 2016

(30) Foreign Application Priority Data
Nov. 30, 2013   (SG) .................................. 201308891

(51) Int. Cl.
| | |
|---|---|
| *A61K 38/00* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |
| *A61L 27/52* | (2006.01) |
| *A61K 38/06* | (2006.01) |
| *A61K 38/07* | (2006.01) |
| *A61K 38/08* | (2006.01) |
| *C07K 5/062* | (2006.01) |
| *C07K 5/083* | (2006.01) |
| *C07K 5/103* | (2006.01) |
| *C07K 7/06* | (2006.01) |
| *A61L 27/38* | (2006.01) |
| *A61L 27/50* | (2006.01) |
| *A61L 27/54* | (2006.01) |
| *B33Y 10/00* | (2015.01) |

(52) U.S. Cl.
CPC .............. *A61L 27/52* (2013.01); *A61K 38/06* (2013.01); *A61K 38/07* (2013.01); *A61K 38/08* (2013.01); *A61L 27/3834* (2013.01); *A61L 27/50* (2013.01); *A61L 27/54* (2013.01); *C07K 5/06034* (2013.01); *C07K 5/06052* (2013.01); *C07K 5/0808* (2013.01); *C07K 5/101* (2013.01); *C07K 5/1005* (2013.01); *C07K 7/06* (2013.01); *A61L 2400/06* (2013.01); *A61L 2430/34* (2013.01); *B33Y 10/00* (2014.12); *Y02A 50/385* (2018.01); *Y02A 50/411* (2018.01)

(58) Field of Classification Search
None
See application file for complete search history.

(56) References Cited

U.S. PATENT DOCUMENTS

| | | | | |
|---|---|---|---|---|
| 9,067,084 | B2* | 6/2015 | Hauser | A61K 8/042 |
| 9,120,841 | B2* | 9/2015 | Hauser | C07K 5/101 |
| 2003/0175410 | A1 | 9/2003 | Campbell et al. | |
| 2009/0117087 | A1 | 5/2009 | Carroll et al. | |
| 2013/0023460 | A1* | 1/2013 | Hauser | A61K 8/042 |
| | | | | 514/1.1 |
| 2013/0267455 | A1* | 10/2013 | Hauser | A61K 47/42 |
| | | | | 514/1.1 |
| 2014/0093473 | A1* | 4/2014 | Hauser | C07K 5/101 |
| | | | | 424/78.17 |
| 2014/0349933 | A1* | 11/2014 | Hauser | A61K 31/7088 |
| | | | | 514/9.1 |

(Continued)

FOREIGN PATENT DOCUMENTS

| | | |
|---|---|---|
| SG | 11201604238 | 6/2016 |
| WO | WO 2011/123061 A1 | 10/2011 |

(Continued)

OTHER PUBLICATIONS

Mishra et al. "Ultrasmall natural peptides self-assemble to strong temperature-resistant helical fibers in scaffolds suitable for tissue engineering" Nano Today 6:232-239. (Year: 2011).*

(Continued)

*Primary Examiner* — Zachary J Miknis

(74) *Attorney, Agent, or Firm* — Wolf, Greenfield & Sacks, P.C.

(57) ABSTRACT

The present invention relates to the use of peptides, peptoids and/or peptidomimetics capable of self-assembling and forming a (nanofibrous) hydrogel in biofabrication. The present invention further relates to methods for preparing hydrogels and to methods for preparing continuous fibres and to methods for obtaining multi-cellular constructs with defined, precise geometrics. The present invention further relates to various uses of such hydrogels for obtaining mini-hydrogel arrays and 3D organoid structures or 3D macromolecular biological constructs.

29 Claims, 18 Drawing Sheets
Specification includes a Sequence Listing.

(56) References Cited

U.S. PATENT DOCUMENTS

| | | | | |
|---|---|---|---|---|
| 2015/0352220 A1* | 12/2015 | Reithofer | ......... | A61K 47/48246 514/492 |
| 2015/0367028 A1* | 12/2015 | Hauser | ................... | A61K 8/042 424/400 |
| 2016/0271178 A1* | 9/2016 | Hauser | .................... | A61L 15/60 |

FOREIGN PATENT DOCUMENTS

| | | | | |
|---|---|---|---|---|
| WO | WO-2011123061 A1 * | 10/2011 | ............. | A61K 8/042 |
| WO | WO 2013/004399 A1 | 1/2013 | | |
| WO | WO 2013/040078 A2 | 3/2013 | | |
| WO | WO 2013/066274 A1 | 5/2013 | | |
| WO | WO-2013066274 A1 * | 5/2013 | ......... | A61K 31/7088 |
| WO | WO 2013/124620 A1 | 8/2013 | | |
| WO | WO 2013/126017 A1 | 8/2013 | | |
| WO | WO 2014/104974 A2 | 7/2014 | | |
| WO | WO 2014/104981 A1 | 7/2014 | | |
| WO | WO 2014/116187 A1 | 7/2014 | | |
| WO | WO 2015/080670 A1 | 6/2015 | | |
| WO | WO 2015/080671 A1 | 6/2015 | | |

OTHER PUBLICATIONS

International Search Report and Written Opinion for PCT/SG2014/000569 dated Feb. 26, 2015.
International Preliminary Report on Patentability for PCT/SG2014/000569 dated Jun. 9, 2016.
Singapore Search Report and Written Opinion for SG 11201604239W dated Mar. 20, 2017.
Lakshmanan et al., Ultrasmall peptides self-assemble into diverse nanostructures: morphological evaluation and potential implications. Int J Mol Sci. 2011;12(9):5736-46. doi: 10.3390/ijms12095736. Epub Sep. 7, 2011.
Mishra et al., Ultrasmall natural peptides self-assemble to strong temperature-resistant helical fibers in scaffolds suitable for tissue engineering. Nano Today 2011;6:232-39. doi:10.1016/j.nantod.2011.05.001.
Murphy et al., Evaluation of hydrogels for bio-printing applications. J Biomed Mater Res A. Jan. 2013;101(1):272-84. doi: 10.1002/jbm.a.34326. Epub Aug. 31, 2012. Abstract Only.
Seow et al., Short to ultrashort peptide hydrogels for biomedical uses. Materials Today Oct. 2014;17(8):381-8.
Tokatlian et al., Design and characterization of microporous hyaluronic acid hydrogels for in vitro gene transfer to mMSCs. Acta Biomater. Nov. 2012;8(11):3921-31. doi: 10.1016/j.actbio.2012.07.014. Epub Jul. 20, 2012.
Wüst et al., Controlled Positioning of Cells in Biomaterials—Approaches Towards 3D Tissue Printing. J Funct Biomater. Aug. 4, 2011;2(3):119-54. doi: 10.3390/jfb2030119.
Yu et al., Promoting neuron adhesion and growth. Materials Today May 31, 2008;11(5):36-43.
Written Opinion for Singaporean Application No. 11201604239W, dated Mar. 29, 2018.
Extended European Search Report for European Application No. 14866446.9, dated Aug. 17, 2017.

* cited by examiner

Figure 2

Subclass with acidic amino acids as polar head group
- Stimuli-responsive gelation at low pH
- Amidation or esterification removes sensitivity to pH, but hydrogels can still be obtained

Subclass with amidated basic amino acids as polar head group
- Stimuli-responsive gelation in the presence of salts at physiological concentrations (0.9% saline and PBS)

Minimum gelation concentration

| Peptide | SEQ ID NO | Water | PBS |
|---|---|---|---|
| Ac-IK3-NH$_2$ | | >30 | 10 |
| Ac-IK6-NH$_2$ | 21 | 10 | 3 |
| Ac-LK6-NH$_2$ | 20 | 15 | 6 |

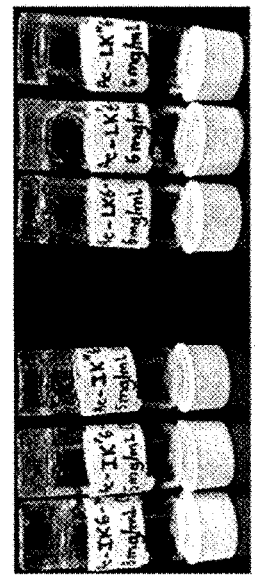

Substitutions with synthetic amino acids
- Sequence of aliphatic amino acid residues influences gelation:

Minimum gelation concentration of hexamers in PBS

| Head group | I-Series | | L-Series | |
|---|---|---|---|---|
| L-Lysine | 3 | (SEQ ID NO 21) | 6 | (SEQ ID NO. 20) |
| L-Ornithine | 5 | (SEQ ID NO 32) | 6 | (SEQ ID NO 31) |
| 2,4-Diaminobutyric acid | 5 | (SEQ ID NO 35) | 6 | (SEQ ID NO 34) |

Figure 10
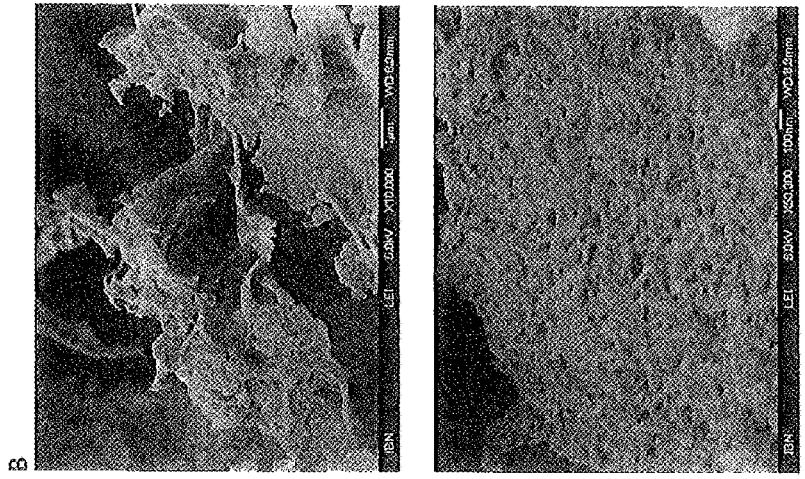
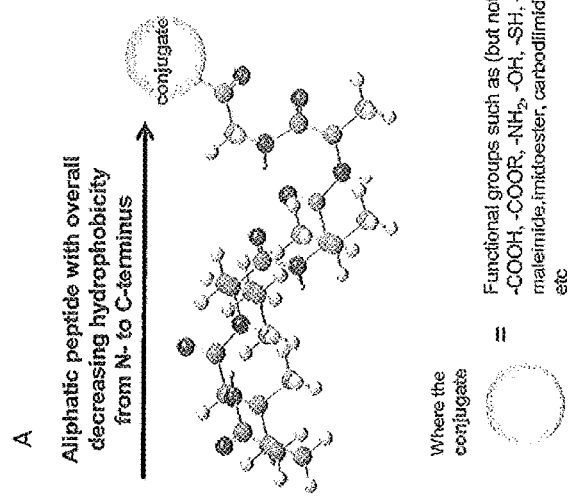

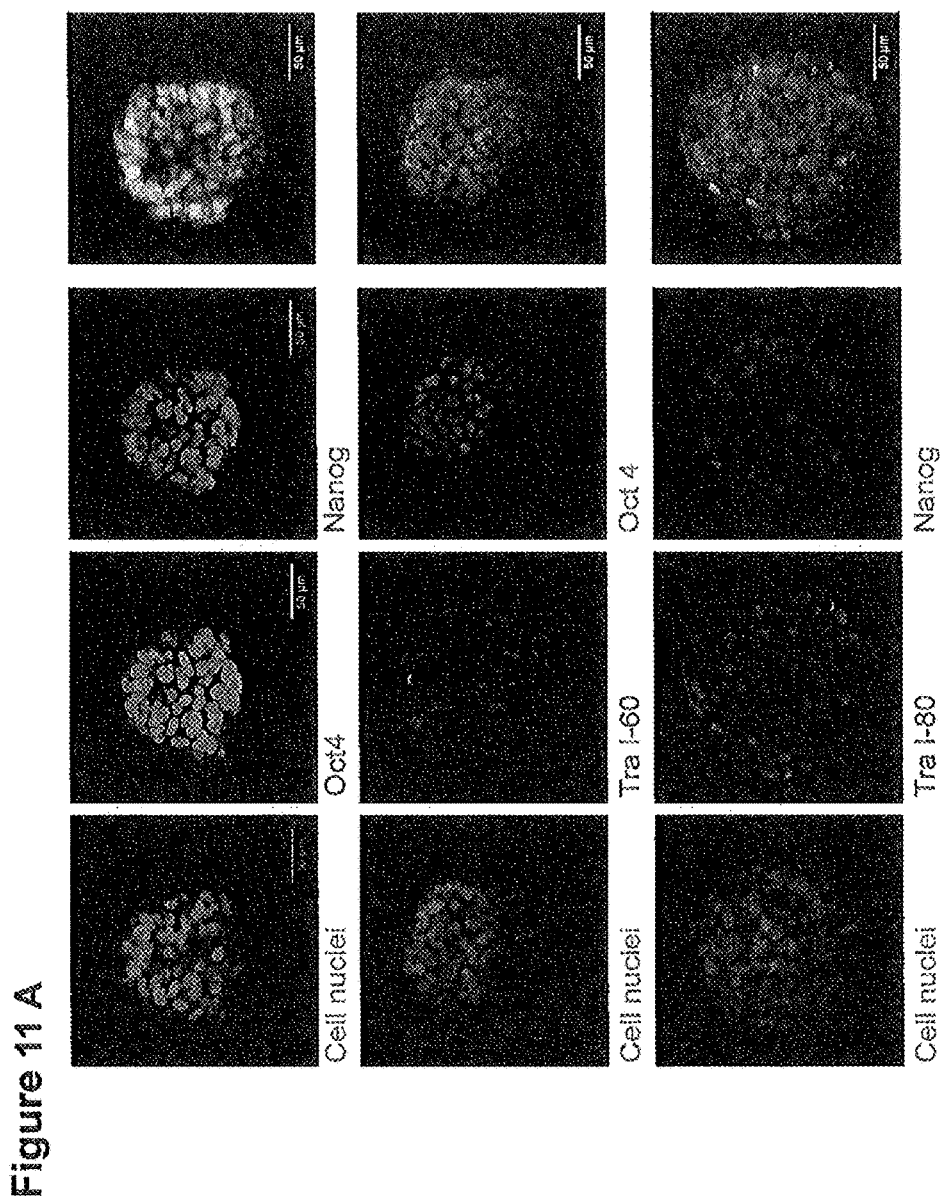

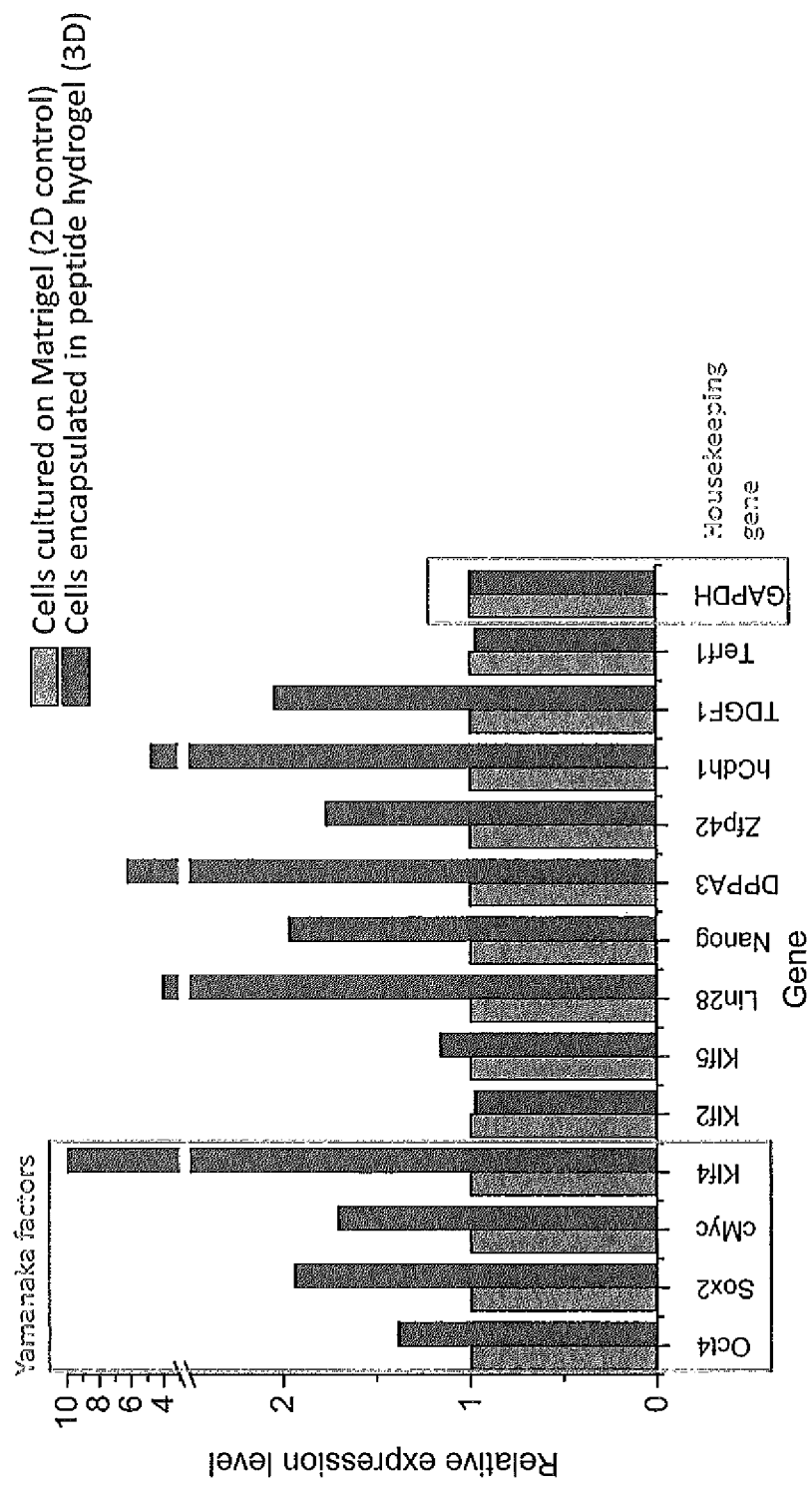

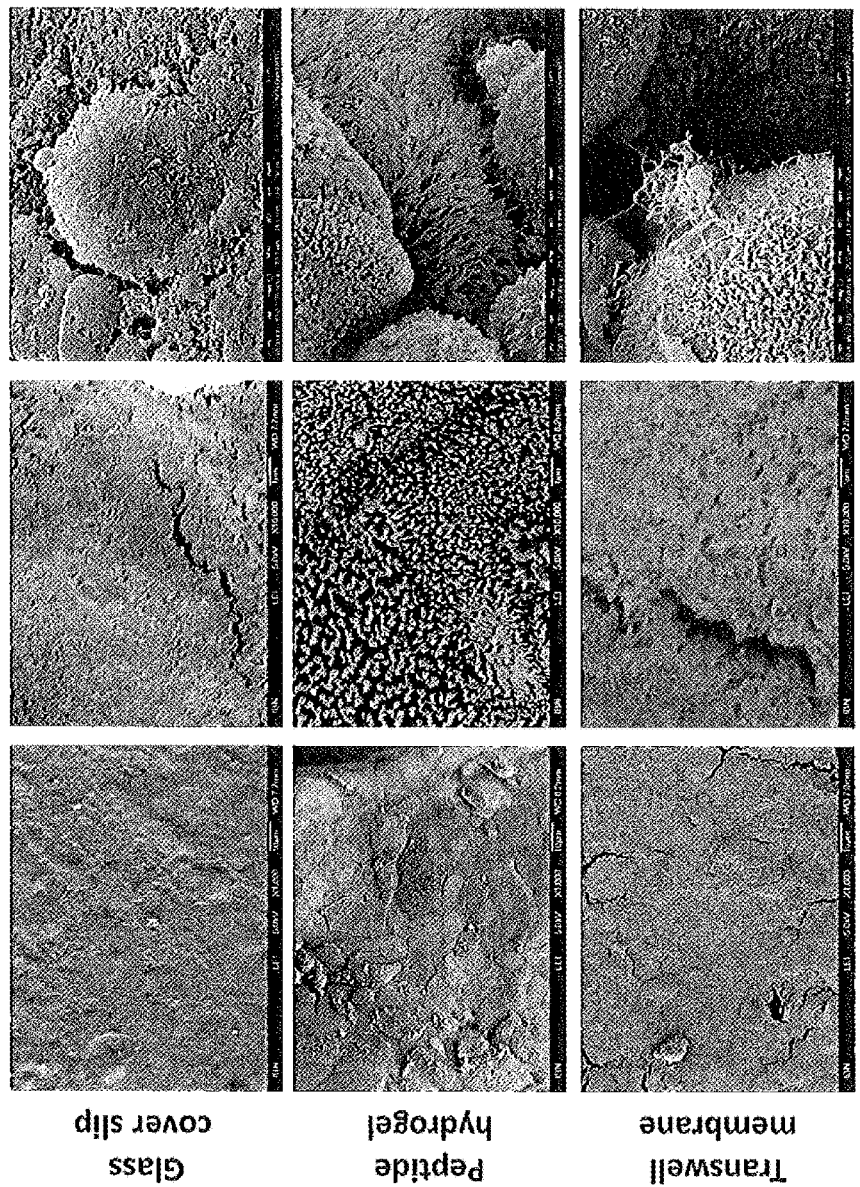

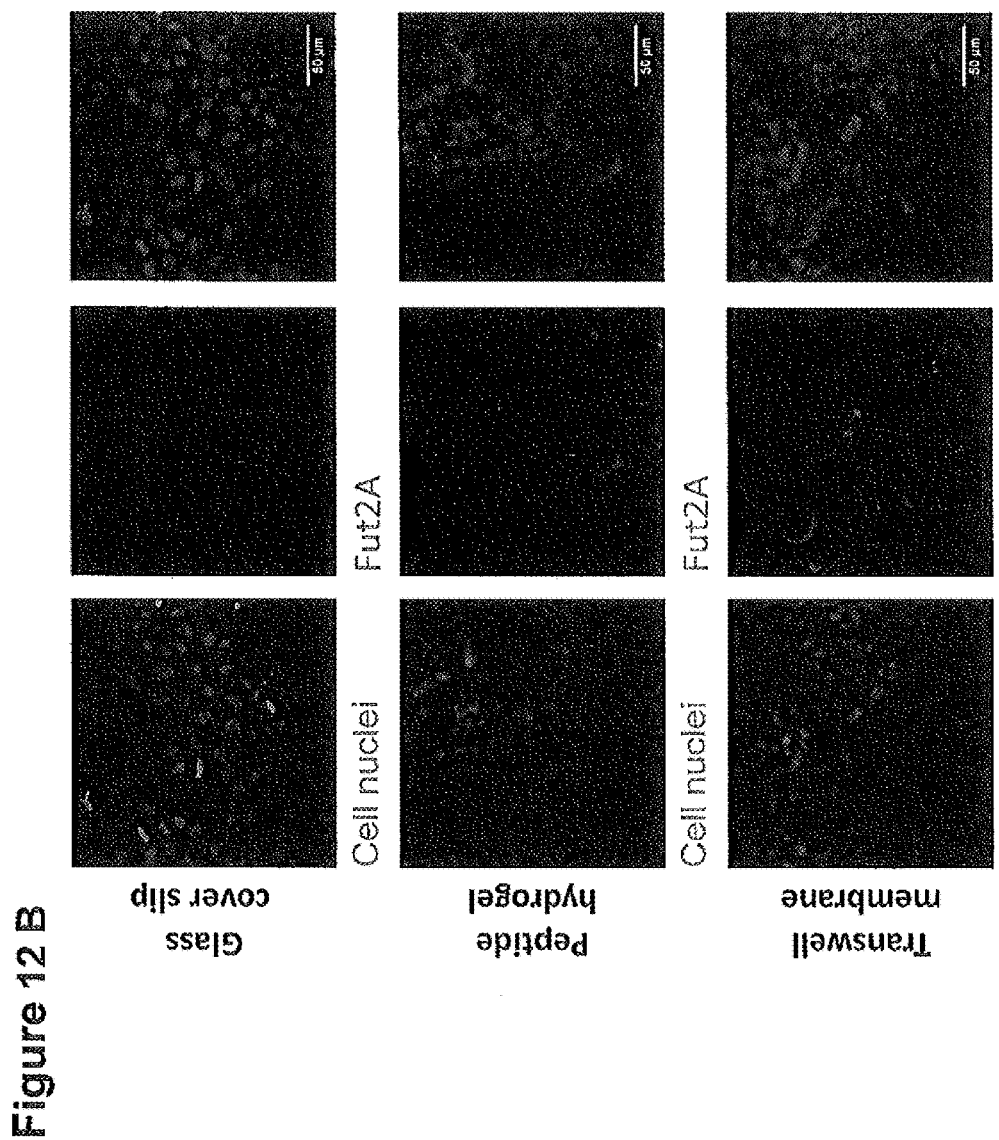

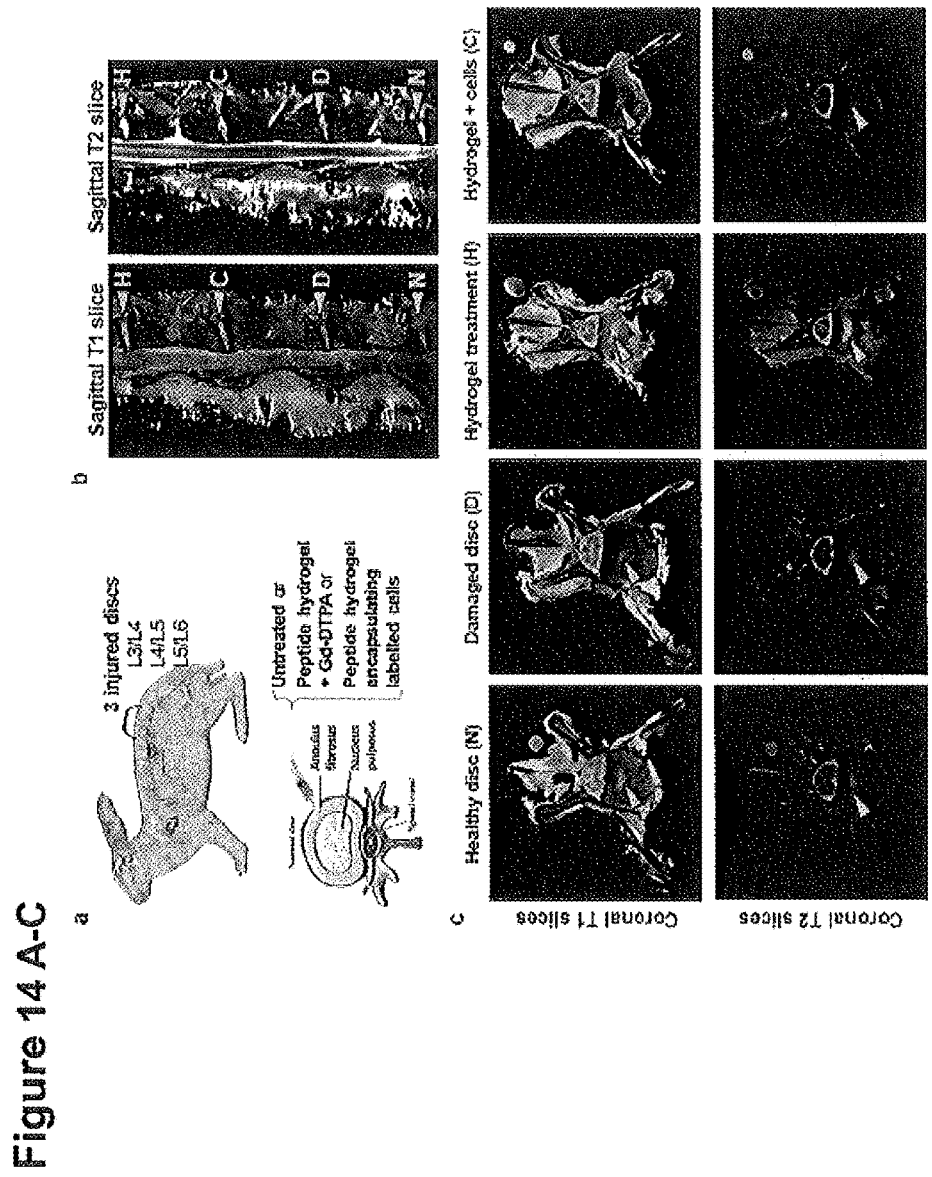
Figure 14 A-C

```
                        SEQUENCE LISTING

<160> NUMBER OF SEQ ID NOS: 55

<210> SEQ ID NO 1
<211> LENGTH: 5
<212> TYPE: PRT
<213> ORGANISM: Artificial Sequence
<220> FEATURE:
<223> OTHER INFORMATION: aliphatic sequence

<400> SEQUENCE: 1

Leu Ile Val Ala Gly
1               5

<210> SEQ ID NO 2
<211> LENGTH: 5
<212> TYPE: PRT
<213> ORGANISM: Artificial Sequence
<220> FEATURE:
<223> OTHER INFORMATION: aliphatic sequence

<400> SEQUENCE: 2

Ile Leu Val Ala Gly
1               5

<210> SEQ ID NO 3
<211> LENGTH: 5
<212> TYPE: PRT
<213> ORGANISM: Artificial Sequence
<220> FEATURE:
<223> OTHER INFORMATION: aliphatic sequence

<400> SEQUENCE: 3

Leu Ile Val Ala Ala
1               5

<210> SEQ ID NO 4
<211> LENGTH: 5
<212> TYPE: PRT
<213> ORGANISM: Artificial Sequence
<220> FEATURE:
<223> OTHER INFORMATION: aliphatic sequence

<400> SEQUENCE: 4

Leu Ala Val Ala Gly
1               5
```

```
<210> SEQ ID NO 5
<211> LENGTH: 5
<212> TYPE: PRT
<213> ORGANISM: Artificial Sequence
<220> FEATURE:
<223> OTHER INFORMATION: aliphatic sequence

<400> SEQUENCE: 5

Ala Ile Val Ala Gly
1               5

<210> SEQ ID NO 6
<211> LENGTH: 5
<212> TYPE: PRT
<213> ORGANISM: Artificial Sequence
<220> FEATURE:
<223> OTHER INFORMATION: aliphatic sequence

<400> SEQUENCE: 6

Gly Ile Val Ala Gly
1               5

<210> SEQ ID NO 7
<211> LENGTH: 5
<212> TYPE: PRT
<213> ORGANISM: Artificial Sequence
<220> FEATURE:
<223> OTHER INFORMATION: aliphatic sequence

<400> SEQUENCE: 7

Val Ile Val Ala Gly
1               5

<210> SEQ ID NO 8
<211> LENGTH: 5
<212> TYPE: PRT
<213> ORGANISM: Artificial Sequence
<220> FEATURE:
<223> OTHER INFORMATION: aliphatic sequence

<400> SEQUENCE: 8

Ala Leu Val Ala Gly
1               5

<210> SEQ ID NO 9
<211> LENGTH: 5
<212> TYPE: PRT
<213> ORGANISM: Artificial Sequence
<220> FEATURE:
<223> OTHER INFORMATION: aliphatic sequence

<400> SEQUENCE: 9

Gly Leu Val Ala Gly
1               5

<210> SEQ ID NO 10
<211> LENGTH: 5
<212> TYPE: PRT
<213> ORGANISM: Artificial Sequence
<220> FEATURE:
<223> OTHER INFORMATION: aliphatic sequence

<400> SEQUENCE: 10

Val Leu Val Ala Gly
1               5
```

```
<210> SEQ ID NO 11
<211> LENGTH: 4
<212> TYPE: PRT
<213> ORGANISM: Artificial Sequence
<220> FEATURE:
<223> OTHER INFORMATION: aliphatic sequence

<400> SEQUENCE: 11

Ile Val Ala Gly
1

<210> SEQ ID NO 12
<211> LENGTH: 4
<212> TYPE: PRT
<213> ORGANISM: Artificial Sequence
<220> FEATURE:
<223> OTHER INFORMATION: aliphatic sequence

<400> SEQUENCE: 12

Leu Ile Val Ala
1

<210> SEQ ID NO 13
<211> LENGTH: 4
<212> TYPE: PRT
<213> ORGANISM: Artificial Sequence
<220> FEATURE:
<223> OTHER INFORMATION: aliphatic sequence

<400> SEQUENCE: 13

Leu Ile Val Gly
1

<210> SEQ ID NO 14
<211> LENGTH: 6
<212> TYPE: PRT
<213> ORGANISM: Artificial Sequence
<220> FEATURE:
<223> OTHER INFORMATION: amphiphilic sequence

<400> SEQUENCE: 14

Leu Ile Val Ala Gly Asp
1               5

<210> SEQ ID NO 15
<211> LENGTH: 6
<212> TYPE: PRT
<213> ORGANISM: Artificial Sequence
<220> FEATURE:
<223> OTHER INFORMATION: amphiphilic sequence

<400> SEQUENCE: 15

Ile Leu Val Ala Gly Asp
1               5

<210> SEQ ID NO 16
<211> LENGTH: 6
<212> TYPE: PRT
<213> ORGANISM: Artificial Sequence
<220> FEATURE:
<223> OTHER INFORMATION: amphiphilic sequence

<400> SEQUENCE: 16

Leu Ile Val Ala Ala Asp
1               5

<210> SEQ ID NO 17
```

```
<211> LENGTH: 6
<212> TYPE: PRT
<213> ORGANISM: Artificial Sequence
<220> FEATURE:
<223> OTHER INFORMATION: amphiphilic sequence

<400> SEQUENCE: 17

Leu Ala Val Ala Gly Asp
1               5

<210> SEQ ID NO 18
<211> LENGTH: 6
<212> TYPE: PRT
<213> ORGANISM: Artificial Sequence
<220> FEATURE:
<223> OTHER INFORMATION: amphiphilic sequence

<400> SEQUENCE: 18

Ala Ile Val Ala Gly Asp
1               5

<210> SEQ ID NO 19
<211> LENGTH: 6
<212> TYPE: PRT
<213> ORGANISM: Artificial Sequence
<220> FEATURE:
<223> OTHER INFORMATION: amphiphilic sequence

<400> SEQUENCE: 19

Leu Ile Val Ala Gly Glu
1               5

<210> SEQ ID NO 20
<211> LENGTH: 6
<212> TYPE: PRT
<213> ORGANISM: Artificial Sequence
<220> FEATURE:
<223> OTHER INFORMATION: amphiphilic sequence

<400> SEQUENCE: 20

Leu Ile Val Ala Gly Lys
1               5

<210> SEQ ID NO 21
<211> LENGTH: 6
<212> TYPE: PRT
<213> ORGANISM: Artificial Sequence
<220> FEATURE:
<223> OTHER INFORMATION: amphiphilic sequence

<400> SEQUENCE: 21

Ile Leu Val Ala Gly Lys
1               5

<210> SEQ ID NO 22
<211> LENGTH: 6
<212> TYPE: PRT
<213> ORGANISM: Artificial Sequence
<220> FEATURE:
<223> OTHER INFORMATION: amphiphilic sequence

<400> SEQUENCE: 22

Leu Ile Val Ala Gly Thr
1               5

<210> SEQ ID NO 23
<211> LENGTH: 6
```

```
<212> TYPE: PRT
<213> ORGANISM: Artificial Sequence
<220> FEATURE:
<223> OTHER INFORMATION: amphiphilic sequence

<400> SEQUENCE: 23

Ala Ile Val Ala Gly Thr
1               5

<210> SEQ ID NO 24
<211> LENGTH: 6
<212> TYPE: PRT
<213> ORGANISM: Artificial Sequence
<220> FEATURE:
<223> OTHER INFORMATION: amphiphilic sequence

<400> SEQUENCE: 24

Ala Ile Val Ala Gly Lys
1               5

<210> SEQ ID NO 25
<211> LENGTH: 5
<212> TYPE: PRT
<213> ORGANISM: Artificial Sequence
<220> FEATURE:
<223> OTHER INFORMATION: amphiphilic sequence

<400> SEQUENCE: 25

Leu Ile Val Ala Asp
1               5

<210> SEQ ID NO 26
<211> LENGTH: 5
<212> TYPE: PRT
<213> ORGANISM: Artificial Sequence
<220> FEATURE:
<223> OTHER INFORMATION: amphiphilic sequence

<400> SEQUENCE: 26

Leu Ile Val Gly Asp
1               5

<210> SEQ ID NO 27
<211> LENGTH: 4
<212> TYPE: PRT
<213> ORGANISM: Artificial Sequence
<220> FEATURE:
<223> OTHER INFORMATION: amphiphilic sequence

<400> SEQUENCE: 27

Ile Val Ala Asp
1

<210> SEQ ID NO 28
<211> LENGTH: 4
<212> TYPE: PRT
<213> ORGANISM: Artificial Sequence
<220> FEATURE:
<223> OTHER INFORMATION: amphiphilic sequence

<400> SEQUENCE: 28

Ile Val Ala Lys
1

<210> SEQ ID NO 29
<211> LENGTH: 4
<212> TYPE: PRT
```

```
<213> ORGANISM: Artificial Sequence
<220> FEATURE:
<223> OTHER INFORMATION: amphiphilic sequence

<400> SEQUENCE: 29

Ile Ile Ile Asp
1

<210> SEQ ID NO 30
<211> LENGTH: 4
<212> TYPE: PRT
<213> ORGANISM: Artificial Sequence
<220> FEATURE:
<223> OTHER INFORMATION: amphiphilic sequence

<400> SEQUENCE: 30

Ile Ile Ile Lys
1

<210> SEQ ID NO 31
<211> LENGTH: 5
<212> TYPE: PRT
<213> ORGANISM: Artificial Sequence
<220> FEATURE:
<223> OTHER INFORMATION: amphiphilic sequence with X = Orn
<220> FEATURE:
<221> NAME/KEY: misc_feature
<222> LOCATION: (5)..(5)
<223> OTHER INFORMATION: Xaa can be any naturally occurring amino acid

<400> SEQUENCE: 31

Leu Ile Val Ala Xaa
1               5

<210> SEQ ID NO 32
<211> LENGTH: 6
<212> TYPE: PRT
<213> ORGANISM: Artificial Sequence
<220> FEATURE:
<223> OTHER INFORMATION: amphiphilic sequence with X = Orn
<220> FEATURE:
<221> NAME/KEY: misc_feature
<222> LOCATION: (6)..(6)
<223> OTHER INFORMATION: Xaa can be any naturally occurring amino acid

<400> SEQUENCE: 32

Ile Leu Val Ala Gly Xaa
1               5

<210> SEQ ID NO 33
<211> LENGTH: 6
<212> TYPE: PRT
<213> ORGANISM: Artificial Sequence
<220> FEATURE:
<223> OTHER INFORMATION: amphiphilic sequence with X = Orn
<220> FEATURE:
<221> NAME/KEY: misc_feature
<222> LOCATION: (6)..(6)
<223> OTHER INFORMATION: Xaa can be any naturally occurring amino acid

<400> SEQUENCE: 33

Ala Ile Val Ala Gly Xaa
1               5

<210> SEQ ID NO 34
<211> LENGTH: 6
<212> TYPE: PRT
<213> ORGANISM: Artificial Sequence
<220> FEATURE:
```

```
<223> OTHER INFORMATION: amphiphilic sequence with X = Dab
<220> FEATURE:
<221> NAME/KEY: misc_feature
<222> LOCATION: (6)..(6)
<223> OTHER INFORMATION: Xaa can be any naturally occurring amino acid

<400> SEQUENCE: 34

Leu Ile Val Ala Gly Xaa
1               5

<210> SEQ ID NO 35
<211> LENGTH: 6
<212> TYPE: PRT
<213> ORGANISM: Artificial Sequence
<220> FEATURE:
<223> OTHER INFORMATION: amphiphilic sequence with X = Dab
<220> FEATURE:
<221> NAME/KEY: misc_feature
<222> LOCATION: (6)..(6)
<223> OTHER INFORMATION: Xaa can be any naturally occurring amino acid

<400> SEQUENCE: 35

Ile Leu Val Ala Gly Xaa
1               5

<210> SEQ ID NO 36
<211> LENGTH: 6
<212> TYPE: PRT
<213> ORGANISM: Artificial Sequence
<220> FEATURE:
<223> OTHER INFORMATION: amphiphilic sequence with X = Dab
<220> FEATURE:
<221> NAME/KEY: misc_feature
<222> LOCATION: (6)..(6)
<223> OTHER INFORMATION: Xaa can be any naturally occurring amino acid

<400> SEQUENCE: 36

Ala Ile Val Ala Gly Xaa
1               5

<210> SEQ ID NO 37
<211> LENGTH: 6
<212> TYPE: PRT
<213> ORGANISM: Artificial Sequence
<220> FEATURE:
<223> OTHER INFORMATION: amphiphilic sequence with X = Dap
<220> FEATURE:
<221> NAME/KEY: misc_feature
<222> LOCATION: (6)..(6)
<223> OTHER INFORMATION: Xaa can be any naturally occurring amino acid

<400> SEQUENCE: 37

Leu Ile Val Ala Gly Xaa
1               5

<210> SEQ ID NO 38
<211> LENGTH: 6
<212> TYPE: PRT
<213> ORGANISM: Artificial Sequence
<220> FEATURE:
<223> OTHER INFORMATION: amphiphilic sequence with X = Dap
<220> FEATURE:
<221> NAME/KEY: misc_feature
<222> LOCATION: (6)..(6)
<223> OTHER INFORMATION: Xaa can be any naturally occurring amino acid

<400> SEQUENCE: 38

Ile Leu Val Ala Gly Xaa
1               5
```

```
<210> SEQ ID NO 39
<211> LENGTH: 6
<212> TYPE: PRT
<213> ORGANISM: Artificial Sequence
<220> FEATURE:
<223> OTHER INFORMATION: amphiphilic sequence with X = Dap
<220> FEATURE:
<221> NAME/KEY: misc_feature
<222> LOCATION: (6)..(6)
<223> OTHER INFORMATION: Xaa can be any naturally occurring amino acid

<400> SEQUENCE: 39

Ala Ile Val Ala Gly Xaa
1               5

<210> SEQ ID NO 40
<211> LENGTH: 7
<212> TYPE: PRT
<213> ORGANISM: Artificial Sequence
<220> FEATURE:
<223> OTHER INFORMATION: amphiphilic sequence

<400> SEQUENCE: 40

Leu Ile Val Ala Gly Asp Asp
1               5

<210> SEQ ID NO 41
<211> LENGTH: 7
<212> TYPE: PRT
<213> ORGANISM: Artificial Sequence
<220> FEATURE:
<223> OTHER INFORMATION: amphiphilic sequence

<400> SEQUENCE: 41

Leu Ile Val Ala Gly Glu Glu
1               5

<210> SEQ ID NO 42
<211> LENGTH: 7
<212> TYPE: PRT
<213> ORGANISM: Artificial Sequence
<220> FEATURE:
<223> OTHER INFORMATION: amphiphilic sequence

<400> SEQUENCE: 42

Leu Ile Val Ala Gly Lys Cys
1               5

<210> SEQ ID NO 43
<211> LENGTH: 6
<212> TYPE: PRT
<213> ORGANISM: Artificial Sequence
<220> FEATURE:
<223> OTHER INFORMATION: amphiphilic sequence

<400> SEQUENCE: 43

Leu Ile Val Ala Gly Ser
1               5

<210> SEQ ID NO 44
<211> LENGTH: 6
<212> TYPE: PRT
<213> ORGANISM: Artificial Sequence
<220> FEATURE:
<223> OTHER INFORMATION: amphiphilic sequence

<400> SEQUENCE: 44
```

Ile Leu Val Ala Gly Ser
1               5

<210> SEQ ID NO 45
<211> LENGTH: 6
<212> TYPE: PRT
<213> ORGANISM: Artificial Sequence
<220> FEATURE:
<223> OTHER INFORMATION: amphiphilic sequence

<400> SEQUENCE: 45

Ala Ile Val Ala Gly Ser
1               5

<210> SEQ ID NO 46
<211> LENGTH: 6
<212> TYPE: PRT
<213> ORGANISM: Artificial Sequence
<220> FEATURE:
<223> OTHER INFORMATION: amphiphilic sequence

<400> SEQUENCE: 46

Ile Leu Val Ala Gly Thr
1               5

<210> SEQ ID NO 47
<211> LENGTH: 4
<212> TYPE: PRT
<213> ORGANISM: Artificial Sequence
<220> FEATURE:
<223> OTHER INFORMATION: amphiphilic sequence

<400> SEQUENCE: 47

Leu Leu Leu Leu
1

<210> SEQ ID NO 48
<211> LENGTH: 4
<212> TYPE: PRT
<213> ORGANISM: Artificial Sequence
<220> FEATURE:
<223> OTHER INFORMATION: amphiphilic sequence

<400> SEQUENCE: 48

Ile Ile Ile Ile
1

<210> SEQ ID NO 49
<211> LENGTH: 4
<212> TYPE: PRT
<213> ORGANISM: Artificial Sequence
<220> FEATURE:
<223> OTHER INFORMATION: amphiphilic sequence

<400> SEQUENCE: 49

Val Val Val Val
1

<210> SEQ ID NO 50
<211> LENGTH: 4
<212> TYPE: PRT
<213> ORGANISM: Artificial Sequence
<220> FEATURE:
<223> OTHER INFORMATION: amphiphilic sequence

<400> SEQUENCE: 50

Ala Ala Ala Ala

```
<210> SEQ ID NO 51
<211> LENGTH: 4
<212> TYPE: PRT
<213> ORGANISM: Artificial Sequence
<220> FEATURE:
<223> OTHER INFORMATION: amphiphilic sequence

<400> SEQUENCE: 51

Gly Gly Gly Gly
1

<210> SEQ ID NO 52
<211> LENGTH: 10
<212> TYPE: PRT
<213> ORGANISM: Artificial Sequence
<220> FEATURE:
<223> OTHER INFORMATION: leader sequence of T7 bacteriophage gene 10

<400> SEQUENCE: 52

Ala Ser Met Thr Gly Gly Gln Gln Met Gly
1               5                   10

<210> SEQ ID NO 53
<211> LENGTH: 11
<212> TYPE: PRT
<213> ORGANISM: herpes simplex
<220> FEATURE:
<223> OTHER INFORMATION:

<400> SEQUENCE: 53

Gln Pro Glu Leu Ala Pro Glu Asp Pro Glu Asp
1               5                   10

<210> SEQ ID NO 54
<211> LENGTH: 9
<212> TYPE: PRT
<213> ORGANISM: Artificial Sequence
<220> FEATURE:
<223> OTHER INFORMATION: hemagglutinin (HA) epitope

<400> SEQUENCE: 54

Tyr Pro Tyr Asp Val Pro Asp Tyr Ala
1               5

<210> SEQ ID NO 55
<211> LENGTH: 10
<212> TYPE: PRT
<213> ORGANISM: Artificial Sequence
<220> FEATURE:
<223> OTHER INFORMATION: epitope of the transcription factor c-myc

<400> SEQUENCE: 55

Glu Gln Lys Leu Ile Ser Glu Glu Asp Leu
1               5                   10
```

SELF-ASSEMBLING PEPTIDES, PEPTIDOMIMETICS AND PEPTIDIC CONJUGATES AS BUILDING BLOCKS FOR BIOFABRICATION AND PRINTING

RELATED APPLICATIONS

This application is a national stage filing under 35 U.S.C. § 371 of international application number PCT/SG2014/000569, filed Dec. 1, 2014, which claims the benefit of priority of Singapore provisional application No. 201308891-9, filed Nov. 30, 2013, the contents of each of which are hereby incorporated by reference in their entirety for all purposes.

FIELD OF THE INVENTION

The present invention relates to the use of peptides, peptoids and/or peptidomimetics capable of self-assembling and forming a (nanofibrous) hydrogel in biofabrication. The present invention further relates to methods for preparing hydrogels and to methods for preparing continuous fibres and to methods for obtaining multi-cellular constructs with defined, precise geometries. The present invention further relates to various uses of such hydrogels for obtaining mini-hydrogel arrays and 3D organoid structures or 3D macromolecular biological constructs.

BACKGROUND OF THE INVENTION

Self-assembly is an elegant and expedient "bottom-up" approach towards designing ordered, three-dimensional and biocompatible nanobiomaterials. Reproducible macromolecular nanostructures can be obtained due to the highly specific interactions between the building blocks. These intermolecular associations organize the supramolecular architecture and are mainly non-covalent electrostatic interactions, hydrogen bonds, van der Waals forces, etc. Supramolecular chemistry or biology gathers a vast body of two or three dimensional complex structures and entities formed by association of chemical or biological species. These associations are governed by the principles of molecular complementarity or molecular recognition and self-assembly. The knowledge of the rules of intermolecular association can be used to design polymolecular assemblies in form of membranes, films, layers, micelles, tubules, gels for a variety of biomedical or technological applications (J.-M. Lehn, Science, 295, 2400-2403, 2002).

Peptides are versatile building blocks for fabricating supramolecular architectures. Their ability to adopt specific secondary structures, as prescribed by amino acid sequence, provides a unique platform for the design of self-assembling biomaterials with hierarchical three-dimensional (3D) macromolecular architectures, nanoscale features and tunable physical properties (S. Zhang, Nature Biotechnology, 21, 1171-1178, 2003). Peptides are for instance able to assemble into nanotubes (U.S. Pat. No. 7,179,784) or into supramolecular hydrogels consisting of three dimensional scaffolds with a large amount of around 98-99% immobilized water or aqueous solution. The peptide-based biomaterials are powerful tools for potential applications in biotechnology, medicine and even technical applications. Depending on the individual properties these peptide-based hydrogels are thought to serve in the development of new materials for tissue engineering, regenerative medicine, as drug and vaccine delivery vehicles or as peptide chips for pharmaceutical research and diagnosis (E. Place et al., Nature Materials, 8, 457-470, 2009). There is also a strong interest to use peptide-based self-assembled biomaterial such as gels for the development of molecular electronic devices (A. R. Hirst et al. Angew. Chem. Int. Ed., 47, 8002-8018, 2008).

A variety of "smart peptide hydrogels" have been generated that react on external manipulations such as temperature, pH, mechanical influences or other stimuli with a dynamic behavior of swelling, shrinking or decomposing. Nevertheless, these biomaterials are still not "advanced" enough to mimic the biological variability of natural tissues as for example the extracellular matrix (ECM) or cartilage tissue or others. The challenge for a meaningful use of peptide hydrogels is to mimic the replacing natural tissues not only as "space filler" or mechanical scaffold, but to understand and cope with the biochemical signals and physiological requirements that keep the containing cells in the right place and under "in vivo" conditions (R. Fairman and K. Akerfeldt, Current Opinion in Structural Biology, 15, 453-463, 2005).

Much effort has been undertaken to understand and control the relationship between peptide sequence and structure for a rational design of suitable hydrogels. In general hydrogels contain macroscopic structures such as fibers that entangle and form meshes. Most of the peptide-based hydrogels utilize β-pleated sheets which assemble to fibers as building blocks (S. Zhang et al., PNAS, 90, 3334-3338, 1993: A. Aggeli et al., Nature, 386, 259-262, 1997, etc.). It is also possible to obtain self-assembled hydrogels from α-helical peptides besides β-sheet structure-based materials (W. A. Petka et al., Science, 281, 389-392, 1998; C. Wang et al., Nature, 397, 417-420, 1999; C. Gribbon et al., Biochemistry, 47, 10365-10371, 2008; E. Banwell et al., Nature Materials, 8, 596-600, 2009, etc.).

Nevertheless, the currently known peptide hydrogels are in most of the cases associated with low rigidity, sometimes unfavourable physiological properties and/or complexity and the requirement of substantial processing thereof which leads to high production costs. There is therefore a widely recognized need for peptide hydrogels that are easily formed, non-toxic and have a sufficiently high rigidity for standard applications. The hydrogels should also be suitable for the delivery of bioactive moieties (such as nucleic acids, small molecule therapeutics, cosmetic and anti-microbial agents) and/or for use as biomimetic scaffolds that support the in vivo and in vitro growth of cells and facilitate the regeneration of native tissue and/or for use in 2D and/or 3D biofabrication.

"Biofabrication" utilizes techniques such as additive manufacturing (i.e. printing) and moulding to create 2D and 3D structures from biomaterial building blocks. During the fabrication process, bioactive moieties and cells can be incorporated in a precise fashion. In the specific example of "bio-printing", a computer-aided device is used to precisely deposit the biomaterial building block (ink), using a layer-by-layer approach, into the pre-determined, prescribed 3D geometry. The size of these structures range from the micro-scale to larger structures. Additives such as growth factors, cytokines, vitamins, minerals, oligonucleotides, small molecule drugs, and other bioactive moieties, and various cell types can also be accurately deposited concurrently or subsequently. Bio-inert components can be utilized as supports or fillers to create open inner spaces to mimic biological tissue. Such biological constructs can be subsequently implanted or used to investigate the interactions between cells and/or biomaterials, as well as to develop 3D disease models. In the specific example of "moulding", the biomaterial building block is deposited into a template of specific shape and dimensions, together with relevant bioactive moieties and cells (Malda J., et al. Engineering Hydrogels for Biofabrication. Adv. Mater. (2013); Murphy S. V., et al. Evaluation of Hydrogels for Bio-printing Applications. J. of Biomed. Mater. Res. (2012)).

SUMMARY OF THE INVENTION

It is therefore desirable to provide a biocompatible compound that is capable of forming a hydrogel, that meets at least some of the above requirements to a higher extent than currently available hydrogels and that is not restricted by the above mentioned limitations, which is particularly suitable to be used in biofabrication.

The objects of the present invention are solved by the use of a peptide and/or peptidomimetic capable of self-assembling and forming a (nanofibrous) hydrogel, having the general formula I:

$$Z_a\text{—}(X)_b\text{—}(Y)_c\text{—}Z'_d \qquad \text{I}$$

wherein
Z is an N-terminal protecting group;
a is 0 or 1, preferably 1;
X is, at each occurrence, independently selected from the group consisting of aliphatic amino acids and aliphatic amino acid derivatives, and wherein the overall hydrophobicity decreases from N- to C-terminus;
b is an integer selected from 1 to 7;
Y is selected from the group consisting of polar amino acids and polar amino acid derivatives;
c is 0, 1 or 2;
Z' is a C-terminal polar head group; and
d is 1,
and b+c is at least 2,
in bio fabrication.

The inventors have found that said aliphatic amino acids and aliphatic amino acid derivatives need to exhibit an overall decrease in hydrophobicity from the N-terminus to the C-terminus of said peptide and/or peptoid in order to form nanofibrous hydrogels.

The terms "peptoid" and "peptidomimetic" are used herein interchangeably and refer to molecules designed to mimic a peptide. Peptoids or peptidomimetics can arise either from modification of an existing peptide, or by designing similar systems that mimic peptides. These modifications involve changes to the peptide that will not occur naturally (such as altered backbones and/or the incorporation of non-natural amino acids).

In particular, peptoids are a subclass of peptidomimetics. In peptoids, the side chains are connected to the nitrogen of the peptide backbone, differently to normal peptides. Peptidomimetics can have a regular peptide backbone where only the normally occurring amino acids are exchanged with a chemically different but similar amino acids, such as leucine to norleucine. In the present disclosure, the terms are used interchangeably.

The peptides, peptidomimetics and peptoids disclosed herein are suitable as ink(s) or (biomaterial) building block(s) in biofabrication, including bioprinting, (bio) moulding.

"Biofabrication" as used herein refers to the use of techniques, such as additive manufacturing (i.e. bio-printing) and moulding to create 2D and 3D structures or biological constructs from biomaterial building blocks (i.e. the peptides and/or peptidomimetics according to the invention). During the fabrication process, bioactive moieties and cells can be incorporated in a precise fashion. In the specific example of "bio-printing", a computer-aided device is used to precisely deposit the biomaterial building block (ink), using a layer-by-layer approach, into the pre-determined, prescribed 3D geometry. The size of these structures range from the micro-scale to larger structures. Additives such as growth factors, cytokines, vitamins, minerals, oligonucleotides, small molecule drugs, and other bioactive moieties, and various cell types can also be accurately deposited concurrently or subsequently. Bio-inert components can be utilized as supports or fillers to create open inner spaces to mimic biological tissue. Such biological constructs can be subsequently implanted or used to investigate the interactions between cells and/or biomaterials, as well as to develop 3D disease models. In the specific example of "moulding", the biomaterial building block is deposited into a template of specific shape and dimensions, together with relevant bioactive moieties and cells.

(see Malda J., et al. Engineering Hydrogels for Biofabrication. Adv. Mater. (2013); Murphy S. V., et al. Evaluation of Hydrogels for Bio-printing Applications. J. of Biomed. Mater. Res. (2012)).

"Bioprinting" is part of the field tissue engineering which is the use of a combination of cells, engineering and materials methods, and suitable biochemical and physio-chemical factors to improve or replace biological functions.

Tissue engineering is used to repair or replace portions of or whole tissues (i.e., bone, cartilage, blood vessels, bladder, skin, muscle etc.). Often, the tissues involved require certain mechanical and structural properties for proper functioning.

The term "bioprinting" as used herein also comprises a process of making a tissue analog by depositing scaffolding or ink material (the peptides/peptidomimetics of the invention or. hydrogels thereof) alone, or mixed with cells, based on computer driven mimicking of a texture and a structure of a naturally occurring tissue An "ink" or "bio-ink" for bioprinting as used herein refers to the biomaterial building block that is sequentially deposited to build a macromolecular scaffold.

In one embodiment, said aliphatic amino acids and aliphatic amino acid derivatives, and said polar amino acids and polar amino acid derivatives are either D-amino acids or L-amino acids.

In one embodiment, said aliphatic amino acids are selected from the group consisting of alanine (Ala, A), homoallylglycine, homopropargylglycine, isoleucine (Ile, I), norleucine, leucine (Leu, L), valine (Val, V) and glycine (Gly, G), preferably from the group consisting of alanine (Ala, A), isoleucine (Ile, I), leucine (Leu, L), valine (Val, V) and glycine (Gly, G).

In one embodiment, all or a portion of said aliphatic amino acids are arranged in an order of decreasing amino acid size in the direction from N- to C-terminus, wherein the size of the aliphatic amino acids is defined as I=L>V>A>G.

In one embodiment, the very first N-terminal amino acid of said aliphatic amino acids is less crucial (it can be G, V or A). The inventors found that this specific first amino acid has not a dominant on this otherwise mandatory requirement of decreasing hydrophobicity from N- to C-terminus.

In one embodiment, said aliphatic amino acids have a sequence selected from

```
                                          (SEQ ID NO: 1)
            LIVAG, (SEQ ID NO: 2)
            ILVAG,
```

```
                                           (SEQ ID NO: 3)
            LIVAA, (SEQ ID NO: 4)
            LAVAG, (SEQ ID NO: 5)
            AIVAG (SEQ ID NO: 6)
            GIVAG (SEQ ID NO: 7)
            VIVAG (SEQ ID NO: 8)
            ALVAG (SEQ ID NO: 9)
            GLVAG (SEQ ID NO: 10)
            VLVAG (SEQ ID NO: 11)
            IVAG (SEQ ID NO: 12)
            LIVA (SEQ ID NO: 13)
            LIVG

IVA
            and

IV,
``` wherein, optionally, there is an A preceding such sequence at the N-terminus.

In one embodiment, all or a portion of the aliphatic amino acids are arranged in an order of identical amino acid size, preferably wherein said aliphatic amino acids arranged in order of identical amino acid size have a sequence with a length of 2 to 4 amino acids.

For example, said aliphatic amino acids arranged in an order of identical size have a sequence selected from LLLL (SEQ ID NO: 47), LLL, LL, IIII (SEQ ID NO: 48), III, II, VVVV (SEQ ID NO: 49), VVV, VV, AAAA (SEQ ID NO: 50), AAA, AA, GGGG (SEQ ID NO: 51), GGG, and GG.

In one embodiment, b is an integer from 1 to 7, preferably 2 to 7, or 2 to 6.

In one embodiment, said polar amino acids are selected from the group consisting of aspartic acid (Asp, D), asparagine (Asn, N), glutamic acid (Glu, E), glutamine (Gln, Q), 5-N-ethyl-glutamine (theanine), citrulline, thio-citrulline, cysteine (Cys, C), homocysteine, methionine (Met, M), ethionine, selenomethionine, telluromethionine, threonine (Thr, T), allothreonine, serine (Ser, S), homoserine, arginine (Arg, R), homoarginine, ornithine (Orn), lysine (Lys, K), N(6)-carboxymethyllysine, histidine (His, H), 2,4-diaminobutyric acid (Dab), 2,3-diaminopropionic acid (Dap), and N(6)-carboxymethyllysine,
wherein said polar amino acid is preferably selected from the group consisting of aspartic acid, asparagine, glutamic acid, glutamine, serine, threonine, methionine, lysine, ornithine (Orn), 2,4-diaminobutyric acid (Dab), and 2,3-diaminopropionic acid (Dap).

In one embodiment, c is 2 and said polar amino acids are identical amino acids, or c is 1 and said polar amino acid comprises any one of aspartic acid, asparagine, glutamic acid, glutamine, serine, threonine, cysteine, methionine, lysine, ornithine, 2,4-diaminobutyric acid (Dab) and histidine,
preferably lysine, ornithine, 2,4-diaminobutyric acid (Dab) and 2,3-diaminopropionic acid (Dap).

In one embodiment, $(Y)_b$ has a sequence selected from Asp, Asn, Glu, Gln, Ser, Thr, Cys, Met, Lys, Orn, Dab, His, Asn-Asn, Asp-Asp, Glu-Glu, Gln-Gln, Asn-Gln, Gln-Asn, Asp-Gln, Gln-Asp, Asn-Glu, Glu-Asn, Asp-Glu, Glu-Asp, Glu-Gln, Asp-Asn, Asn-Asp Thr-Thr, Ser-Ser, Thr-Ser, Ser-Thr, Asp-Ser, Ser-Asp, Ser-Asn, Asn-Ser, Gln-Ser, Ser-Gln, Glu-Ser, Ser-Glu, Asp-Thr, Thr-Asp, Thr-Asn, Asn-Thr, Gln-Thr, Thr-Gln, Glu-Thr, Thr-Glu, Cys-Asp, Cys-Lys, Cys-Ser, Cys-Thr, Cys-Orn, Cys-Dab, Cys-Dap, Lys-Lys, Lys-Ser, Lys-Thr, Lys-Orn, Lys-Dab, Lys-Dap, Ser-Lys, Ser-Orn, Ser-Dab, Ser-Dap, Orn-Lys, Orn-Orn, Orn-Ser, Orn-Thr, Orn-Dab, Orn-Dap, Dab-Lys, Dab-Ser, Dab-Thr, Dab-Orn, Dab-Dab, Dab-Dap, Dap-Lys, Dap-Ser, Dap-Thr, Dap-Orn, Dap-Dab, Dap-Dap.

In one embodiment, $(X)_a$—$(Y)_b$ has a sequence selected from the group consisting of

```
                                           (SEQ ID NO: 14)
            LIVAGD, (SEQ ID NO: 15)
            ILVAGD, (SEQ ID NO: 16)
            LIVAAD, (SEQ ID NO: 17)
            LAVAGD, (SEQ ID NO: 18)
            AIVAGD, (SEQ ID NO: 19)
            LIVAGE, (SEQ ID NO: 20)
            LIVAGK, (SEQ ID NO. 21)
            ILVAGK, (SEQ ID NO: 22)
            LIVAGT, (SEQ ID NO: 23)
            AIVAGT, (SEQ ID NO: 24)
            AIVAGK, (SEQ ID NO: 25)
            LIVAD, (SEQ ID NO: 26)
            LIVGD, (SEQ ID NO: 27)
            IVAD, (SEQ ID NO: 28)
            IVAK, (SEQ ID NO: 29)
            IIID, (SEQ ID NO: 30)
            IIIK,

IVD,

IID,

LVE,
```

-continued

| | |
|---|---|
| IVE, | |
| LVD, | |
| VIE, | |
| VID, | |
| VLD, | |
| VLE, | |
| LLE, | |
| LLD, | |
| IIE, | |
| ID, | |
| IE, | |
| LIVAGOrn, | (SEQ ID NO: 31) |
| ILVAGOrn, | (SEQ ID NO: 32) |
| AIVAGOrn, | (SEQ ID NO: 33) |
| LIVAGDab, | (SEQ ID NO: 34) |
| ILVAGDab, | (SEQ ID NO: 35) |
| AIVAGDab, | (SEQ ID NO: 36) |
| LIVAGDap, | (SEQ ID NO: 37) |
| ILVAGDap, | (SEQ ID NO: 38) |
| AIVAGDap, | (SEQ ID NO: 39) |
| IVOrn, | |
| IVDab, | |
| IVDap, | |
| IVK, | |
| VIK, | |
| VIOrn, | |
| VIDab, | |
| VIDap, | |
| LIVAGDD, | (SEQ ID NO: 40) |
| LIVAGEE, | (SEQ ID NO: 41) |
| LIVAGKC, | (SEQ ID NO: 42) |
| LIVAGS, | (SEQ ID NO: 43) |
| ILVAGS, | (SEQ ID NO: 44) |
| AIVAGS, and | (SEQ ID NO: 45) |
| ILVAGT. | (SEQ ID NO: 46) |

In one embodiment, a is 1 and said N-terminal protecting group Z has the general formula —C(O)—R, wherein R is selected from the group consisting of H, unsubstituted or substituted alkyls, and unsubstituted or substituted aryls, wherein R is preferably selected from the group consisting of methyl, ethyl, propyl, isopropyl, butyl and isobutyl.

In one embodiment, said N-terminal protecting group Z is an acetyl group.

In one embodiment, said N-terminal protecting group Z is a peptidomimetic molecule, including natural and synthetic amino acid derivatives, wherein the N-terminus of said peptidomimetic molecule may be modified with a functional group selected from the group consisting of carboxylic acid, amide, alcohol, aldehyde, amine, imine, nitrile, an urea analog, phosphate, carbonate, sulfate, nitrate, maleimide, vinyl sulfone, azide, alkyne, alkene, carbohydrate, imide, peroxide, ester, aryl, ketone, sulphite, nitrite, phosphonate, and silane.

In one embodiment, said C-terminal polar head group Z' is selected from
  polar functional groups,
    such as (but not limited to)
      —COOH, —COOR, —COR, —CONHR or —CONRR' with R and R' being selected from the group consisting of H, unsubstituted or substituted alkyls, and unsubstituted or substituted aryls,
      —NH$_2$, —OH, —SH, —CHO, maleimide, imidoester, carbodiimide ester, isocyanate;
  small molecules,
    such as (but not limited to) sugars, alcohols, hydroxy acids, amino acids, vitamins, biotin, L-Dopa, thyroxine;
  linkers terminating in a polar functional group,
    such as (but not limited to) ethylenediamine, PEG, carbodiimide ester, imidoester;
  linkers coupled to small molecules or vitamins,
    such as biotin, sugars, hydroxy acids,
wherein the polar head group Z' is preferably an amide group.

In one embodiment, the C-terminal amino acid is further functionalized.

In one embodiment, the polar functional group(s) can be used for chemical conjugation or coupling of at least one compound selected from
  bioactive molecules or moieties,
    such as growth factors, cytokines, lipids, cell receptor ligands, hormones, prodrugs, drugs, vitamins, antigens, antibodies, antibody fragments, oligonucleotides (including but not limited to DNA, messenger RNA, short hairpin RNA, small interfering RNA, microRNA, peptide nucleic acids, aptamers), saccharides;
  label(s), dye(s),
    such as imaging contrast agents;
  pathogens,
    such as viruses, bacteria and parasites;
  micro- and nanoparticles
or combinations thereof wherein said chemical conjugation can be carried out before or after self-assembly of the peptide and/or peptidomimetic.

In one embodiment, said C-terminal polar head group Z' is a peptidomimetic molecule, including natural and synthetic amino acid derivatives, wherein the C-terminus of said peptidomimetic molecule may be modified with a functional group selected from the group consisting of carboxylic acid, amide, alcohol, aldehyde, amine, imine, nitrile, an urea analog, phosphate, carbonate, sulfate, nitrate, maleimide, vinyl sulfone, azide, alkyne, alkene, carbohydrate, imide, peroxide, ester, aryl, ketone, sulphite, nitrite, phosphonate, and silane.

In one embodiment, b+c is at least 2, preferably 2 to 9, more preferably 3 to 7 or 2 to 7.

In one embodiment, the use according to the invention comprises a conformational change of the peptide(s) and/or peptidomimetic(s) during self-assembly,
preferably a conformational change from a random coil conformation to a helical intermediate structure (such as α-helical fibrils) to a final beta turn or cross beta conformation, such as fibrils which further aggregate and/or condense into nanofibers (which make up a network),
wherein, preferably, the conformational change is dependent on the peptide concentration, ionic environment, pH and temperature.

In one embodiment, at least one peptide and/or peptidomimetic as herein defined forms a hydrogel.

The hydrogel is formed by self-assembly of the peptide and/or peptiod, as explained in further detail below.

In one embodiment, different peptide(s) and/or peptidomimetic(s) as defined herein are used to form the hydro gel.

Preferably, different peptide(s) and/or peptidomimetic(s) refers to peptide(s) and/or peptidomimetic(s) that differ in their amino acid sequence, polar head group(s), conjugated/coupled compounds (such as different labels, bioactive molecules etc) or combinations thereof.

In one embodiment, the use according to the invention comprises stimuli-responsive gelation of at least one peptide and/or peptidomimetic as defined herein,
wherein said stimulus/stimuli or gelation condition(s) is/are selected from pH, salt concentration and/or temperature.

The term "stimuli-responsive gelation" as used herein refers to self-assembly which is triggered or enhanced by the addition of a salt solution, pH change and/or temperature change. For this subclass peptide hydrogels, the peptide solutions transition from a fluid to a hydrogel in the presence of these stimuli.

In one embodiment, the peptide and/or peptidomimetic comprises as the polar head group basic amino acid(s), such as lysine or lysine-mimetic molecules, preferably amidated basic amino acid(s),
and said peptide exhibits stimuli-responsive gelation, preferably enhanced gelation in the presence of salt at physiological conditions (such as 0.9% saline and PBS) and/or at a pH above physiological pH, preferably pH 7 to 10 (such as by adding NaOH).

In one embodiment, the peptide and/or peptidomimetic comprises as the polar head group acidic amino acid(s),
and said peptide exhibits stimuli-responsive gelation, preferably enhanced gelation at a pH below physiological pH 7, preferably pH 2 to 6,
and wherein amidation or esterification of said acidic amino acid(s) removes said pH sensitivity.

In one embodiment, the gelation condition(s) (in particular pH, salt concentration and/or temperature) influence the properties of the hydrogel obtained, such as its mechanical stiffness, rigidity, porosity.

In one embodiment, at least one peptide and/or peptidomimetic as defined herein is dissolved in water and wherein the solution obtained can be dispensed through needles and print heads.

In one embodiment, the use according to the invention comprises conjugation or coupling of further compound(s) to the peptides and/or peptidomimetic, preferably to the polar functional group(s), post-assembly,
wherein said further compound(s) can be selected from
bioactive molecules or moieties,
such as growth factors, cytokines, lipids, cell receptor ligands, hormones, prodrugs, drugs, vitamins, antigens, antibodies, antibody fragments, oligonucleotides (including but not limited to DNA, messenger RNA, short hairpin RNA, small interfering RNA, microRNA, peptide nucleic acids, aptamers), saccharides;
label(s), dye(s),
such as imaging contrast agents;
pathogens,
such as viruses, bacteria and parasites;
micro- and nanoparticles
or combinations thereof.

In one embodiment, the peptide and/or peptidomimetic is present at a concentration in the range of from 0.1% to 30% (w/w), preferably 0.1% to 20% (w/w), more preferably 0.1% to 10% (w/w), more preferably 0.1% to 5% (w/w), even more preferably 0.1% to 3% (w/w), with respect to the total weight of said hydrogel.

In one embodiment, the use according to the invention comprises the addition or mixing of cells prior or during gelation, which are encapsulated by the hydrogel,
wherein said cells can be stem cells (mesenchymal, progenitor, embryonic and induced pluripotent stem cells), transdifferentiated progenitor cells and primary cells isolated from patient samples (fibroblasts, nucleus pulposus).
preferably comprising the addition of further compound(s) prior or during gelation, which are co-encapsulated by the hydrogel.

In one embodiment, the use according to the invention comprises the addition of cells onto the printed hydrogel, wherein said cells can be stem cells (adult, progenitor, embryonic and induced pluripotent stem cells), transdifferentiated progenitor cells, and primary cells (isolated from patients) and cell lines (such as epithelial, neuronal, hematopoietic and cancer cells).

In one embodiment, the use according to the invention comprises
(1) the addition or mixing of cells prior or during gelation, which are encapsulated by the hydrogel, and
(2) subsequently comprising the addition of cells onto the printed hydrogel,
wherein said cells of (1) and (2) are the same or different, and can be stem cells (adult, progenitor, embryonic and induced pluripotent stem cells), transdifferentiated progenitor cells, and primary cells (isolated from patients) and cell lines (such as epithelial, neuronal, hematopoietic and cancer cells).

In one embodiment, the use according to the invention comprises the addition of cross-linkers to the peptide(s) and/or peptidomimetic(s),
wherein said cross-linkers preferably include short linkers, linear and branched polymers, polymers conjugated with bioactive molecules or moieties.

The objects of the present invention are solved by a method of preparing a hydrogel, the method comprising dissolving at least one peptide and/or peptidomimetic as defined herein in an aqueous solution, such as water, or in a polar solvent, such as ethanol.

In one embodiment, the method of the invention comprises stimuli-responsive gelation of the at least one peptide and/or peptidomimetic as defined herein,
wherein said stimulus/stimuli or gelation condition(s) is/are selected from pH, salt concentration and/or temperature.

In one embodiment, the at least one peptide and/or peptidomimetic comprises as the polar head group basic amino acid(s), such as lysine or lysine-mimetic molecules, preferably amidated basic amino acid(s),
and gelation is carried out in the presence of salt at physiological conditions (such as PBS or 0.9% saline and PBS) and/or at a pH above physiological pH, preferably pH 7 to 10 (such as by adding NaOH).

In one embodiment, the at least one peptide and/or peptidomimetic comprises as the polar head group acidic amino acid(s),
and gelation is carried out at a pH below physiological pH 7, preferably pH 2 to 6.

In one embodiment, the dissolved peptide and/or peptidomimetic is further warmed or heated, wherein the temperature is in the range from 20° C. to 90° C., preferably from about 30° C. to 70° C., more preferably from about 37° C. to 70° C.

In one embodiment, the at least one peptide and/or peptidomimetic is dissolved at a concentration from 0.01 µg/ml to 100 mg/ml, preferably at a concentration from 1 mg/ml to 50 mg/ml, more preferably at a concentration from about 1 mg/ml to about 20 mg/ml.

The objects of the present invention are solved by a method of preparing continuous fibres, the method comprising
  dissolving at least one peptide and/or peptidomimetic as defined herein in an aqueous solution, such as water, and
  dispensing the solution obtained through needles, print heads, fine tubings and/or microfluidic devices into a buffered solution, such as PBS.

In one embodiment, the method comprises the addition of further compound(s) prior or during gelation/self-assembly, which are encapsulated by the hydrogel,
  wherein said further compound(s) can be selected from bioactive molecules or moieties,
    such as growth factors, cytokines, lipids, cell receptor ligands, hormones, prodrugs, drugs, vitamins, antigens, antibodies, antibody fragments, oligonucleotides (including but not limited to DNA, messenger RNA, short hairpin RNA, small interfering RNA, microRNA, peptide nucleic acids, aptamers), saccharides;
  label(s), dye(s),
    such as imaging contrast agents;
  pathogens,
    such as viruses, bacteria and parasites;
  quantum dots, nano- and microparticles,
  or combinations thereof.

In one embodiment, the method comprises the addition or mixing of cells prior or during gelation/self-assembly, which are encapsulated by the hydrogel,
  wherein said cells can be stem cells (mesenchymal, progenitor, embryonic and induced pluripotent stem cells), transdifferentiated progenitor cells and primary cells isolated from patient samples (fibroblasts, nucleus pulposus).

preferably comprising the addition of further compound(s) prior or during gelation (such as defined herein), which are co-encapsulated by the hydrogel.

In one embodiment, the method comprises the addition of cells onto the printed hydrogel, wherein said cells can be stem cells (adult, progenitor, embryonic and induced pluripotent stem cells), transdifferentiated progenitor cells, and primary cells (isolated from patients) and cell lines (such as epithelial, neuronal, hematopoietic and cancer cells).

In one embodiment, the method comprises the following steps:
(1) the addition or mixing of cells prior or during gelation, which are encapsulated by the hydrogel, and
(2) subsequently the addition of cells onto the printed hydrogel,
wherein said cells of (1) and (2) are the same or different, and can be stem cells (adult, progenitor, embryonic and induced pluripotent stem cells), transdifferentiated progenitor cells, and primary cells (isolated from patients) and cell lines (such as epithelial, neuronal, hematopoietic and cancer cells).

In one embodiment, the method comprises the addition of cross-linkers to the peptide(s) and/or peptidomimetic(s) prior, during or after gelation/self-assembly,
wherein said cross-linkers preferably include short linkers, linear and branched polymers, polymers conjugated with bioactive molecules or moieties (such as defined in herein), wherein, preferably, said cross-linkers interact electrostatically with the peptides and/or peptidomimetic(s) during self-assembly.

In one embodiment, the method comprises the use of different peptide(s) and/or peptidomimetic(s).

Preferably, different peptide(s) and/or peptidomimetic(s) refers to peptide(s) and/or peptidomimetic(s) that differ in their amino acid sequence, polar head group(s), conjugated/coupled compounds (such as different labels, bioactive molecules etc) or combinations thereof.

The objects of the present invention are solved by the use of a hydrogel obtained by a method (for preparing a hydrogel and/or for preparing continuous fibers) according to the invention for substrate-mediated gene delivery,
wherein oligonucleotides are encapsulated in the hydrogel and cells are co-encapsulated or seeded onto said hydrogel.

The objects of the present invention are solved by the use (of a peptide and/or peptidomimetic for biofabrication) according to the invention or the use of a hydrogel obtained by a method(for preparing a hydrogel and/or for preparing continuous fibers) according to the invention,for obtaining 2D mini-hydrogel arrays,
preferably comprising using printers, pintools and microcontact printing.

Preferably, a microarray of the invention comprises hydrogels that encapsulate different biomolecules, drugs, compounds, cells etc.

In one embodiment, said use comprises printing the 2D mini-hydrogels onto electrical circuits or piezoelectric surfaces that conduct current.

The objects of the present invention are solved by the use (of a peptide and/or peptidomimetic for biofabrication) according to the invention or the use of a hydrogel obtained by a method (for preparing a hydrogel and/or for preparing continuous fibers) according to the invention,as injectable or for injectable therapies,
such as for the treatment of degenerative disc disease.

An injectable is preferably an injectable scaffold or an injectable implant or an implantable scaffold.

By virtue of their self-assembling properties, the stimuli-responsive ultrashort peptides of the present invention are ideal candidates for injectable scaffolds. Such scaffolds can be injected as semi-viscous solutions that complete assembly in situ. Irregular-shaped defects can be fully filled, facilitating scaffold integration with native tissue. These injectable formulations offer significant advantages over ex vivo techniques of preparing nanofibrous scaffolds, such as electrospinning, which have to be surgically implanted. During the process of in situ gelation, the ability to modulate gelation rate enables the clinician to sculpt the hydrogel construct into the desired shape for applications such as dermal fillers. Furthermore, the biocompatibility and in vivo stability bodes well for implants that need to persist for several months. Taking into consideration the stiffness and tunable mechanical properties, we are particularly interested in developing injectable therapies and implantable scaffolds that fulfill mechanically supportive roles.

The objects of the present invention are solved by the use (of a peptide and/or peptidomimetic for biofabrication) according to the invention or the use of a hydrogel obtained by a method (for preparing a hydrogel and/or for preparing continuous fibers) according to the invention, comprising bioprinting, such as 3D microdroplet printing, and biomoulding.

In one embodiment, said use is for obtaining 3D organoid structures or 3D macromolecular biological constructs.

An organoid structure is a structure resembling an organe.

The term "3D organoid structures" or "3D macromolecular biological constructs" refers to samples in which various cell types are integrated in a 3D scaffold containing various biochemical cues, in a fashion which resembles native tissue. These constructs can potentially be used as implants, disease models and models to study cell-cell and cell-substrate interactions.

In one embodiment, said use comprises the use of moulds (such as of silicone) to pattern the hydrogels in 3D.

In one embodiment, said use is for obtaining multi-cellular constructs,
which comprise different cells/cell types,
which preferably comprise co-encapsulated further compound(s) (such as defined in herein) and/or cross-linkers (such as defined herein).

In one embodiment, said use is for obtaining 3D cellular constructs or scaffolds comprising encapsulated cells and cells deposited or printed onto the surface of the printed/fabricated scaffold.

In one embodiment, said use is for
preparation of cell based assays,
    preferably for identifying patient specimens, more preferably for identifying patient specimens containing pathogens (e.g. dengue, malaria, norovirus), which do not infect primary cells that have lost their native phenotype;
recovery of infected cells to identify and expand pathogen(s) of interest,
    preferably for elucidating mechanism(s) of infection and/or enabling the design of molecules that inhibit pathogen infection and/or replication.

The objects of the present invention are solved by a method for obtaining a multi-cellular construct, comprising
preparing a hydrogel by the method (for preparing a hydrogel and/or for preparing continuous fibers) according to the invention,
comprising the addition or mixing of different cells or cell types prior or during gelation/self-assembly, which are encapsulated by the hydrogel,
wherein said cells can be stem cells (mesenchymal, progenitor, embryonic and induced pluripotent stem cells), transdifferentiated progenitor cells and primary cells isolated from patient samples (fibroblasts, nucleus pulposus).
preferably comprising the addition of further compound(s) (such as defined herein) prior or during gelation, which are co-encapsulated by the hydrogel,
optionally comprising the addition of cross-linkers (such as defined herein) to the peptide(s) and/or peptidomimetic(s) prior or during gelation/self-assembly,
obtaining the multi-cellular construct.

The objects of the present invention are solved by a method for obtaining a multi-cellular construct, comprising
preparing a hydrogel by the method (for preparing a hydrogel and/or for preparing continuous fibers) according to the invention,
comprising the following steps:
(1) the addition or mixing of cells prior or during gelation, which are encapsulated by the hydrogel, and
(2) subsequently the addition of cells onto the printed hydrogel,
wherein said cells of (1) and (2) are different,
and can be stem cells (adult, progenitor, embryonic and induced pluripotent stem cells), transdifferentiated progenitor cells, and primary cells (isolated from patients) and cell lines (such as epithelial, neuronal, hematopoietic and cancer cells),
preferably comprising the addition of further compound(s) (such as defined herein) prior or during gelation, which are co-encapsulated by the hydrogel,
optionally comprising the addition of cross-linkers (such as defined herein) to the peptide(s) and/or peptidomimetic(s) prior or during gelation/self-assembly,
obtaining the multi-cellular construct.

In one embodiment, the multi-cellular construct obtained is formed in a mould (such as of silicone).

The objects of the present invention are solved by a multi-cellular construct obtained according to the methods for obtaining a multi-cellular construct according to the invention and as described herein above,
preferably comprising micro-domains.

The objects of the present invention are solved by the use of a 3D biological construct obtained by a method (for obtaining a 3D biological construct) according to the invention or of a multi-cellular construct obtained according to the method (for obtaining a multi-cellular construct) according to the invention as:
organoid model for screening biomolecule libraries, studying cell behavior, infectivity of pathogens and disease progression, screening infected patient samples, evaluating drug efficacy and toxicity,
tissue-engineered implant for regenerative medicine, and/or
in vitro disease model.

In one embodiment, said use is for
preparation of cell based assays,
    preferably for identifying patient specimens, more preferably for identifying patient specimens containing pathogens (e.g. dengue, malaria, norovirus), which do not infect primary cells that have lost their native phenotype;
recovery of infected cells to identify and expand pathogen(s) of interest,
    preferably for elucidating mechanism(s) of infection and/or enabling the design of molecules that inhibit pathogen infection and/or replication.

Amphiphilic Peptides

In one embodiment, the present invention provides the use of a peptide, peptidomimetic and/or peptoid capable of self-assembling and forming a (nanofibrous) hydrogel, having the general formula I:

$$Z_a\text{—}(X)_b\text{—}(Y)_c\text{—}Z'_d \qquad \text{I}$$

wherein
Z is an N-terminal protecting group;
a is 0 or 1, preferably 1;
X is, at each occurrence, independently selected from the group consisting of aliphatic amino acids and aliphatic amino acid derivatives, and wherein the overall hydrophobicity decreases from N- to C-terminus;
b is an integer selected from 1 to 7;
Y is selected from the group consisting of polar amino acids and polar amino acid derivatives;
c is not 0 but 1 or 2;
Z' is a C-terminal polar head group; and
d is 1,
and b+c is at least 2.

These peptides, peptidomimetics and/or peptoids can be referred to as amphiphilic peptides or peptide amphiphiles that self-assemble into three-dimensional networks which entrap water to form hydrogels. The peptide amphiphile can be a peptide, peptidomimetic, peptoid or peptide-conjugate-having the formula described.

In the following, the embodiments with peptides, peptidomimetics and/or peptoids, wherein
c is 0
are further disclosed:

Hydrophobic Peptides

The objects of the present invention are solved by a hydrophobic peptide and/or peptidomimetic capable of forming a (nanofibrous) hydrogel, the hydrophobic peptide and/or peptidomimetic having the general formula II:

$$Z\text{-}(X)_a\text{—}Z'_b \qquad \text{II}$$

wherein
Z is an N-terminal protecting group;
X is a hydrophobic amino acid sequence of aliphatic amino acids, which, at each occurrence, are independently selected from the group consisting of aliphatic amino acids and aliphatic amino acid derivatives;
a is an integer selected from 2 to 6, preferably 2 to 5;
Z' is a C-terminal group; and
b is 0 or 1.

The inventors have found that said aliphatic amino acids and aliphatic amino acid derivatives need to exhibit an overall decrease in hydrophobicity from the N-terminus to the C-terminus of said peptide and/or peptidomimetic.

The terms "peptoid" and "peptidomimetic" are used herein interchangeably and refer to molecules designed to mimic a peptide. Peptoids or peptidomimetics can arise either from modification of an existing peptide, or by designing similar systems that mimic peptides. These modifications involve changes to the peptide that will not occur naturally (such as altered backbones and/or the incorporation of non-natural amino acids). See above.

In one embodiment, said aliphatic amino acids and aliphatic amino acid derivatives are either D-amino acids or L-amino acids.

In one embodiment, said aliphatic amino acids are selected from the group consisting of alanine (Ala, A), homoallylglycine, homopropargylglycine, isoleucine (Ile, I), norleucine, leucine (Leu, L), valine (Val, V) and glycine (Gly, G), preferably from the group consisting of alanine (Ala, A), isoleucine (Ile, I), leucine (Leu, L), valine (Val, V) and glycine (Gly, G).

In one embodiment, all or a portion of said aliphatic amino acids are arranged in an order of decreasing amino acid size in the direction from N- to C-terminus, wherein the size of the aliphatic amino acids is defined as I=L>V>A>G.

In one embodiment, said aliphatic amino acids arranged in an order of decreasing amino acid size have a sequence which is a repetitive or non-repetitive sequence.

In one embodiment, the very first N-terminal amino acid of said aliphatic amino acids is less crucial (it can be G, V or A). The inventors found that this specific first amino acid has not a dominant on this otherwise mandatory requirement of decreasing hydrophobicity from N to C-terminus.

In one embodiment, the first N-terminal amino acid of said aliphatic amino acids is G, V or A.

In one embodiment, said aliphatic amino acids have a sequence selected from

ILVAG, (SEQ ID NO: 1)

LIVAG, (SEQ ID NO: 2)

IVAG, (SEQ ID NO: 3)

LVAG, (SEQ ID NO: 4)

ILVA, (SEQ ID NO: 5)

LIVA, (SEQ ID NO: 6)

IVG, (SEQ ID NO: 13)

VIG, (SEQ ID NO: 14)

IVA, (SEQ ID NO: 15)

VIA, (SEQ ID NO: 16)

VI (SEQ ID NO: 17)
and

IV, (SEQ ID NO: 18)

wherein, optionally, there is an G, V or A preceding such sequence at the N-terminus, such as

AIVAG, (SEQ ID NO. 7)

GIVAG, (SEQ ID NO. 8)

VIVAG, (SEQ ID NO. 9)

ALVAG, (SEQ ID NO. 10)

GLVAG, (SEQ ID NO. 11)

-continued

VLVAG. (SEQ ID NO. 12)

In one embodiment, $(X)_a$ has a sequence selected from the group consisting of SEQ ID NOs. 1 to 18, preferably the sequence with SEQ ID NO: 1 and SEQ ID NO: 2.

In one embodiment, all or a portion of the aliphatic amino acids are arranged in an order of identical amino acid size, preferably wherein said aliphatic amino acids arranged in order of identical amino acid size have a sequence with a length of 2 to 4 amino acids.

For example, said aliphatic amino acids arranged in an order of identical size have a sequence selected from LLLL, (SEQ ID NO: 47), LLL, LL, IIII(SEQ ID NO: 48), III, II, VVVV(SEQ ID NO: 49), VVV, VV, AAAA (SEQ ID NO:50), AAA, AA, GGGG (SEQ ID NO: 51), GGG, and GG.

In one embodiment, said N-terminal protecting group Z has the general formula —C(O)—R, wherein R is selected from the group consisting of H, unsubstituted or substituted alkyls, and unsubstituted or substituted aryls, wherein R is preferably selected from the group consisting of methyl, ethyl, propyl, isopropyl, butyl and isobutyl.

In one embodiment, said N-terminal protecting group Z is an acetyl group.

In one embodiment, said N-terminal protecting group Z is a peptidomimetic molecule, including natural and synthetic amino acid derivatives, wherein the N-terminus of said peptidomimetic molecule may be modified with a functional group selected from the group consisting of carboxylic acid, amide, alcohol, aldehyde, amine, imine, nitrile, an urea analog, phosphate, carbonate, sulfate, nitrate, maleimide, vinyl sulfone, azide, alkyne, alkene, carbohydrate, imide, peroxide, ester, aryl, ketone, sulphite, nitrite, phosphonate, and silane.

In one embodiment, said C-terminal group Z' is a non-amino acid, preferably selected from the group of small molecules, functional groups and linkers. Such C-terminal groups Z' can be polar or non-polar moieties used to functionalize the peptide and/or peptidomimetic of the invention.

In one embodiment, said C-terminal group Z' is selected from
  functional groups, such as polar or non-polar functional groups,
    such as (but not limited to)
      —COOH, —COOR, —COR, —CONHR or —CONRR' with R and R' being selected from the group consisting of H, unsubstituted or substituted alkyls, and unsubstituted or substituted aryls,
      —NH$_2$, —OH, —SH, —CHO, maleimide, imidoester, carbodiimide ester, isocyanate;
  small molecules,
    such as (but not limited to) sugars, alcohols, hydroxy acids, amino acids, vitamins, biotin, L-Dopa, thyroxine;
  linkers terminating in a polar functional group,
    such as (but not limited to) ethylenediamine, PEG, carbodiimide ester, imidoester;
  linkers coupled to small molecules or vitamins,
    such as biotin, sugars, hydroxy acids, In one embodiment, wherein said C-terminal group Z' can be used for chemical conjugation or coupling of at least one compound selected from
  bioactive molecules or moieties,
    such as growth factors, cytokines, lipids, cell receptor ligands, hormones, prodrugs, drugs, vitamins, antigens, antibodies, antibody fragments, oligonucleotides (including but not limited to DNA, messenger RNA, short hairpin RNA, small interfering RNA, microRNA, peptide nucleic acids, aptamers), saccharides;
  label(s), dye(s),
    such as fluorescent or radioactive label(s), imaging contrast agents;
  pathogens,
    such as viruses, bacteria and parasites;
  micro- and nanoparticles
  or combinations thereof
wherein said chemical conjugation can be carried out before or after self-assembly of the peptide and/or peptidomimetic.

In one embodiment, the C-terminus of the peptide and/or peptidomimetic is functionalized (without the use of a C-terminal group or linker), such as by chemical conjugation or coupling of at least one compound selected from
  bioactive molecules or moieties,
    such as growth factors, cytokines, lipids, cell receptor ligands, hormones, prodrugs, drugs, vitamins, antigens, antibodies, antibody fragments, oligonucleotides (including but not limited to DNA, messenger RNA, short hairpin RNA, small interfering RNA, microRNA, peptide nucleic acids, aptamers), saccharides;
  label(s), dye(s),
    such as fluorescent or radioactive label(s), imaging contrast agents;
  pathogens,
    such as viruses, bacteria and parasites;
  micro- and nanoparticles
  or combinations thereof
wherein said chemical conjugation can be carried out before or after self-assembly of the peptide and/or peptidomimetic.

In one embodiment, said C-terminal group Z' is a peptidomimetic molecule, including natural and synthetic amino acid derivatives, wherein the C-terminus of said peptidomimetic molecule may be modified with a functional group selected from the group consisting of carboxylic acid, amide, alcohol, aldehyde, amine, imine, nitrile, an urea analog, phosphate, carbonate, sulfate, nitrate, maleimide, vinyl sulfone, azide, alkyne, alkene, carbohydrate, imide, peroxide, ester, aryl, ketone, sulphite, nitrite, phosphonate, and silane.

In one embodiment, the hydrophobic peptide and/or peptidomimetic according to the invention is being stable in aqueous solution at physiological conditions at ambient temperature for a period of time in the range from 1 day to at least 6 months, preferably to at least 8 months more preferably to at least 12 months.

In one embodiment, the hydrophobic peptide and/or peptidomimetic according to the invention is being stable in aqueous solution at physiological conditions, at a temperature up to 90° C., for at least 1 hour.

The objects of the present invention are solved by a composition or mixture comprising
  (a) at least one hydrophobic peptide and/or peptidomimetic of the present invention, and (b) at least one hydrophobic peptide and/or peptidomimetic capable of forming a hydrogel, the hydrophobic peptide and/or peptidomimetic having the general formula:

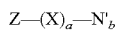

wherein
Z is as defined herein for the hydrophobic peptide and/or peptidomimetic of the present invention;
X is as defined herein for the hydrophobic peptide and/or peptidomimetic of the present invention;
a is as defined herein for the hydrophobic peptide and/or peptidomimetic of the present invention;
N' is a non-polar C-terminal group which differs from Z', the polar C-terminal group as defined herein for the hydrophobic peptide and/or peptidomimetic of the present invention;
and is preferably carboxylic acid, amide, alcohol, biotin, maleimide, sugars, and hydroxyacids,
and
b is 0 or 1.

The objects of the present invention are solved by a hydrogel comprising the hydrophobic peptide and/or peptidomimetic of the present invention.

In one embodiment, the hydrogel is stable in aqueous solution at ambient temperature for a period of at least 7 days, preferably at least 2 to 4 weeks, more preferably at least 1 to 6 months.

In one embodiment, the hydrogel is characterized by a storage modulus G' to loss modulus G" ratio that is greater than 2.

In one embodiment, the hydrogel is characterized by a storage modulus G' from 100 Pa to 80,000 Pa at a frequency in the range of from 0.02 Hz to 16 Hz.

In one embodiment, the hydrogel has a higher mechanical strength than collagen or its hydrolyzed form (gelatin).

The objects of the present invention are solved by a hydrogel comprising
(a) at least one hydrophobic peptide and/or peptidomimetic of the present invention, and
(b) at least one hydrophobic peptide and/or peptidomimetic with a non-polar head group.

Said at least one "hydrophobic peptide and/or peptidomimetic with a non-polar head group" is capable of forming a hydrogel and has the general formula:

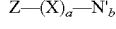

wherein
Z, X and a are as defined herein for the hydrophobic peptide and/or peptidomimetic of the present invention;
N' is a non-polar C-terminal group which differs from Z', the polar C-terminal group as defined herein for the hydrophobic peptide and/or peptidomimetic of the present invention;
and is preferably carboxylic acid, amide, alcohol, biotin, maleimide, sugars, and hydroxyacids,
and
b is 0 or 1.

In one embodiment, the hydrogel comprises fibers of the hydrophobic peptide and/or peptidomimetic of the invention or fibers of the hydrophobic peptide and/or peptidomimetic with a non-polar head group as defined above, said fibers defining a network that is capable of entrapping at least one of a microorganism, a virus particle, a peptide, a peptoid, a protein, a nucleic acid, an oligosaccharide, a polysaccharide, a vitamin, an inorganic molecule, a synthetic polymer, a small organic molecule, a micro- or nanoparticle or a pharmaceutically active compound.

In one embodiment, the hydrogel comprises at least one of a microorganism, a virus particle, a peptide, a peptoid, a protein, a nucleic acid, an oligosaccharide, a polysaccharide, a vitamin, an inorganic molecule, a synthetic polymer, a small organic molecule, a micro- or nanoparticle or a pharmaceutically active compound entrapped by the network of fibers of the hydrophobic polymer.

In one embodiment, the fibers of the hydrophobic polymer are coupled to the at least one of a microorganism, a virus particle, a peptide, a peptoid, a protein, a nucleic acid, an oligosaccharide, a polysaccharide, a vitamin, an inorganic molecule, a synthetic polymer, a small organic molecule, a micro- or nanoparticle or a pharmaceutically active compound entrapped by the network of fibers of the amphiphilic polymer.

In one embodiment, the hydrogel is comprised in at least one of a fuel cell, a solar cell, an electronic cell, a biosensing device, a medical device, an implant, a pharmaceutical composition and a cosmetic composition.

In one embodiment, the hydrogel is injectable.

The objects of the present invention are solved by the use of the hydrogel according to the present invention in at least one of the following:
release of a pharmaceutically active compound and/or delivery of bioactive moieties,
medical tool kit,
a fuel cell,
a solar cell,
an electronic cell,
regenerative medicine and tissue regeneration,
wound healing,
2D and 3D synthetic cell culture substrate,
stem cell therapy,
injectable therapies,
biosensor development,
biofunctionalized surfaces,
biofabrication, such as bio-printing, and
gene therapy.

For the uses, we refer to the above described uses in biofabrication and the subsequent embodiments and methods, which also apply to the hydrophobic peptides and/or peptidomimetics.

The objects of the present invention are solved by a method of preparing a hydrogel, the method comprising dissolving a hydrophobic peptide and/or peptidomimetic according to the present invention in an aqueous solution.

In one embodiment, the dissolved hydrophobic peptide and/or peptidomimetic in aqueous solution is further exposed to temperature, wherein the temperature is in the range from 20° C. to 90° C., preferably from 20° C. to 70° C.

In one embodiment, the hydrophobic peptide and/or peptidomimetic is dissolved at a concentration from 0.01 µg/ml to 100 mg/ml, preferably at a concentration from 1 mg/ml to 50 mg/ml, more preferably at a concentration from about 1 mg/ml to about 20 mg/ml.

The objects of the present invention are solved by a method of preparing a hydrogel, the method comprising dissolving a hydrophobic peptide and/or peptidomimetic according to the present invention and a hydrophobic peptide and/or peptidomimetic with a non-polar head group as defined herein in an aqueous solution.

The objects of the present invention are solved by a wound dressing or wound healing agent comprising a hydrogel according to the invention.

The objects of the present invention are solved by a surgical implant, or stent, the surgical implant or stent comprising a peptide and/or peptidomimetic scaffold, wherein the peptide and/or peptidomimetic scaffold is formed by a hydrogel according to the invention.

The objects of the present invention are solved by a pharmaceutical and/or cosmetic composition and/or a biomedical device and/or electronic device comprising the hydrophobic peptide and/or peptidomimetic according to the invention.

The objects of the present invention are solved by a pharmaceutical and/or cosmetic composition and/or a biomedical device and/or electronic device comprising the hydrophobic peptide and/or peptidomimetic of the present invention and the hydrophobic peptide and/or peptidomimetic with a non-polar head group as defined herein.

In one embodiment, the pharmaceutical and/or cosmetic composition and/or the biomedical device, and/or the electronic devices further comprises a pharmaceutically active compound.

In one embodiment, the pharmaceutical and/or cosmetic composition is provided in the form of a topical gel or cream, a spray, a powder, or a sheet, patch or membrane, or wherein the pharmaceutical and/or cosmetic composition is provided in the form of an injectable solution.

In one embodiment, the pharmaceutical and/or cosmetic composition further comprises a pharmaceutically acceptable carrier.

The objects of the present invention are solved by a kit of parts, the kit comprising a first container with a hydrophobic peptide and/or peptidomimetic according to the invention and a second container with an aqueous solution.

In one embodiment, the kit further comprises a third container with a hydrophobic peptide and/or peptidomimetic with a non-polar head group as defined herein.

In one embodiment, the aqueous solution of the second container further comprises a pharmaceutically active compound.
and/or wherein the first and/or third container with a hydrophobic peptide and/or peptidomimetic further comprises a pharmaceutically active compound.

The objects of the present invention are solved by an in vitro or in vivo method of tissue regeneration comprising the steps:
(a) providing a hydrogel according to the invention,
(b) exposing said hydrogel to cells which are to form regenerated tissue,
(c) allowing said cells to grow on said hydrogel.

In one embodiment, wherein the method is performed in vivo, in step a), said hydrogel is provided at a place in a body where tissue regeneration is intended,
wherein said step a) is preferably performed by injecting said hydrogel at a place in the body where tissue regeneration is intended.

The objects of the present invention are solved by a method of treatment of a wound and for wound healing, said method comprising the step of
applying an effective amount of a hydrogel according to the invention or a pharmaceutical composition according to the invention to a wound.

The objects of the present invention are solved by a bioimaging device comprising a hydrogel according to the invention for in vitro and/or in vivo use,
preferably for oral application, for injection and/or for topical application.

The objects of the present invention are solved by a 2D or 3D cell culture substrate comprising a hydrogel according to the invention.

BRIEF DESCRIPTION OF THE DRAWINGS

Reference is now made to the figures, wherein.

(A) These amphiphilic peptides have the characteristic motif, wherein the aliphatic amino acids are arranged in decreasing hydrophobicity from N-terminus, as exemplified by Ac-LIVAGK-NH$_2$(SEQ ID NO: 20). During self-assembly, the peptides are hypothesized to associate in an anti-parallel fashion, giving rise to α-helical intermediate structures detected by circular dichroism. (B) As the peptide concentration increases, conformational changes from random coil (black line) to α-helical intermediates (red line) to β-fibrils (blue line) are observed. The insert better illustrates the latter conformations. This phenomenon is observed for hexamers such as Ac-LIVAGK-NH$_2$ (SEQ ID NO: 20)and trimers (Ac-IVK-NH$_2$), though the transition concentration to β-fibrils is higher for the trimer. The peptide dimers subsequently stack in fibrils that aggregate into nanofibers and sheets, which entrap water to form hydrogels. c, The nanofibrous architecture, as observed using field emission scanning microscopy, resembles extracellular matrix. The fibers extend into the millimeter range. The nanofibers of hexamers such as Ac-LIVAGK-NH$_2$ (EQ ID NO: 20) (2 mg/mL) readily condense into sheets, while individual fibers are more easily observedfor Ac-IVK-NH$_2$ (15 mg/mL). The fibers form interconnected three-dimensional scaffolds which are porous.

FIG. 2. Examples of subclasses of peptides/peptidomimetics that demonstrate stimuli-responsive gelation.

Figure 3:
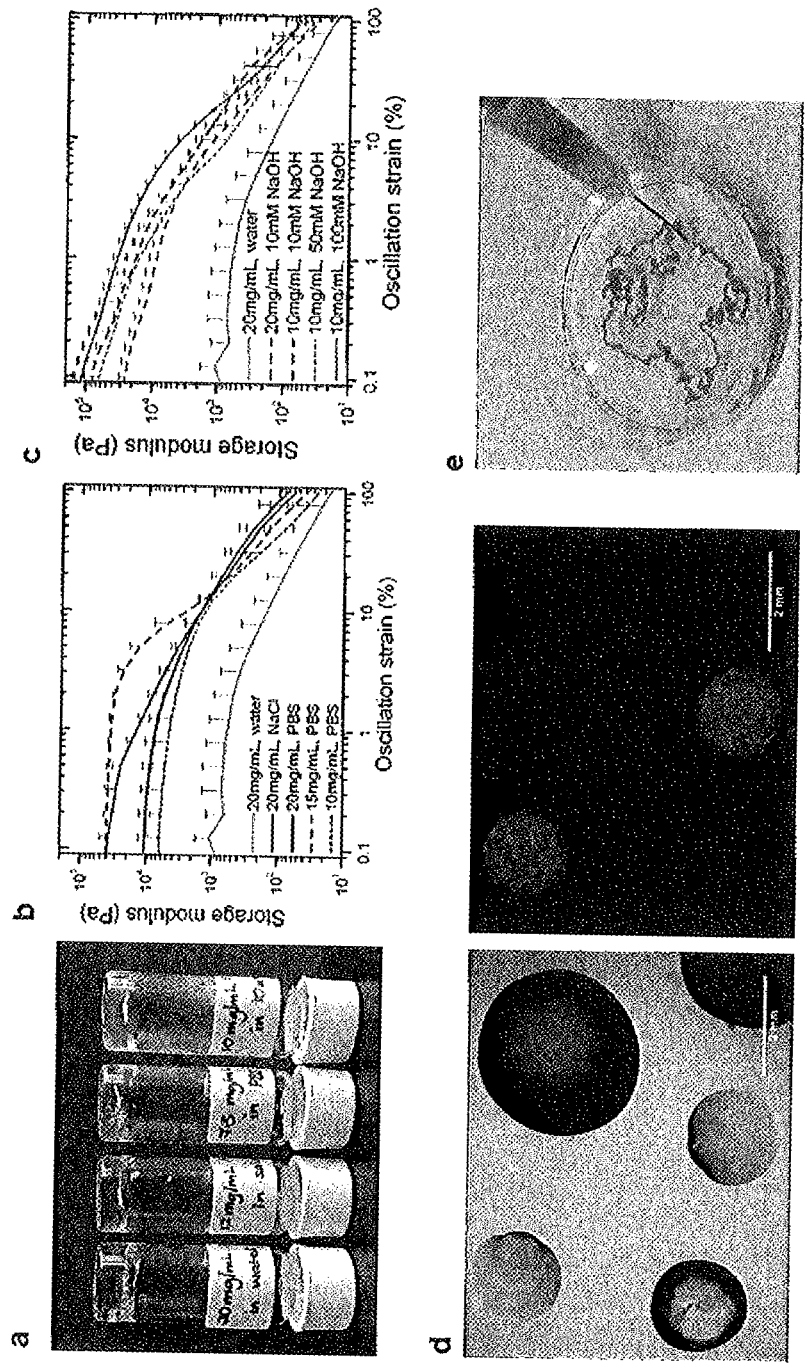

FIG. 3. Stimuli-responsive gelation of amidated peptides/peptidomimetics containing primary amine groups.

(A) A subclass of ultrashort peptides with lysine as the polar residue at the C-terminus, form hydrogels more readily in salt solutions—the minimum gelation concentration is significantly lowered and the gelation kinetics are accelerated. Ac-LIVAGK-NH$_2$ (SEQ ID NO: 20) forms hydrogels at 20 mg/mL in water, 12 mg/mL in saline, 7.5 mg/mL in PBS, and 10 mg/mL in 10 mM NaOH.(B) The rigidity, as represented by the storage modulus (G'), of 20 mg/mL Ac-LIVAGK-NH$_2$ hydrogels increases by one order of magnitude to 10 kPa when dissolved in normal saline(NaCl) as compared to water at 1 kPa. In phosphate buffered saline (PBS), G' increases to 40 kPa. The stiffness also increases with peptide concentration. (C) The addition of sodium hydroxide (NaOH) enhances the rigidity of 20 mg/mL Ac-LIVAGK-NH$_2$ (SEQ ID NO: 20) hydrogel from 1 kPa in water to 80 kPa. The rigidity increases with NaOH concentration. (D) Hydrogel droplet arrays of various dimensions can be obtained by mixing equivolumes of peptide solution (such as 10 mg/mL Ac-ILVAGK-NH$_2$)(SEQ ID NO: 20) and PBS containing small molecules. Bioactive moieties can also be encapsulated; 1 μL droplets with green food colouring and 488 nm emission quantum dots, 2 μL droplets with red food colouring and 568 nm emission fluorophore conjugated to a secondary antibody, and 5 μL droplets with methylene blue and DAPI. (E) Hydrogel "noodles" are obtained by extruding 5 mg/mL Ac-ILVAGK-NH$_2$ (SEQ ID NO: 20) solution through a 27 gauge needle into a concentrated salt bath.

Figure 4:
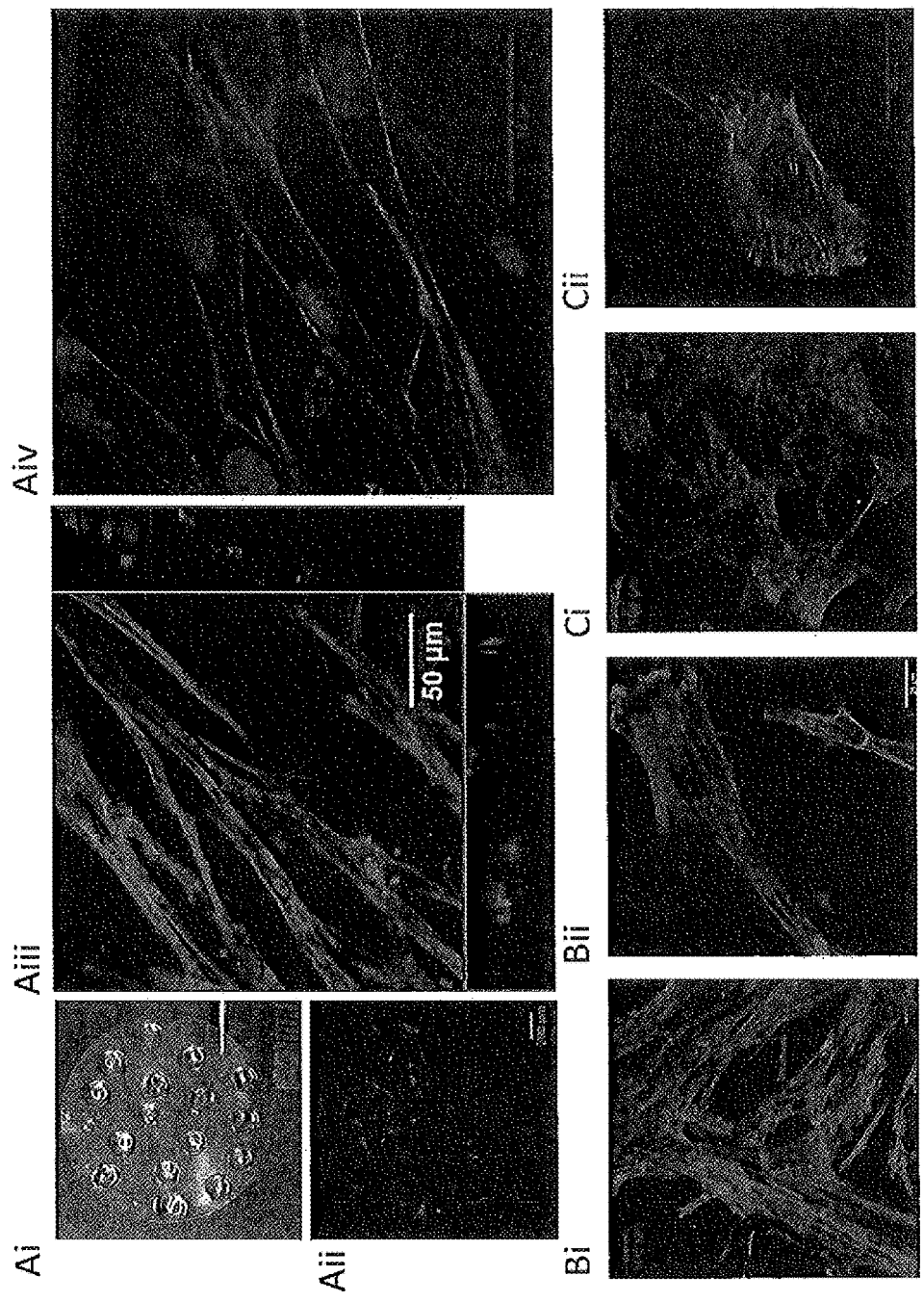

FIG. 4. The peptide hydrogels are very compatible, supporting the growth of cells in vitro. Cells can be encapsulated and immobilized within the peptide hydrogels for various applications such as induction of differentiation and screening assays.

(A) Human mesenchymal stem cells encapsulated within 2 μL droplets of 5 mg/mL Ac-IK6-NH$_2$ (SEQ ID NO: 21)hydrogels. (Ai) Photograph of mini-hydrogels on a 25 mm cover slip. (Aii) The cells encapsulated visualised using fluorescent microscopy of a single mini-hydrogel, wherein the cells are stained with Phalliodin-FITC (cytoskeleton is stained green) and Dapi (nuclei stained blue). (Aiii) The encapsulated cells adopt an elongated morphology as demonstrated in this 2D projection image at 10× magnification. The cells are located on different focal planes. (Aiv) Higher magnification image (63×) showing the focal adhesions (in red). (B) Human mesenchymal stem cells cultured on hydrogel films also adopt an elongated morphology compared to those cultured on (C) glass cover slips.

Figure 5:
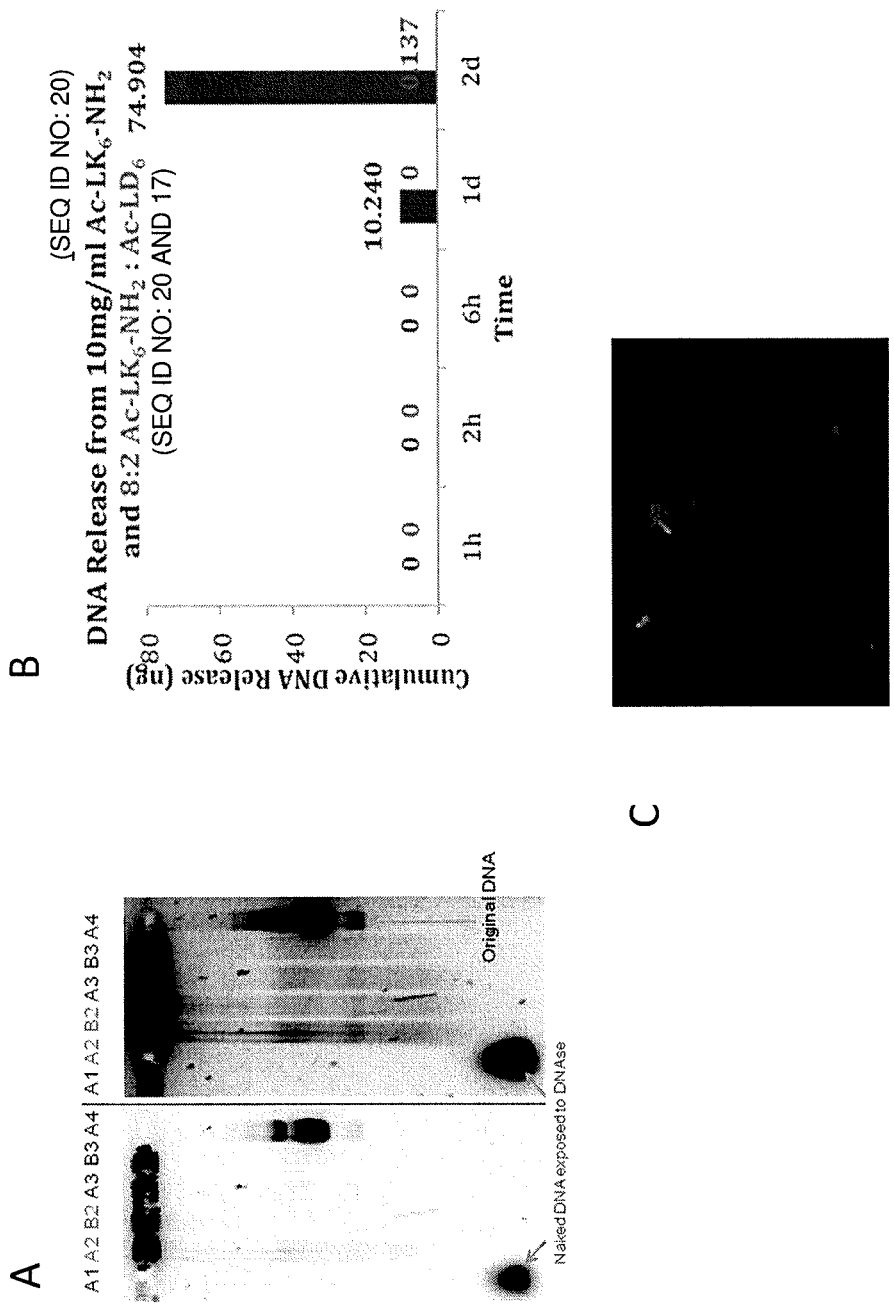

FIG. 5. Oligonucleotides such as DNA, mRNA, siRNA can be encapsulated in the hydrogels for substrate mediated gene delivery, Cells can subsequently be co-encapsulated or seeded onto these hydrogels.

(A) Hydrogels protect the oligonucleotide from nuclease degradation. (B) Hydrogels slowly release the encapsulated DNA over time. (C) Cells cultured on hydrogels encapsulating GFP mRNA express the protein of interest (GFP) after 2 days.

Figure 6:
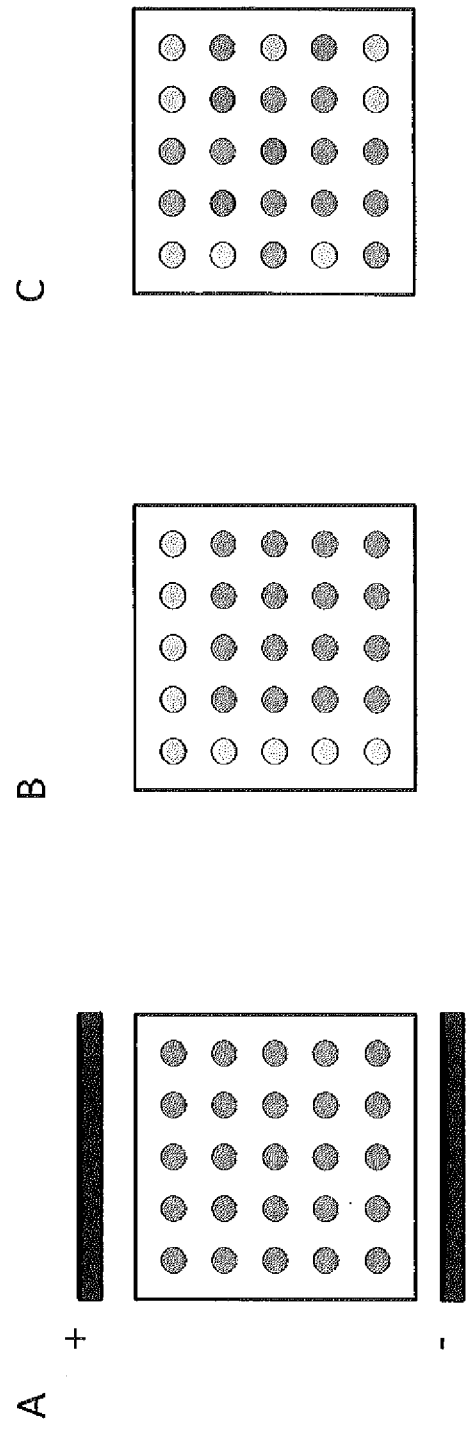

FIG. 6. 2D mini-hydrogel arrays for various applications.

Such 2D arrays can be generated using existing technology such as printers, pintools and micro-contact printing. (A) The array could be subject to electrical or magnetic stimuli, such as a electric field or point stimuli. The mini-hydrogels can also be printed onto electrical circuits or piezoelectric surfaces to conduct current. (B) Different small molecules or oligonucleotides can be encapsulated to create a biochemical gradient. (C) Different cells can be encapsulated in different mini-hydrogels and treated with the same drug/bioactive molecule dissolved in the bulk media. Alternatively, different drugs or biochemical cues can be incorporated to alter gene expression of the encapsulated cells.

Figure 7:
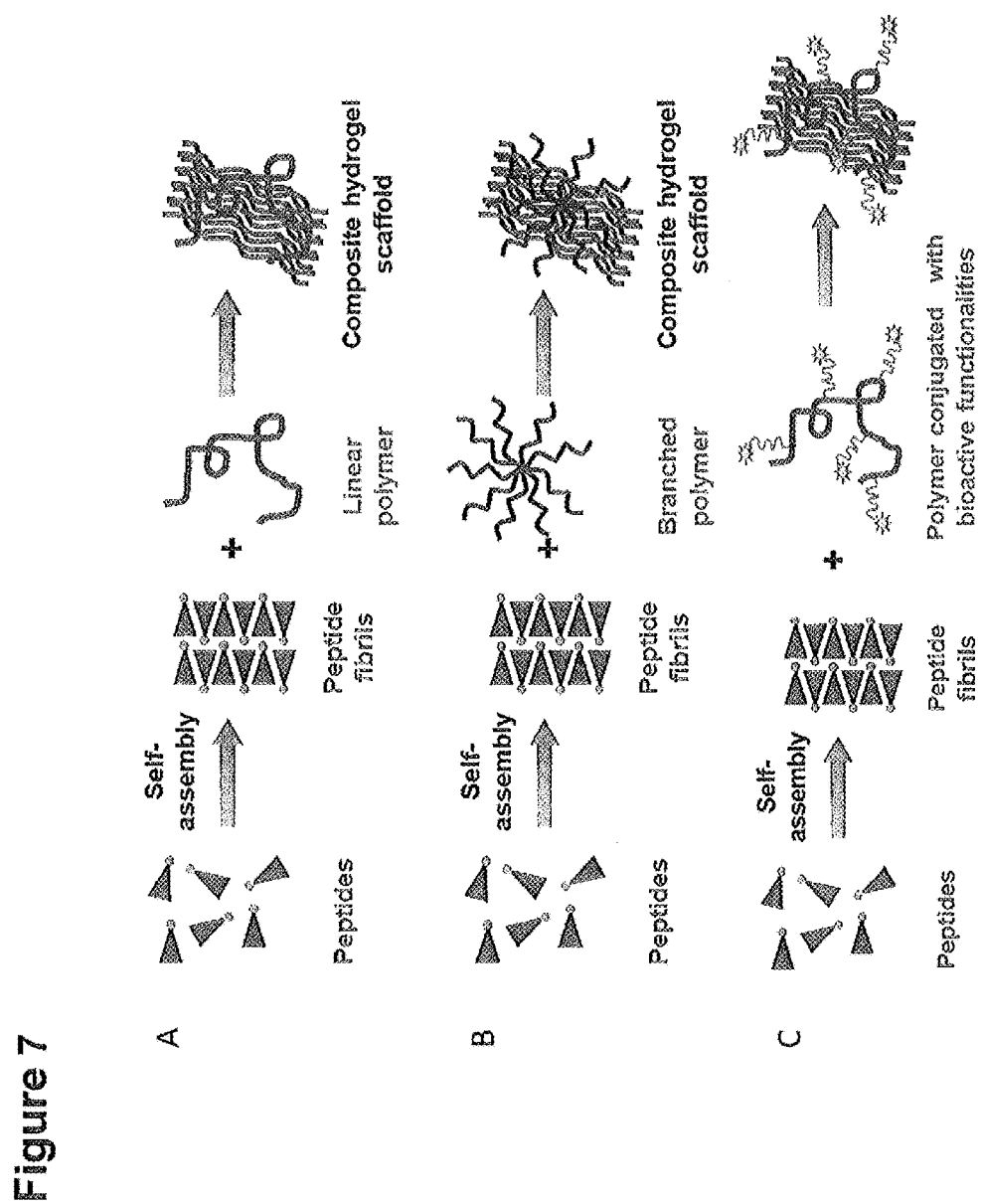

FIG. 7. The stability and mechanical properties of mini-hydrogels can also be further enhanced through the addition of cross-linkers, including short linkers, linear and branched polymers.

Such composite polymer-peptide hydrogels are produced by incorporating (A) linear and (B) branched polymers that can interact electrostatically with ultrashort peptides during self-assembly. The resulting hydrogels have better mechanical properties (due to cross-linking and increased elasticity) and (C) offer opportunities to incorporate bioactive functionalities to modulate the immune and physiological response.

Figure 8:
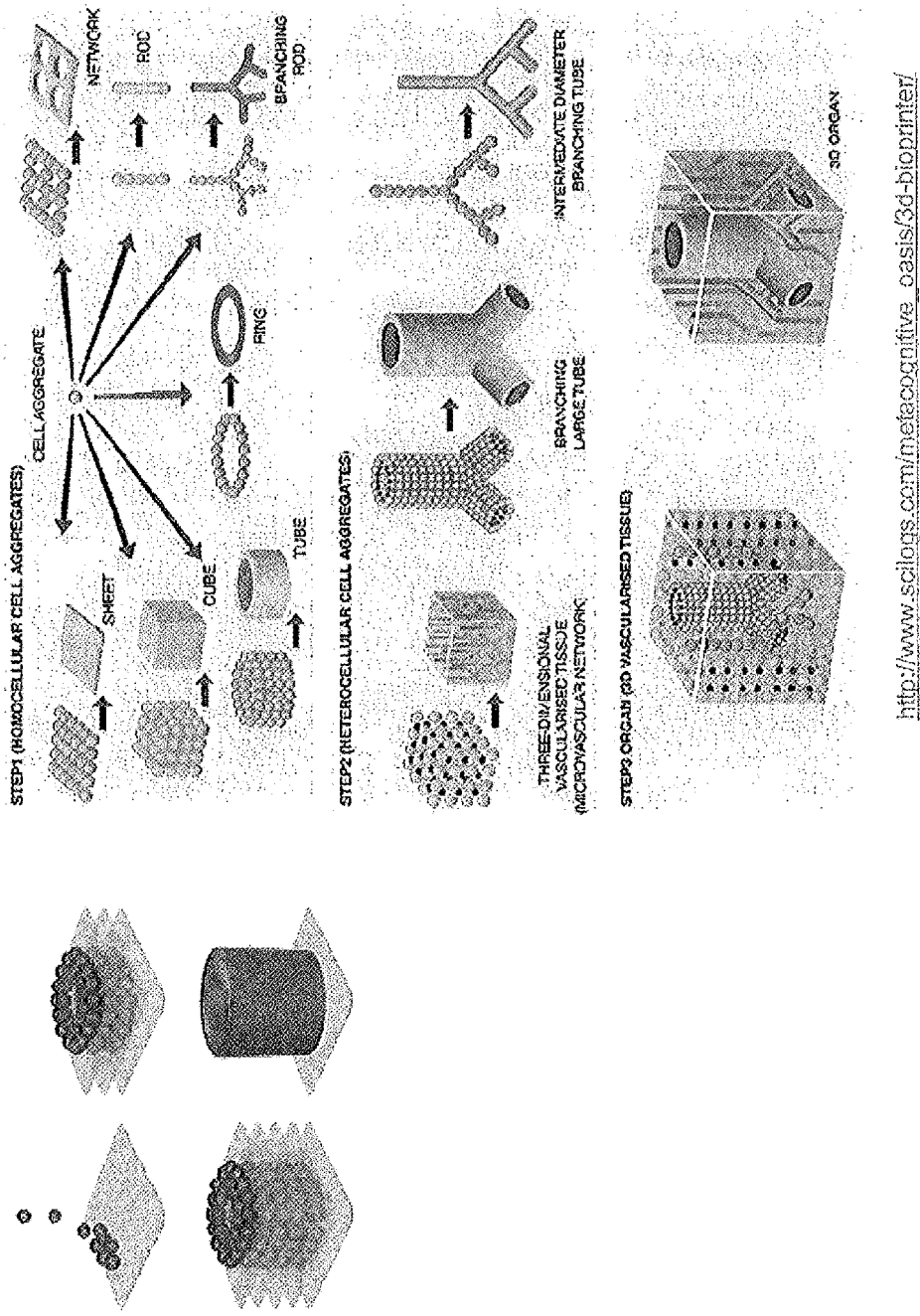

FIG. 8. 3D bio printing or moulding techniques to create biological constructs with distinct, multi-functional micro-niches.

Multi-cellular constructs can also be obtained as the hydrogel can spatially confine different cell types.

Figure 9:
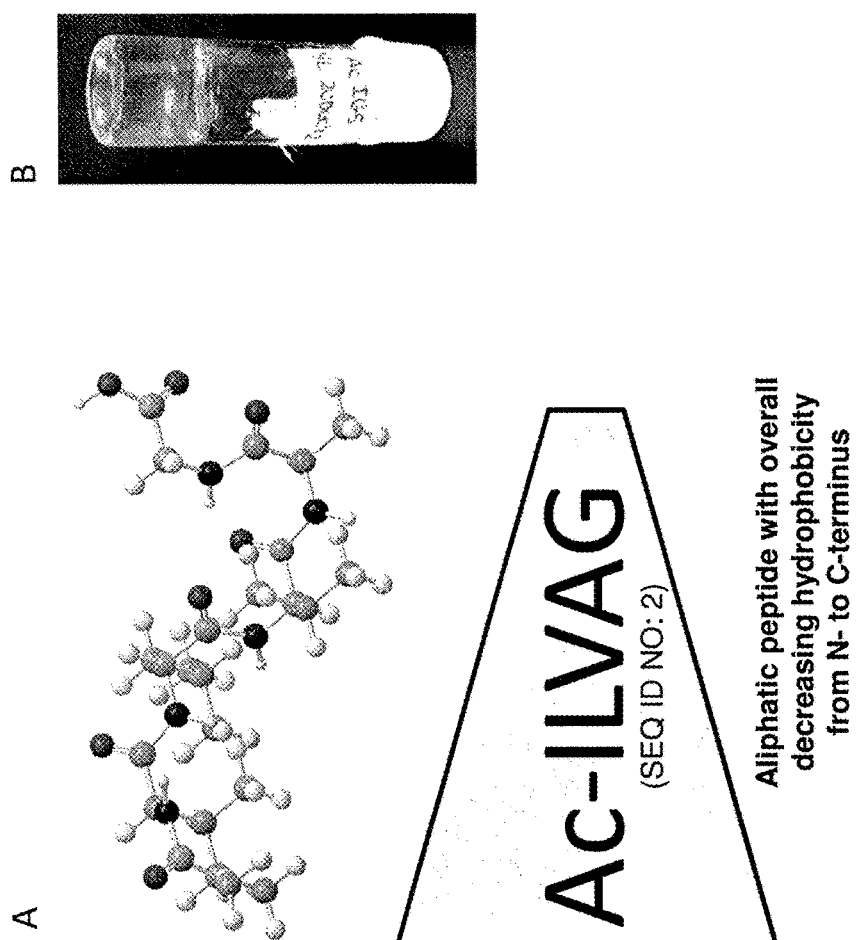

FIG. 9. A novel class of hydrophobic peptides which self-assemble into hydrogels.

(A) These hydrophobic peptides have the characteristic motif, wherein the aliphatic amino acids are arranged in decreasing hydrophobicity from N-terminus, as exemplified by Ac-ILVAG. (SEQ ID NO: 2)(B) A hydrogel comprising of peptide Ac-ILVAG (SEQ ID NO: 2) (at 5 mg/mL), which has a carboxylic acid as a polar functional group at the C-terminus.

FIG. 10. C-terminus functionalization of the hydrophobic peptides.

(A) The characteristic peptidic motif that drives self-assembly can be coupled to other functional groups, linkers and small molecules to obtain conjugates that self-assemble.

(B) FESEM images of Ac-ILVAG-biotin (SEQ ID NO: 2) reveal its nanofibrous architecture, confirming that functionalization at the C-terminus does not disrupt the nanofibrous architecture.

FIG. 11 Encapsulated H1 human embryonic stem cells proliferate and maintain their pluripotency, demonstrating that culturing in 3D preserves the native phenotype of primary cells.

(A) Pluripotency maintenance was demonstrated by confocal imaging of samples stained using primary antibodies against the relevant stem cell biomarkers.

(B) Gene expression analysis using reverse transcription quantitative PCR. 3D culture of H1 embryonic stem cells encapsulated in peptide hydrogel expressed higher levels of pluripotency markers, including the Yamanaka factors, as compared to cells cultured on Matrigel (control).

Figure 12:
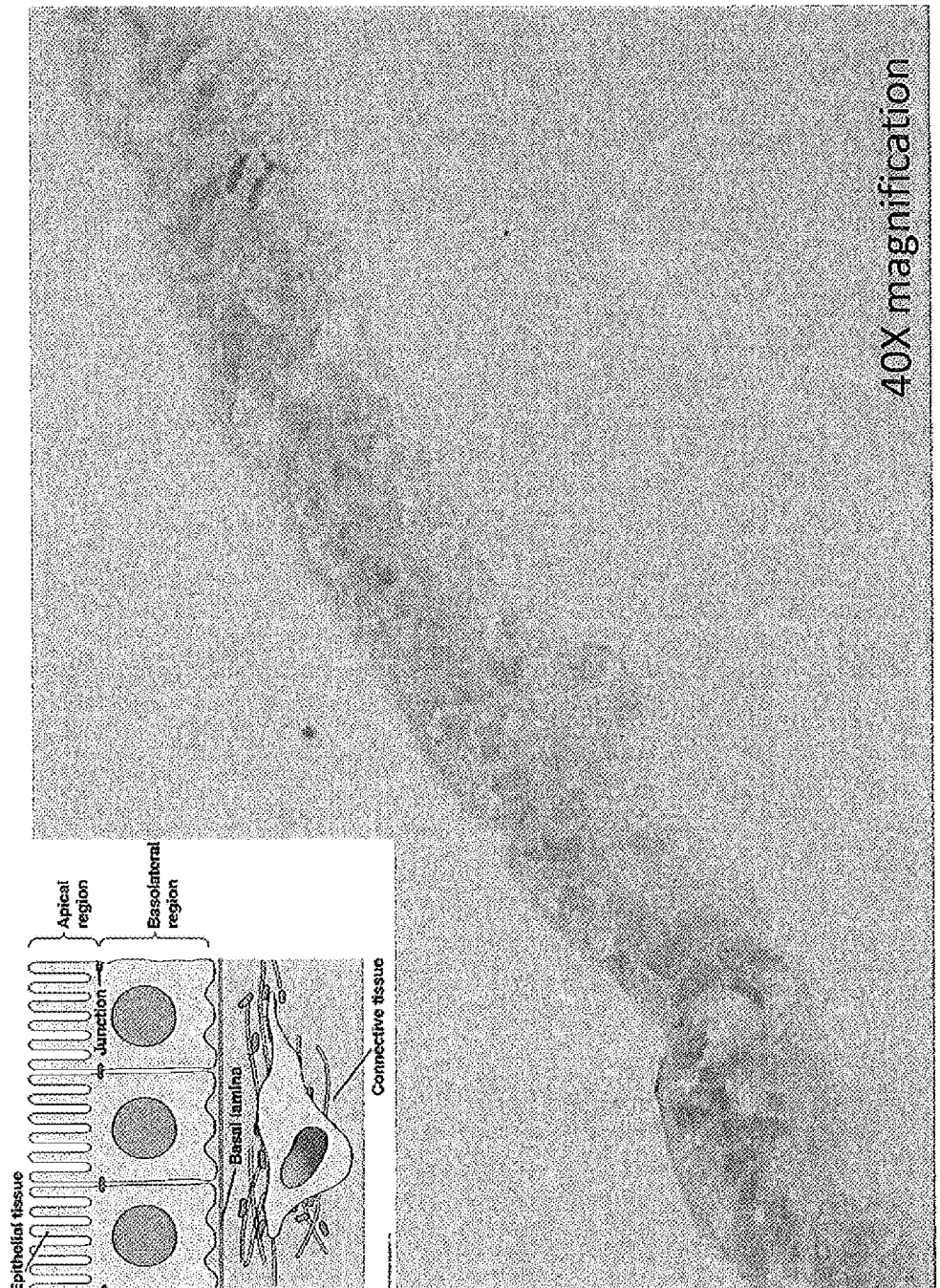

FIG. 12 Cells can also be printed onto the surface of bioprinted hydrogels. Culturing in 3D better preserves the native phenotype of primary cells and will enable cells to be culturedin higher density.

(A) Gut epithelial Caco2 cells deposited onto peptide hydrogels developed phenotypic morphological characteristics similar to native enterocytes in the gut, as observed by the presence of microvilli structures under field emission scanning electron microscopy. In comparison, cells cultured on glass cover slips do not have as confluent or prominent microvilli. Cells cultured on Corning transwell membranes were used as positive controls.

(B) Caco2 cells cultured on the hydrogel also express higher levels of apical surface receptor FUT2A (red staining), compared to constructs cultured on glass cover slips. Cells cultured on 3 μm transwell membranes serve as the positive control.

(C) Caco2 cells cultured on the hydrogel form a continuous monolayer after 21 days of culture. Their morphology is similar to cells in vivo (insert), as demonstrated by cell nuclei in in the basolateral region and microvilli structures in the apical region.

Figure 13:
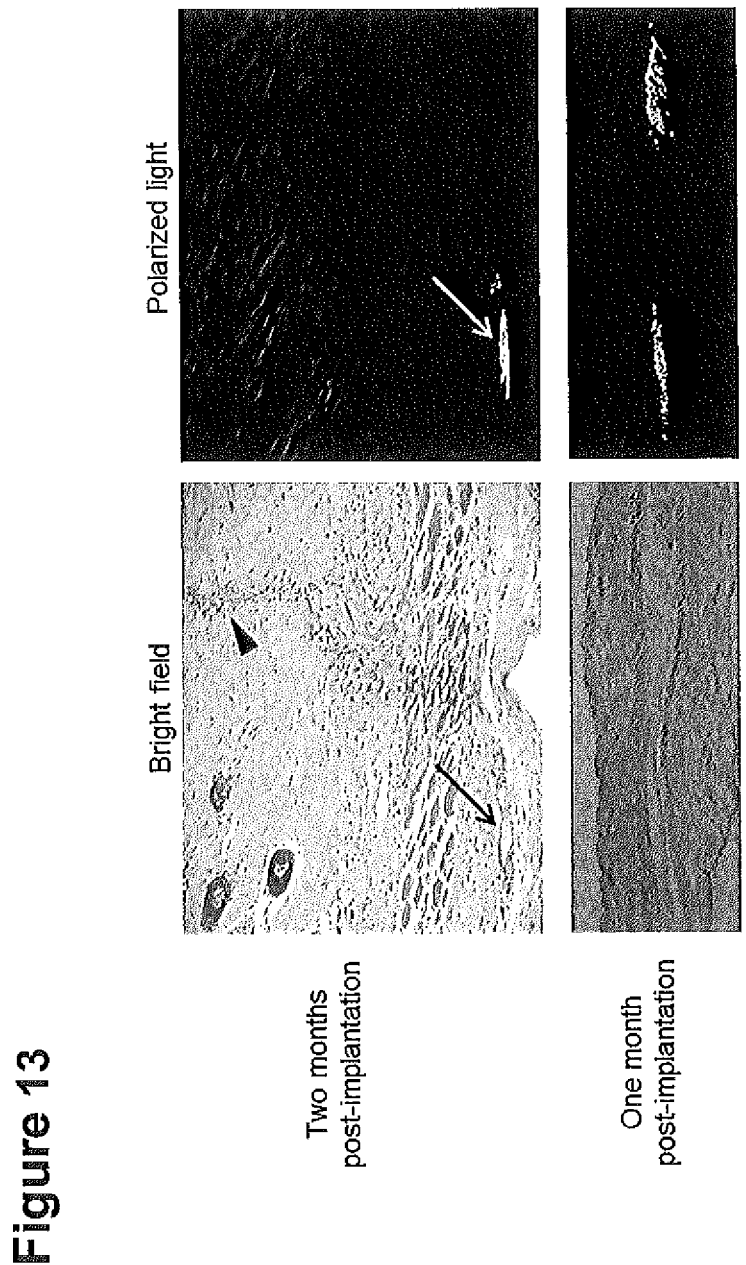

FIG. 13 The peptide hydrogels demonstrate good in vitro and in vivo biocompatibility and stability.

The in vivo bio compatibility and stability was evaluated by subcutaneous implantations of 30 μL hydrogel discs into C57BL/6 mice. Post-implantation, the hydrogels (black arrow) can still be observed as amorphous refractile material beneath the muscle layer in this typical H&E section. The hydrogels are polarizable (white arrow). The implantation surgery elicited an immune response, as evident from the inflamed tract extending from the skin epidermis to the skeletal muscle (triangle). The inflammatory response to the subcutaneous hydrogel implants was minimal to mild. A few multi-nucleated giant cell histiocytes (black arrow) were observed in the vicinity of several implants. There was no capsule formation and the hydrogel implant was partially degraded by the macrophages.

Figure 14:
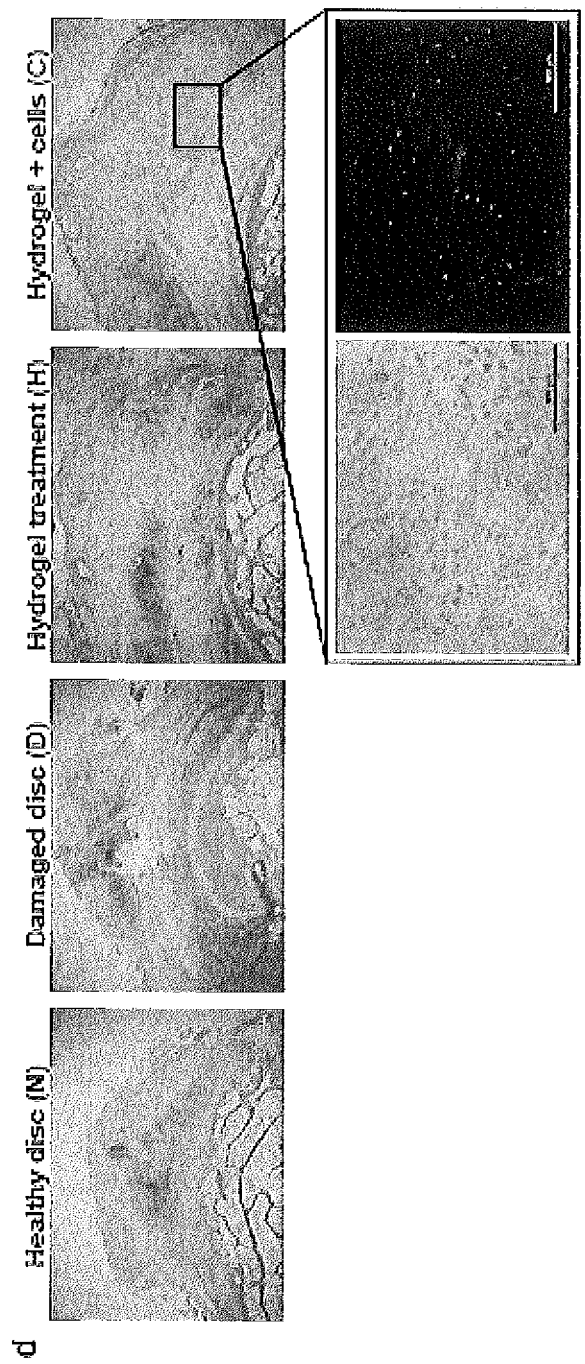

FIG. 14 Evaluation of an injectable therapy in a rabbit model of degenerative disc disease.

(A) In this animal model, three lumbar intervertebral discs between the L3 and L6 vertebrae were punctured and their nucleus pulposus (NP) content aspirated. One month post-injury, two different treatments were injected into the NP space. The first treatment consists of 20 mg/mL of Ac-LIVAGK-NH$_2$ (SEQ ID NO: 20) in PBS and gadolinium-DTPA (Gd-DTPA), a T1 MRI contrast agent. The second therapy consists of labeled donor rabbit NP cells encapsulated in 20 mg/mL of Ac-LIVAGK-NH$_2$ (SEQ ID NO: 20) in PBS. The cells were labeled with FITC-conjugated iron oxide nanoparticles, which are T2 MRI contrastophores. The remaining disc served as an untreated control.

(B) Ex vivo magnetic resonance imaging (MRI) of the sagittal section of animal R245 reveals the water content of different discs (two month post-treatment).

(C) The NP is better visualized in coronal MRI slices (animal R245). The NP (yellow triangle) of healthy discs (N) have a high water content, as demonstrated by the brighter T1 signal. In comparison, damaged untreated discs (D) are darker. The hydrogel treatment (H) significantly amplified the T1 signal, in part due to the presence of Gd-DTPA. In T2 weighted experiments, greater contrast was observed for the cell therapy samples (C), which implicates the presence of the labeled injected cells.

(D) Histology sections of different discs revealed that the hydrogel and cell treatments integrated with the tissue and did not elicit an immune response. The healthy disc was obtained from animal R245 (disc L2/L3), while the damaged disc was from R334 (L4/L5). The hydrogel treated disc imaged is L3/L4 from R245 and the cell therapy disc is L5/L6 of R328. At higher magnification, faintly fluorescent cells could be observed for discs that received cell therapy.

DETAILED DESCRIPTION OF THE INVENTION

Further Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The terms "peptoid" and "peptidomimetic" are used herein interchangeably and refer to molecules designed to mimic a peptide. Peptoids or peptidomimetics can arise either from modification of an existing peptide, or by designing similar systems that mimic peptides. These modifications involve changes to the peptide that will not occur naturally (such as altered backbones and/or the incorporation of non-natural amino acids). See above.

The term "amino acid" includes compounds in which the carboxylic acid group is shielded by a protecting group in the form of an ester (including an ortho ester), a silyl ester, an amide, a hydrazide, an oxazole, an 1,3-oxazoline or a 5-oxo-1,3,-oxazolidine. The term "amino acid" also includes compounds in which an amino group of the form —NH$_2$ or —NHR' (supra) is shielded by a protecting group. Suitable amino protecting groups include, but are not limited to, a carbamate, an amide, a sulfonamide, an imine, an imide, histidine, a N-2,5,-dimethylpyrrole, an N-1,1,4,4-tetramethyldisilylazacyclopentane adduct, an N-1,1,3,3-tetramethyl-1,3-disilisoindoline, an N-diphenylsilyldiethylene, an 1,3,5-dioxazine, a N-[2-(trimethylsilyl)ethoxy]methylamine, a N-(5,5-dimethyl-3-oxo-1-cyclohexenyl)amine, a N-4,4,4-trifluoro-3-oxo-1-butenylamine, a N-9-borabicyclononane and a nitroamine. A protecting group may also be present that shields both the amino and the carboxylic group such as e.g. in the form of a 2,2-dimethyl-4-alkyl-2-sila-5-oxo-1,3-oxazolidine. The alpha carbon atom of the amino acid typically further carries a hydrogen atom. The so called "side chain" attached to the alpha carbon atom, which is in fact the continuing main chain of the carboxylic acid, is an aliphatic moiety that may be linear or branched. The term "side chain" refers to the presence of the amino acid in a peptide (supra), where a backbone is formed by coupling a plurality of amino acids. An aliphatic moiety bonded to the α carbon atom of an amino acid included in such a peptide then defines a side chain relative to the backbone. As explained above, the same applies to an aliphatic moiety bonded to the amino group of the amino acid, which likewise defines a side chain relative to the backbone of a peptoid.

The term "aliphatic" means, unless otherwise stated, a straight or branched hydrocarbon chain, which may be saturated or mono- or poly-unsaturated and include heteroatoms. The term "heteroatom" as used herein means an atom of any element other than carbon or hydrogen. An unsaturated aliphatic group contains one or more double and/or triple bonds (alkenyl or alkynyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to 5, to 10, to 15 or to 20 carbon atoms. Examples of alkenyl radicals are straight-chain or branched hydrocarbon radicals which contain one or more double bonds. Alkenyl radicals generally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, preferably such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3,3 dimethylbutyl. Both the main chain as well as the branches may furthermore contain heteroatoms as for instance N, O, S, Se or Si or carbon atoms may be replaced by these heteroatoms.

An aliphatic moiety may be substituted or unsubstituted with one or more functional groups. Substituents may be any functional group, as for example, but not limited to, amino, amido, azido, carbonyl, carboxyl, keto, cyano, isocyano, dithiane, halogen, hydroxyl, nitro, organometal, organoboron, seleno, silyl, silano, sulfonyl, thio, thiocyano, trifluoromethyl sulfonyl, p-toluenesulfonyl, bromobenzenesulfonyl, nitrobenzenesulfonyl, and methanesulfonyl.

As should be apparent from the above, the side chain of an amino acid in a peptide/peptoid described herein may be of a length of 0 to about 5, to about 10, to about 15 or to about 20 carbon atoms. It may be branched and include unsaturated carbon-carbon bonds. In some embodiments one or more natural amino acids are included in the peptide or peptoid. Such a natural amino acid may be one of the 20 building blocks of naturally occurring proteins.

In a peptide or peptoid, including a peptide/peptoid disclosed herein individual amino acids are covalently coupled via amide bonds between a carboxylic group of a first and an amino group of a second amino acid.

The term amphiphilic refers to a compound that is soluble in both polar and non-polar fluids. It also encompasses multiphase compounds. The amphiphilic properties of the peptide and/or peptoid are due to the presence of both polar and non-polar moieties within the same peptide and/or peptoid. In this regard the peptide and/or peptoid may be of surfactant nature.

Accordingly, the polar properties of a peptide and/or peptoid disclosed herein are based on a polar moiety. Two such moieties are a —COOH side group, in particular in the form of a charged COO⁻ group and an amino group. A further such moiety is a C-terminal —COOH group if it is present in free, unprotected form. Generally, a surfactant molecule includes a polar, typically hydrophilic, head group attached to a non-polar, typically hydrocarbon, moiety. Non-polar moieties of a peptide or peptoid include a hydrocarbon chain that does not carry a functional group.

An amphiphilic linear sequence included in a peptide and/or peptoid disclosed herein thus includes a polar moiety and a non-polar moiety. The polar moiety includes an aliphatic amino acid that carries a polar group such as a hydroxyl group, a thiol group, a seleno group, an amino group, an amide group, an ether group, a thioether group or a seleno ether group. Accordingly, the polar moiety may include an amino acid that carries a functional polar group with a proton such as hydroxyl, thiol, selenol, amine or amide. The polar moiety may also include the C-terminus or the N-terminus of the peptide and/or peptoid. The C-terminus or the N-terminus may in such a case be present in the form of the free carboxyl or amino group, respectively, i.e. free of a protecting group.

Generally the polar moiety of a linear amphiphilic sequence of an amphiphilic peptide and/or peptoid disclosed herein is defined by a single amino acid, by two consecutive amino acids or by three consecutive amino acids that is/are coupled to the non-polar moiety of the peptide/peptoid. Accordingly, in some embodiments the polar moiety of the peptide/peptoid consists of two amino acids that are covalently coupled via an amide bond, both amino acids carrying a polar peptide/peptoid side chain. One of these two amino acids may be a terminal amino acid of the peptide/peptoid, defining its N— or C-terminus. In some embodiments the amphiphilic peptide/peptoid has a single amino acid with a polar side chain with the residual portion of the peptide/peptoid defining the non-polar moiety. In some embodiments the amphiphilic peptide/peptoid has two amino acids with a polar side chain while the residual portion of the peptide/peptoid defines the non-polar moiety. As three illustrative examples of a respective polar side chain may serve 4-methyl-4-thio-pentyl, 6-ethoxycarbonyl-4,5-dimethyl-hexyl and 6-hydroxy-4-(1-hydroxyethyl)-hexyl groups. As used herein, the numbering of corresponding peptide/peptoid side chains is started with "1" at the carbon atom that is covalently bonded to the α-carbon atom of the amino acid or to the amino group of the amino acid, respectively. Amino acids included in the polar moiety may be or include, but are not limited to, aspartic acid, asparagine, glutamic acid, 4-fluoro-glutamic acid, 2-aminoadipic acid, γ-carboxy-glutamic acid, 4-tert-butyl aspartic acid, glutamine, 5-N-ethyl-glutamine (theanine), citrulline, thio-citrulline, cysteine, homocysteine, methionine, ethionine, selenomethionine, telluromethionine, threonine, allo-threonine, serine, homoserine, arginine, homoarginine, ornithine, lysine, 5-hydroxy-lysine and N(6)-carboxymethyllysine. Any such amino acid may be present in the L- or D-form.

The amphiphilic linear sequence of the amphiphilic peptide/peptoid disclosed herein can be defined as having n amino acids. Where a single amino acid with a polar side chain is included in the amphiphilic linear sequence, the non-polar moiety may then be taken to have n−1 amino acids. In this case the polar moiety consists of exactly one amino acid, such amino acid being selected from any amino acids of the foregoing paragraph. Where two consecutive amino acids with a polar side chain are included in the amphiphilic linear sequence of the peptide/peptoid, the non-polar moiety may then be taken to have n−2 amino acids. In this case the polar moiety consists of exactly two amino acids. Where three consecutive amino acids with a polar side chain are included in the amphiphilic linear sequence, the non-polar moiety may then be taken to have n−3 amino acids. In this case the polar moiety consists of exactly three amino acids. In embodiments where the polar moiety consists of two amino acids, the polar moiety may have a sequence selected from Asn-Asn, Asp-Asp, Glu-Glu, Gln-Gln, Asn-Gln, Gln-Asn, Asp-Gln, Gln-Asp, Asn-Glu, Glu-Asn, Asp-Glu, Glu-Asp, Gln-Glu, Glu-Gln, Asp-Asn, Asn-Asp, Thr-Thr, Ser-Ser, Thr-Ser, Ser-Thr, Asp-Ser, Ser-Asp, Ser-Asn, Asn-Ser, Gln-Ser, Ser-Gln, Glu-Ser, Ser-Glu, Asp-Thr, Thr-Asp, Thr-Asn, Asn-Thr, Gln-Thr, Thr-Gln, Glu-Thr, Thr-Glu. In embodiments where the polar moiety consists of three amino acids, the polar moiety may have a sequence selected from Asn-Asn-Asn, Asn-Asn-Asp, Asn-Asp-Asn, Asp-Asn-Asn, Asp-Asp-Asn, Asp-Asn-Asp, Asp-Asp-Asp, Asn-Asn-Glu, Asn-Asn-Gln, Asn-Glu-Asn, Asn-Gln-Asn, Glu-Glu-Glu, Gln-Gln-Gln, Asn-Gln-Gln, Asn-Glu-Gln, Asp-Asn-Glu, Gln-Asn-Asn, Gln-Asn-Asn, Glu-Asp-Gln, Asp-Gln-Asp, Asn-Glu-Asp, Glu-Asn-Gln, Asp-Glu-Gln, Asn-Glu-Gln, Glu-Asp-Asn, and Gln-Asp-Asn, Thr-Thr-Thr, Ser-Ser-Ser, Asn-Thr-Thr, Asn-Ser-Ser Asn-Ser-Thr, Asn-Thr-Ser Asp-Asn-Ser, Ser-Asn-Asn, Thr-Asn-Asn, Ser-Asp-Thr, to name a few.

The amphiphilic linear sequence of the peptide/peptoid has a net charge at physiological pH. The term "physiological pH" is known to those in the art to refer to the pH value of blood, which has typically a pH value of about 7.4. In embodiments where the amphiphilic linear sequence is arranged at the C- or N-terminus of the peptide/peptoid, the respective terminus may provide the corresponding net charge. In embodiments where the amphiphilic linear sequence is not arranged at the C- or N-terminus of the peptide/peptoid, the polar moiety of the amphiphilic linear sequence includes one or more amino acids that have a side chain with a functional group that is charged at physiological pH. Illustrative examples of a respective functional group include an amino, a nitro-, a guanidino, a esteryl, a sulfonyl or a carboxyl group. In some embodiments the net charge of the amphiphilic linear sequence is, as a positive or negative charge, equal to or smaller than the number of amino acids included in the polar moiety thereof. In some embodiments the net charge of the amphiphilic linear sequence is one of −3, −2 or −1. In some embodiments the net charge of the amphiphilic linear sequence is one of +1, +2 or +3.

The respective polar side chain of an amino acid of the polar moiety, coupled to the α-carbon atom of the amino acid (supra) and/or to the amino group thereof, may typically be defined by a main chain that includes 1 to about 20, including 1 to about 15, 1 to about 10 or 1 to about 5 carbon atoms. For sake of clarity it is recited that the term "side chain" is used relative to the backbone of the peptide and/or peptoid. This peptide and/or peptoid side chain may be branched and thus be defined by a main chain and branches. Both the main chain and branches, if present, of the peptide and/or peptoid side chain may include one or more double or triple bonds (supra). Examples of side chains include, but are not limited to, methyl, ethyl, propyl, isopropyl, propenyl, propinyl, butyl, butenyl, sec-butyl, tert-butyl, isobutyl, pentyl, neopentyl, isopentyl, pentenyl, hexyl, 3,3 dimethylbutyl, heptyl, octyl, nonyl or decyl groups. The functional polar group is bonded to this the peptide and/or peptoid side chain.

In some embodiments the polar moiety of the amphiphilic linear sequence includes two identical amino acids. Where these amino acids are naturally occurring amino acids, they may for example define one of the sequences Lys-Lys, Gln-Gln, Glu-Glu, Asp-Asp, Asn-Asn, Met-Met, Thr-Thr, Arg-Arg or Ser-Ser. The term "naturally occurring" in this context refers to the 20 amino acids into which the genetic code is directly being translated by any organism. Such two identical polar amino acids may for example be adjacent to the non-polar moiety. In some embodiments the amphiphilic linear sequence of the peptide/peptoid has a hydrophobic tail of aliphatic amino acids and at least one polar, including a charged, amino acid head group.

The non-polar moiety includes an amino acid, generally at least two amino acids, with a hydrocarbon chain that does not carry a functional group. The respective side chain, coupled to the α-carbon atom of the amino acid (supra), may have a main chain that includes 0 to about 20 or 1 to about 20, including 0 to about 15, 1 to about 15, 0 to about 10, 1 to about 10, 1 to about 5 or 0 to about 5 carbon atoms. The non-polar moiety may thus include an amino acid without side chain, i.e. glycine. The peptide and/or peptoid side chain may be branched (supra) and include one or more double or triple bonds (supra). Examples of peptide and/or peptoid side chains include, but are not limited to, methyl, ethyl, propyl, isopropyl, propenyl, propinyl, butyl, butenyl, sec-butyl, tert-butyl, isobutyl, pentyl, neopentyl, isopentyl, pentenyl, hexyl, 3,3 dimethylbutyl, heptyl, octyl, nonyl or decyl groups. As a few illustrative examples, the non-polar moiety may include an amino acid of alanine, valine, leucine, isoleucine, norleucine, norvaline, 2-(methylamino)-isobutyric acid, 2-amino-5-hexynoic acid. Such an amino acid may be present in any desired configuration. Bonded to the non-polar moiety may also be the C-terminus or the N-terminus of the peptide/peptoid. Typically the C-terminus or the N-terminus is in such a case shielded by a protecting group (supra).

In some embodiments the non-polar moiety includes a sequence of amino acids that is arranged in decreasing or increasing size. Hence, a portion of the amino acids of the non-polar moiety may be arranged in a general sequence of decreasing or increasing size. Relative to the direction from N- to C-terminus or from C- to N-terminus this general sequence can thus betaken to be of decreasing size. By the term "general sequence" of decreasing or increasing size is meant that embodiments are included in which adjacent amino acids are of about the same size as long as there is a general decrease or increase in size. Within a general sequence of decreasing size the size of adjacent amino acids of the non-polar moiety is accordingly identical or smaller in the direction of the general sequence of decreasing size. In some embodiments the general sequence of decreasing or increasing size is a non-repetitive sequence.

As an illustrative example, where a respective portion of amino acids is a sequence of five amino acids, the first amino acid may have a 3,4-dimethyl-hexyl side chain. The second amino acid may have a neopentyl side chain. The third amino acid may have a pentyl side chain. The fourth amino acid may have a butyl side chain. The fifth amino acid may be glycine, i.e. have no side chain. Although a neopently and a pentyl side chain are of the same size, the general sequence of such a non-polar peptide portion is decreasing in size. As a further illustrative example of a general sequence of decreasing size in. a non-polar moiety the respective non-polar portion may be a sequence of three amino acids. The first amino acid may have an n-nonyl side chain. The second amino acid may have a 3-ethyl-2-methyl-pentyl side chain. The third amino acid may have a tert-butyl side chain. As yet a further illustrative example of a general sequence of decreasing size in a non-polar moiety, the non-polar moiety may be a sequence of nine amino acids. The first amino acid may have a 4-propyl-nonyl side chain. The second amino acid may have an n-dodecyl side chain. The third amino acid may have a 6,6-diethyl-3-octenyl side chain. An n-dodecyl side chain and a 6,6-diethyl-3-octenyl side chain both have 12 carbon atoms and thus again have a comparable size, Nevertheless, the 6,6-diethyl-3-octenyl group includes an unsaturated carbon-carbon bond and is thus of slightly smaller size than the dodecyl group. The fourth amino acid may have a 2-methyl-nonyl side chain. The fifth amino acid may have a 3-propyl-hexyl side chain. The sixth amino acid may have an n-hexyl side chain. The seventh amino acid may have a 2-butynyl side chain. The 8th amino acid may have an isopropyl side chain. The ninth amino acid may have a methyl side chain.

Where a portion of the amino acids of the non-polar moiety arranged in a general sequence of decreasing (or increasing) size only contains naturally occurring amino acids (whether in the D- or the L-form), it may for example have a length of five amino acids, such as the sequence leucine-isoleucine-valine-alanine-glycine or isoleucine-leucine-valine-alanine-glycine, A general sequence of decreasing size of only natural amino acids may also have a length of four amino acids. Illustrative examples include the sequences isoleucine-leucine-valine-alanine, leucine-isoleucine-valine-alanine, isoleucine-valine-alanine-glycine, leucine-valine-alanine-glycine, leucine-isoleucine-alanine-glycine, leucine-isoleucine-valine-glycine, isoleucine-leucine-alanine-glycine or isoleucine-leucine-valine-glycine. A general sequence of decreasing size of only natural amino acids may also have a length of three amino acids. Illustrative examples include the sequences isoleucine-valine-alanine, leucine-valine-alanine, isoleucine-valine-glycine, leucine-valine-glycine, leucine-alanine-glycine, isoleucine-alanine-glycine or isoleucine-leucine-alanine. A general sequence of decreasing size of only natural amino acids may also have a length of two amino acids. Illustrative examples include the sequences isoleucine-valine, leucine-valine, isoleucine-alanine, leucine-alanine, leucine-glycine, isoleucine-glycine, valine-alanine, valine-glycine or alanine-glycine.

In some embodiments the direction of decreasing size of the above defined general sequence of decreasing size is the direction toward the polar moiety of the amphiphilic linear sequence. Accordingly, in such embodiments the size of adjacent amino acids within this portion of the non-polar moiety is accordingly identical or smaller in the direction of the polar moiety. Hence, as a general trend in such an embodiment, the closer to the polar moiety of the amphiphilic linear sequence, the smaller is the overall size of a peptide and/or peptoid side chain throughout the respective general sequence of decreasing size. In the above illustrative example of a general sequence of three amino acids with a n-nonyl, a 3-ethyl-2-methyl-pentyl and a tert-butyl side chain, the next amino acid may be polar in that it carries a peptide/peptoid side chain with a polar functional group. As an illustrative example, adjacent to the tert-butyl side chain within the peptide/peptoid there may be a 3-carboxy-n-butyl side chain.

In some embodiments the entire non-polar moiety of the amphiphilic linear peptide and/or peptoid or the amphiphilic linear sequence, respectively, consists of the general sequence of decreasing (or increasing) size. In such an embodiment the general sequence of decreasing (or increasing) size may have a length of n–m amino acids (cf. above). In some embodiments the general sequence of decreasing or increasing size is flanked by further non-polar side chains of the peptide/peptoid. In one embodiment the general sequence of decreasing (or increasing) size has a length of n−m−1 amino acids. In this embodiment there is one further amino acid included in the peptide/peptoid, providing a non-polar peptide/peptoid side chain. This amino acid may be positioned between the general sequence of decreasing (or increasing) size and the polar amino acid, the polar amino acid may be positioned between this additional non-polar amino acid and the general sequence of decreasing (or increasing) size or the general sequence of decreasing (or increasing) size may be positioned between the polar amino acid and this additional non-polar amino acid. Typically the general sequence of decreasing (or increasing) size is positioned between the polar amino acid and this additional non-polar amino acid. The additional non-polar amino acid may for example define the N-terminus of the peptide/peptoid, which may be shielded by a protecting group such as an amide, e.g. a propionic acyl or an acetyl group. Together with the general sequence of decreasing (or increasing) size as defined above it may define the non-polar portion of the peptide/peptoid. The polar amino acid may define the C-terminus of the peptide/peptoid. In this example the general sequence of decreasing (or increasing) size is thus flanked by the polar amino acid on one side and by the additional non-polar amino acid on the other side. In one embodiment where embodiment the general sequence of decreasing (or increasing) size has a length of n−m−1 amino acids, the remaining non-polar amino acid of the non-polar moiety of n-m amino acids is one of alanine and glycine.

As explained above, the polar moiety of the amphiphilic linear sequence may in some embodiments be defined by two or three consecutive amino acids. The polar moiety includes in aliphatic amino acids. Each of the in aliphatic amino acids is independently selected and carries an independently selected polar group. The symbol m represents an integer selected from 1, 2 and 3. The at least essentially non-polar moiety (supra) accordingly has a number of n−m, i.e. n−1, n−2 or n−3 amino acids. In some embodiments n is equal to or larger than m+2. In such an embodiment m may thus represent a number of n−2 or smaller.

In an embodiment where the entire non-polar moiety of the amphiphilic linear peptide and/or peptoid consists of the general sequence of decreasing (or increasing) size (supra), this non-polar moiety may thus have a length of n−2 or n−3 amino acids. In an embodiment where the amphiphilic linear peptide and/or peptoid has a further non-polar side chain in addition to the non-polar moiety of decreasing (or increasing) size, this additional non-polar side chain may be included in an amino acid that is directly bonded to an amino acid of the general sequence of decreasing (or increasing) size. The non-polar moiety may thus be defined by the non-polar moiety of decreasing (or increasing) size and the respective further amino acid with a non-polar side chain. In one such an embodiment where m=1, the non-polar moiety may thus have a length of n−2 amino acids, of which the non-polar moiety of decreasing (or increasing) size has a length of n−3 amino acids. The general sequence of decreasing (or increasing) size may be positioned between the two polar amino acids and this additional non-polar amino acid, or the additional non-polar amino acid may be positioned between the general sequence of decreasing (or increasing) size and the two polar amino acids. Typically the general sequence of decreasing (or increasing) size is positioned between the two polar amino acids and this additional non-polar amino acid. As mentioned above, one of the two polar amino acids may define the C-terminus of the peptide/peptoid. In this example the general sequence of decreasing (or increasing) size may thus be flanked by the two consecutive polar amino acids on one side and by the additional non-polar amino acid on the other side. Again, in some embodiments where m=1 the two consecutive polar amino acids may also be positioned between the general sequence of decreasing (or increasing) size and the additional non-polar amino acid, in which case the non-polar moiety has a first portion with a length of n−3 amino acids and a further portion of one amino acid.

Electrostatic forces, hydrogen bonding and van der Waals forces between amphiphilic linear sequences as defined above, including amphiphilic linear peptides and/or peptoids, result in these amphiphilic linear sequences to be coupled to each other. Without being bound by theory, thereby a cross-linking effect occurs that allows the formation of a hydrogel. In this regard the inventors have observed the formation of fibers based on helical structures.

The fibers formed of amphiphilic linear sequences of amphiphilic peptides and/or peptoids disclosed herein typically show high mechanical strength, which renders them particularly useful in tissue regeneration applications, for instance the replacement of damaged tissue. Amphiphilic peptides and/or peptoids disclosed herein have been observed to generally assemble into a fiber structure that resembles collagen fibers. Collagen, a component of soft tissue in the animal and human body, is a fibrous protein that provides most of the tensile strength of tissue. The mechanical strength of fibers of amphiphilic peptides and/or peptoids disclosed herein has been found to typically be much higher than that of collagen (cf. e.g. Figures) of gelatine, the hydrolysed form of collagen. An amphiphilic peptide and/or peptoid disclosed herein may thus be included in a hydrogel that is used as permanent or temporary prosthetic replacement for damaged or diseased tissue.

The amphiphilic linear sequence of the peptide/peptoid, which may represent the entire amphiphilic peptide/peptoid (supra) has been found to show remarkable stability at physiological conditions, even at elevated temperatures. It is in some embodiments stable in aqueous solution at physiological conditions at ambient temperature for a period of time in the range from 1 day to 1 month or more. It may in some embodiments be stable in aqueous solution at physiological conditions at 90° C. for at least 1 hour, at least 2 hours, at least 3 hours, at least 4 hours or at least 5 hours An amphiphilic linear sequence of an amphiphilic peptide and/or peptoid including an amphiphilic linear peptide and/or peptoid, is capable of providing a self assembling α-helical fiber in aqueous solution under physiological conditions. The peptides/peptoids (typically 3-7-mers) in the L- or D-form can self assemble into supramolecular helical fibers which are organized into mesh-like structures mimicking biological substances such as collagen. It has previously been observed in X-ray crystallography that peptides of a length of 3 to 6 amino acids with repetitive alanine containing sequences and an acetylated C-terminus take a helical conformation (Hatakeyama, Y, et al, Angew. Chem. Int. Ed. (2009) 8695-8698). Using peptides with an amphiphilic sequence, Ac-LD$_6$ (L), the formation of aggregates has for example been observed already at 0.1 mg/ml. As the concentration of peptide is increased to 1 mg/ml, the peptide monomers were found to align to form fibrous structures. With a formation of fibers occurring under physiological conditions at concentrations below 2 mM a peptide/peptoid is well suited as an injectable hydrogel material that can form a hydrogel under physiological conditions. Also disclosed herein is an amphiphilic linear peptide and/or peptoid as defined above for tissue engineering as well as to a tissue engineering method that involves applying, including injecting a respective amphiphilic linear peptide and/or peptoid.

A hydrogel is typically characterized by a remarkable rigidity and are generally biocompatible and non-toxic. Depending on the selected peptide/peptoid sequence these hydrogels can show thermoresponsive or thixotropic character. Reliant on the peptide/peptoid assembling conditions the fibers differ in thickness and length. Generally rigid hydrogels are obtained that are well suited for cultivation of a variety of primary human cells, providing peptide/peptoid scaffolds that can be useful in the repair and replacement of various tissues. Disclosed is also a process of preparing these hydrogels. The exemplary usage of these hydrogels in applications such as cell culture, tissue engineering, plastic surgery, drug delivery, oral applications, cosmetics, packaging and the like is described, as well as for technical applications, as for example for use in electronic devices which might include solar or fuel cells.

As an amphiphilic linear sequence of the peptide/peptoid, a hydrogel shows high stability at physiological conditions, even at elevated temperatures. In some embodiments such a hydrogel is stable in aqueous solution at ambient temperature for a period of at least 7 days, at least 14 days, at least a month or more, such as at least 1 to about 6 months.

In some embodiments a hydrogel disclosed herein is coupled to a molecule or a particle, including a quantum dot, with characteristic spectral or fluorometric properties, such as a marker, including a fluorescent dye. A respective molecule may for instance allow monitoring the fate, position and/or the integrity of the hydrogel.

In some embodiments a hydrogel disclosed herein is coupled to a molecule with binding affinity for a selected target molecule, such as a microorganism, a virus particle, a peptide, a peptoid, a protein, a nucleic acid, a peptide, an oligosaccharide, a polysaccharide, an inorganic molecule, a synthetic polymer, a small organic molecule or a drug.

The term "nucleic acid molecule" as used herein refers to any nucleic acid in any possible configuration, such as single stranded, double stranded or a combination thereof. Nucleic acids include for instance DNA molecules (e.g., cDNA or genomic DNA), RNA molecules (e.g., mRNA), analogues of the DNA or RNA generated using nucleotide analogues or using nucleic acid chemistry, locked nucleic acid molecules (LNA), and protein nucleic acids molecules (PNA). DNA or RNA may be of genomic or synthetic origin and may be single or double stranded. In the present method of an embodiment of the invention typically, but not necessarily, an RNA or a DNA molecule will be used. Such nucleic acid can be e.g. mRNA, cRNA, synthetic RNA, genomic DNA, cDNA synthetic DNA, a copolymer of DNA and RNA, oligonucleotides, etc. A respective nucleic acid may furthermore contain non-natural nucleotide analogues and/or be linked to an affinity tag or a label. In some embodiments the nucleic acid molecule may be isolated, enriched, or purified. The nucleic acid molecule may for instance be isolated from a natural source by cDNA cloning or by subtractive hybridization. The natural source may be mammalian, such as human, blood, semen, or tissue. The nucleic acid may also be synthesized, e.g. by the triester method or by using an automated DNA synthesizer.

Many nucleotide analogues are known and can be used in nucleic acids and oligonucleotides used in the methods of exemplary embodiments of the invention. A nucleotide analogue is a nucleotide containing a modification at for instance the base, sugar, or phosphate moieties. Modifications at the base moiety include natural and synthetic modifications of A, C, G, and T/U, different purine or pyrimidine bases, such as uracil-5-yl, hypoxanthin-9-yl, and 2-aminoadenin-9-yl, as well as non-purine or non-pyrimidine nucleotide bases. Other nucleotide analogues serve as universal bases. Universal bases include 3-nitropyrrole and 5-nitroindole. Universal bases are able to form a base pair with any other base. Base modifications often can be combined with for example a sugar modification, such as for instance 2'-O-methoxyethyl, e.g. to achieve unique properties such as increased duplex stability.

A peptide may be of synthetic origin or isolated from a natural source by methods well-known in the art. The natural source may be mammalian, such as human, blood, semen, or tissue. A peptide, including a polypeptide may for instance be synthesized using an automated polypeptide synthesizer. Illustrative examples of polypeptides are an antibody, a fragment thereof and a proteinaceous binding molecule with antibody-like functions. Examples of (recombinant) antibody fragments are Fab fragments, Fv fragments, single-chain Fv fragments (scFv), diabodies, triabodies (Iliades, P., et al., FEBS Lett (1997) 409, 437-441), decabodies (Stone, B., et al., Journal of Immunological Methods (2007) 318, 88-94) and other domain antibodies (Holt, L. J., et al., Trends Biotechnol. (2003), 21, 11, 484-490). An example of a proteinaceous binding molecule with antibody-like functions is a mutein based on a polypeptide of the lipocalin family (WO 03/029462, Beste et al., Proc. Natl. Acad. Sci. U.S.A. (1999) 96, 1898-1903). Lipocalins, such as the bilin binding protein, the human neutrophil gelatinase-associated lipocalin, human Apolipoprotein D or glycodelin, posses natural ligand-binding sites that can be modified so that they bind to selected small protein regions known as haptens. Examples of other proteinaceous binding molecules are the so-called glubodies (see e.g. internation patent application WO 96/23879), proteins based on the ankyrin scaffold (Mosavi, L. K., et al., Protein Science (2004) 13, 6, 1435-1448) or crystalline scaffold (e.g. internation patent application WO 01/04144) the proteins described in Skerra, J. Mol. Recognit. (2000) 13, 167-187, AdNectins, tetranectins and avimers. Avimers contain so called A-domains that occur as strings of multiple domains in several cell surface receptors (Silverman, J., et al., Nature Biotechnology (2005) 23, 1556-1561). Adnectins, derived from a domain of human fibronectin, contain three loops that can be engineered for immunoglobulin-like binding to targets (Gill, D. S. & Damle, N. K., Current Opinion in Biotechnology (2006) 17, 653-658). Tetranectins, derived from the respective human homotrimeric protein, likewise contain loop regions in a C-type lectin domain that can be engineered for desired binding (ibid.). Where desired, a modifying agent may be used that further increases the affinity of the respective moiety for any or a certain form, class etc. of target matter.

An example of a nucleic acid molecule with antibody-like functions is an aptamer. An aptamer folds into a defined three-dimensional motif and shows high affinity for a given target structure. Using standard techniques of the art such as solid-phase synthesis an aptamer with affinity to a certain target can accordingly be formed and immobilized on a hollow particle of an embodiment of the invention.

As a further illustrative example, a linking moiety such as an affinity tag may be used to immobilise the respective molecule. Such a linking moiety may be a molecule, e.g. a hydrocarbon-based (including polymeric) molecule that includes nitrogen-, phosphorus-, sulphur-, carben-, halogen- or pseudohalogen groups, or a portion thereof. As an illustrative example, the peptide/peptoid included in the hydrogel may include functional groups, for instance on a side chain of the peptide/peptoid, that allow for the covalent attachment of a biomolecule, for example a molecule such as a protein, a nucleic acid molecule, a polysaccharide or any combination thereof. A respective functional group may be provided in shielded form, protected by a protecting group that can be released under desired conditions. Examples of a respective functional group include, but are not limited to, an amino group, an aldehyde group, a thiol group, a carboxy group, an ester, an anhydride, a sulphonate, a sulphonate ester, an imido ester, a silyl halide, an epoxide, an aziridine, a phosphoramidite and a diazoalkane.

Examples of an affinity tag include, but are not limited to, biotin, dinitrophenol or digoxigenin, oligohistidine, polyhistidine, an immunoglobulin domain, maltose-binding protein, glutathione-S-transferase (GST), calmodulin binding peptide (CBP), FLAG'-peptide, the T7 epitope (Ala-Ser-Met-Thr-Gly-Gly-Gln-Gln-Met-Gly SEQ ID NO: 52), maltose binding protein (MBP), the HSV epitope of the sequence Gln-Pro-Glu-Leu-Ala-Pro-Glu-Asp-Pro-Glu-Asp (SEQ ID NO : 53) of herpes simplex virus glycoprotein D, the hemagglutinin (HA) epitope of the sequence Tyr-Pro-Tyr-Asp-Val-Pro-Asp-Tyr-Ala (SEQ ID NO: 54), the "myc" epitope of the transcription factor c-myc of the sequence Glu-Gln-Lys-Leu-Ile-Ser-Glu-Glu-Asp-Leu (SEQ ID NO: 55) , or an oligonucleotide tag. Such an oligonucleotide tag may for instance be used to hybridise to an immobilised oligonucleotide with a complementary sequence. A further example of a linking moiety is an antibody, a fragment thereof or a proteinaceous binding molecule with antibody-like functions (see also above).

A further example of linking moiety is a cucurbituril or a moiety capable of forming a complex with a cucurbituril. A cucurbituril is a macrocyclic compound that includes glycoluril units, typically self-assembled from an acid catalyzed condensation reaction of glycoluril and formaldehyde. A cucurbit[n]uril, (CB[n]), that includes n glycoluril units, typically has two portals with polar ureido carbonyl groups. Via these ureido carbonyl groups cucurbiturils can bind ions and molecules of interest. As an illustrative example cucurbit[7]uril (CB[7]) can form a strong complex with ferrocenemethylammonium or adamantylammonium ions. Either the cucurbit[7]uril or e.g. ferrocenemethylammonium may be attached to a biomolecule, while the remaining binding partner (e.g. ferrocenemethylammonium or cucurbit[7]uril respectively) can be bound to a selected surface. Contacting the biomolecule with the surface will then lead to an immobilisation of the biomolecule. Functionalised CB[7] units bound to a gold surface via alkanethiolates have for instance been shown to cause an immobilisation of a protein carrying a ferrocenemethylammonium unit (Hwang, I., et al., J. Am. Chem. Soc. (2007) 129, 4170-4171).

Further examples of a linking moiety include, but are not limited to an oligosaccharide, an oligopeptide, biotin, dinitrophenol, digoxigenin and a metal chelator (cf. also below). As an illustrative example, a respective metal chelator, such as ethylenediamine, ethylenediamine-tetraacetic acid (EDTA), ethylene glycol tetraacetic acid (EGTA), diethylenetriaminepentaacetic acid (DTPA), N,N-bis(carboxymethyl)glycine (also called nitrilotriacetic acid, NTA), 1,2-bis (o-aminophenoxy)ethane-N,N,N',N'-tetraacetic acid (BAPTA), 2,3-dimercapto-1-propanol (dimercaprol), porphine or heme may be used in cases where the target molecule is a metal ion. As an example, EDTA forms a complex with most monovalent, divalent, trivalent and tetravalent metal ions, such as e.g. silver ($Ag^+$), calcium ($Ca^{2+}$), manganese ($Mn^{2+}$), copper ($Cu^{2+}$), iron ($Fe^{2+}$), cobalt ($Co^{3+}$) and zirconium ($Zr^{4+}$), while BAPTA is specific for $Ca^{2+}$. In some embodiments a respective metal chelator in a complex with a respective metal ion or metal ions defines the linking moiety. Such a complex is for example a receptor molecule for a peptide of a defined sequence, which may also be included in a protein. As an illustrative example, a standard method used in the art is the formation of a complex between an oligohistidine tag and copper ($Cu^{2+}$), nickel ($Ni^{2+}$), cobalt ($Co^{2+}$), or zink ($Zn^{2+}$) ions, which are presented by means of the chelator nitrilotriacetic acid (NTA).

Avidin or streptavidin may for instance be employed to immobilise a biotinylated nucleic acid, or a biotin containing monolayer of gold may be employed (Shumaker-Parry, J. S., et al., Anal. Chem. (2004) 76, 918). As yet another illustrative example, the biomolecule may be locally deposited, e.g. by scanning electrochemical microscopy, for instance via pyrrole-oligonucleotide patterns (e.g. Fortin, E., et al., Electroanalysis (2005) 17, 495). In other embodiments, in particular where the biomolecule is a nucleic acid, the biomolecule may be directly synthesised on the surface of the immobilisation unit, for example using photoactivation and deactivation. As an illustrative example, the synthesis of nucleic acids or oligonucleotides on selected surface areas (so called "solid phase" synthesis) may be carried out using electrochemical reactions using electrodes. An electrochemical deblocking step as described by Egeland & Southern (Nucleic Acids Research (2005) 33, 14, e125) may for instance be employed for this purpose. A suitable electrochemical synthesis has also been disclosed in US patent application US 2006/0275927. In some embodiments light-directed synthesis of a biomolecule, in particular of a nucleic acid molecule, including UV-linking or light dependent 5'-deprotection, may be carried out.

The molecule that has a binding affinity for a selected target molecule may be immobilised on the nanocrystals by any means. As an illustrative example, an oligo- or polypeptide, including a respective moiety, may be covalently linked to the surface of nanocrystals via a thio-ether-bond, for example by using to functionalized thiols. Any suitable molecule that is capable of linking a nanocrystal of an embodiment of the invention to a molecule having a selected binding affinity may be used to immobilise the same on a nanocrystal. For instance a (bifunctional) linking agent such as ethyl-3-dimethylaminocarbodiimide, N-(3-aminopropyl) 3-mercapto-benzamide, 3-aminopropyl-trimethoxysilane, 3-mercaptopropyl-trimethoxysilane, 3-(trimethoxysilyl) propyl-maleimide, or 3-(trimethoxysilyl) propyl-hydrazide may be used. Prior to reaction with the linking agent, the surface of the nanocrystals can be modified, for example by treatment with glacial mercaptoacetic acid, in order to generate free mercaptoacetic groups which can then employed for covalently coupling with an analyte binding partner via linking agents.

Embodiments of the present invention also include a hydrogel, which can be taken to be a water-swollen water-insoluble polymeric material. The hydrogel includes, including contains and consists of, a peptide and/or peptoid as defined above. Since a hydrogel maintains a three-dimensional structure, a hydrogel of an embodiment of the invention may be used for a variety of applications. Since the hydrogel has a high water content and includes amino acids, it is typically of excellent biocompatibility.

A hydrogel according to an embodiment of the invention is formed by self-assembly. The inventors have observed that the peptides/peptoids assemble into fibers that form mesh-like structures. Without being bound by theory hydrophobic interaction between non-polar portions of peptides/peptoids are contemplated to assist such self-assembly process.

The method of forming the hydrogel includes dissolving the peptide/peptoid in aqueous solution. Agitation, including mixing such as stirring, and/or sonication may be employed to facilitate dissolving the peptide/peptoid. In some embodiments the aqueous solution with the peptide/peptoid therein is exposed to a temperature below ambient temperature, such as a temperature selected from about 2° C. to about 15° C. In some embodiments the aqueous solution with the peptide/peptoid therein is exposed to an elevated temperature, i.e. a temperature above ambient temperature. Typically the aqueous solution is allowed to attain the temperature to which it is exposed. The aqueous solution may for example be exposed to a temperature from about 25° C. to about 85° C. or higher, such as from about 25° C. to about 75° C., from about 25° C. to about 70° C., from about 30° C. to about 70° C., from about 35° C. to about 70° C., from about 25° C. to about 60° C., from about 30° C. to about 60° C., from about 25° C. to about 50° C., from about 30° C. to about 50° C. or from about 40° C. to about 65° C., such as e.g. a temperature of about 40° C., about 45° C., about 50° C., about 55° C., about 60° C. or about 65° C. The aqueous solution with the peptide/peptoid therein may be maintained at this temperature for a period of about 5 min to about 10 hours or more, such as about 10 min to about 6 hours, about 10 min to about 4 hours, about 10 min to about 2.5 hours, about 5 min to about 2.5 hours, about 10 min to about 1.5 hours or about 10 min to about 1 hour, such as about 15 min, about 20 min, about 25 min, about 30 min, about 35 min or about 40 min.

In some embodiments a hydrogel disclosed herein is a biocompatible, including a pharmaceutically acceptable hydrogel. The term "biocompatible" (which also can be referred to as "tissue compatible"), as used herein, is a hydrogel that produces little if any adverse biological response when used in vivo. The term thus generally refers to the inability of a hydrogel to promote a measurably adverse biological response in a cell, including in the body of an animal, including a human. A biocompatible hydrogel can have one or more of the following properties: non-toxic, non-mutagenic, non-allergenic, non-carcinogenic, and/or non-irritating. A biocompatible hydrogel, in the least, can be innocuous and tolerated by the respective cell and/or body. A biocompatible hydrogel, by itself, may also improve one or more functions in the body.

Depending on the amino acids that are included in the peptide/peptoid that is included in a hydrogel, a respective hydrogel may be biodegradable. A biodegradable hydrogel gradually disintegrates or is absorbed in vivo over a period of time, e.g., within months or years. Disintegration may for instance occur via hydrolysis, may be catalysed by an enzyme and may be assisted by conditions to which the hydrogel is exposed in a human or animal body, including a tissue, a blood vessel or a cell thereof. Where a peptide is made up entirely of natural amino acids, a respective peptide can usually be degraded by enzymes of the human/animal body.

A hydrogel according to an embodiment of the invention may also serve as a depot for a pharmaceutically active compound such as a drug. A hydrogel according to an embodiment of the invention may be designed to mimic the natural extracellular matrix of an organism such as the human or animal body. A fiber formed from the peptide/peptoid of an embodiment of the invention, including a respective hydrogel, may serve as a biological scaffold. A hydrogel of an embodiment of the invention may be included in an implant, in a contact lens or may be used in tissue engineering. In one embodiment, the peptides consist typically of 3-7 amino acids and are able to self-assemble into complex fibrous scaffolds which are seen as hydrogels, when dissolved in water or aqueous solution. These hydrogels can retain water up to 99.9% and possess sufficiently high mechanical strength. Thus, these hydrogels can act as artificial substitutes for a variety of natural tissues without the risk of immunogenicity. The hydrogels in accordance with the present invention may be used for cultivating suitable primary cells and thus establish an injectable cell-matrix compound in order to implant or reimplant the newly formed cell-matrix in vivo. Therefore, the hydrogels in accordance with the present invention are particularly useful for tissue regeneration or tissue engineering applications. As used herein, a reference to an "implant" or "implantation" refers to uses and applications of/for surgical or arthroscopic implantation of a hydrogel containing device into a human or animal, e.g. mammalian, body or limb. Arthroscopic techniques are taken herein as a subset of surgical techniques, and any reference to surgery, surgical, etc., includes arthroscopic techniques, methods and devices. A surgical implant that includes a hydrogel according to an embodiment of the invention may include a peptide and/or peptoid scaffold. This the peptide and/or peptoid scaffold may be defined by the respective hydrogel. A hydrogel of an embodiment of the invention may also be included in a wound cover such as gauze or a sheet, serving in maintaining the wound in a moist state to promote healing.

Depending on the amino acid sequence used in the peptide/peptoid the hydrogel may be temperature-sensitive. It may for instance have a lower critical solution temperature or a temperature range corresponding to such lower critical solution temperature, beyond which the gel collapses as hydrogen bonds by water molecules are released as water molecules are released from the gel.

The disclosed subject matter also provides improved chiral amphiphilic natural-based peptides and/or peptoids that assemble to peptide/peptoid hydrogels with very favorable material properties. The advantage of these peptide/peptoid hydrogels is that they are accepted by a variety of different primary human cells, thus providing peptide scaffolds that can be useful in the repair and replacement of various tissues. Depending on the chirality of the peptide monomer the character of the hydrogels can be designed to be more stable and less prone to degradation though still biocompatible.

A hydrogel and/or a peptide/peptoid described herein can be administered to an organism, including a human patient per se, or in pharmaceutical compositions where it may include or be mixed with pharmaceutically active ingredients or suitable carriers or excipient(s). Techniques for formulation and administration of respective hydrogels or peptides/peptoids resemble or are identical to those of low molecular weight compounds well established in the art. Exemplary routes include, but are not limited to, oral, transdermal, and parenteral delivery. A hydrogel or a peptide/peptoid may be used to fill a capsule or tube, or may be provided in compressed form as a pellet. The peptide/peptoid or the hydrogel may also be used in injectable or sprayable form, for instance as a suspension of a respective peptide/peptoid.

A hydrogel of an embodiment of the invention may for instance be applied onto the skin or onto a wound. Further suitable routes of administration may, for example, include depot, oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections. It is noted in this regard that for administering microparticles a surgical procedure is not required. Where the microparticles include a biodegradable polymer there is no need for device removal after release of the anti-cancer agent. Nevertheless the microparticles may be included in or on a scaffold, a coating, a patch, composite material, a gel or a plaster.

In some embodiments one may administer a hydrogel and/or a peptide/peptoid in a local rather than systemic manner, for example, via injection.

Pharmaceutical compositions that include a hydrogel and/or a peptide/peptoid of an embodiment of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with an embodiment of the present invention thus may be formulated in conventional manner using one or more physiologically acceptable carriers including excipients and auxiliaries that facilitate processing of the hydrogel and/or peptide/peptoid into preparations that can be used pharmaceutically. Proper formulation is dependent upon the route of administration chosen.

For injection, the peptide/peptoid of an embodiment of the invention may be formulated in aqueous solutions, for instance in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the hydrogel and/or peptide/peptoid can be formulated readily by combining them with pharmaceutically acceptable carriers well known in the art. Such carriers enable the hydrogel and/or peptide/peptoid, as well as a pharmaceutically active compound, to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatine, as well as soft, sealed capsules made of gelatine and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the peptides/peptoids may be suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

The hydrogel and/or peptide/peptoid may be formulated for parenteral administration by injection, e.g., by intramuscular injections or bolus injection or continuous infusion. Formulations for injection may be presented in unit dosage form, e. g., in ampules or in multi-dose containers, with an added preservative. The respective compositions may take such forms as suspensions, solutions or emulsions in oily or aqueous vehicles, and may contain formulatory agents such as suspending, stabilizing and/or dispersing agents.

The hydrogel and/or peptide/peptoid may be formulated for other drug delivery systems like implants, or tranbdermal patches or stents.

In a first aspect, the present invention provides the use hydrogel-forming peptides/peptoids/peptidomimetics in biofabrication.

Peptide self-assembly is an elegant and expedient "bottom-up" approach towards designing ordered, three-dimensional nanobiomaterials. Reproducible macromolecular nanostructures can be obtained due to the highly specific interactions that govern self-assembly. The amino acid sequence determines peptide secondary structure and interactions with other molecules, which in turn dictates the higher order macromolecular architecture.

Self-assembled nanofibrillar peptide scaffolds are of great interest for applications in regenerative medicine. As their nanofibrous topography resembles the extracellular matrix, they have been extensively applied as biomimetic scaffolds, providing spatial and temporal cues to regulate cell growth and behavior. Spatially defined, large-scale three-dimensional scaffolds, incorporating cells and other biochemical cues, can be obtained by 3D microdroplet bio-printing and moulding techniques. Self-assembling peptides, peptidomimetics and peptidic conjugates can serve as building blocks for printing or moulding of biocompatible macromolecular scaffolds that support the growth of encapsulated cells.

Figure 1:
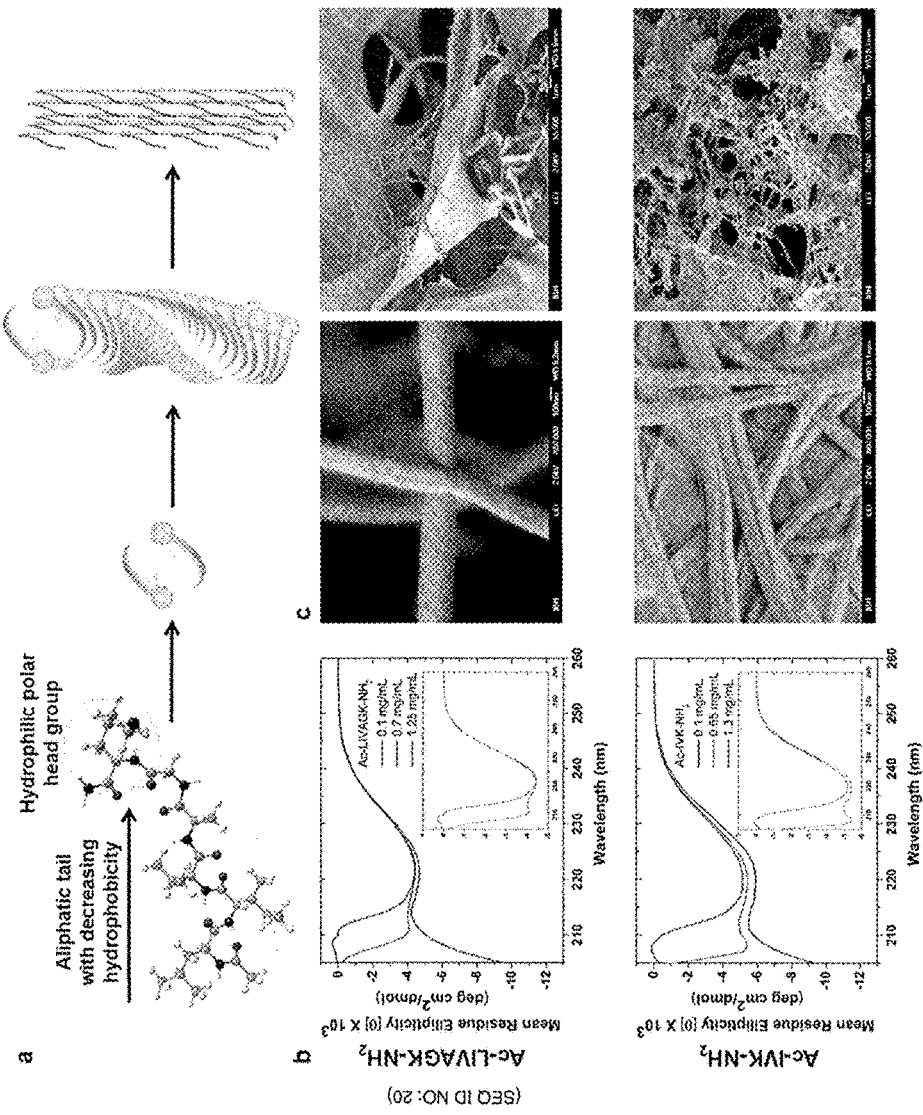
FIG. 1. Self-assembly of ultrashort peptides/peptidomimetics into macromolecular nanofibrous hydrogels.

This disclosure describes a novel class of ultrashort peptides/peptidomimetics/conjugates, with a characteristic motif that facilitates self-assembly in aqueous conditions, forming porous, nanofibrous scaffolds that are biocompatible (FIG. 1). Several subclasses demonstrate stimuli-responsive gelation (FIG. 2) and can be used to for bio-printing of mini-hydrogel arrays and 3D organotypic biological constructs. The stimuli-responsive nature can also be exploited to produce hydrogel fibers or "noodles" through extrusion into salt solution baths. The resulting fibers can potentially be collected and used to create woven and aligned fibrous scaffolds.

The characteristic motif that drives self-assembly consists of a N-terminus "trail" of 2 to 7 natural aliphatic amino acids, arranged in decreasing hydrophobicity towards the C-terminus (FIG. 1). At the C-terminus, a polar "head" group, which can be
- a polar amino acid (in particular in case of the hydrophobic peptides which do not contain an amphiphilic sequence),
- a functional group (e.g. carboxylic acid, amine, ester, alcohol, aldehyde, ketone, maleimide), small molecules (e.g. sugars, alcohols, vitamins, hydroxyl-acids, amino acids)

and/or short polar linkers.

Self-assembly in aqueous conditions occurs when the amino acids pair and subsequently stack into α-helical fibrils (FIG. 1). Hydrogels are obtained when further aggregation of the fibrils into 3D networks of nanofibers entrap water (FIG. 3A).

The presence of functional groups enables to perform chemical modifications pre- and post-assembly. For instance, bioactive moieties such as growth factors, lipids, cell-receptor ligands, hormones and drugs can be conjugated to the scaffold post-assembly, giving rise to functionalized hydrogels.

Several subclasses of these peptides/peptidomimetics/conjugates demonstrate stimuli-responsive gelation (FIG. 2). In particular, a subclass of peptides with lysine or lysine-mimetic molecules as the polar head group exhibit enhanced gelation and rigidity in the presence of salts and elevated pH (FIGS. 3A, B and C). The gelation duration can be tuned by titrating the peptide and salt concentration. This opens avenues for the development of bio-printing, wherein gelation can be controlled and limited to desired areas through the co-injection of salt solutions.

Furthermore, the gelation process is slightly endodermic, which adds an element of temperature-sensitivity and eliminates the possibility of thermal damage to encapsulated cells. During the process of gelation, the ability to modulate gelation duration enables to sculpt the hydrogel construct into the desired shape for applications in regenerative medicine. The mechanical properties of this subclass of peptide hydrogels are enhanced by increasing salt concentration and pH. The stiffness and tunable mechanical properties render this subclass of amidated peptides hydrogels as ideal candidates for developing biological constructs that fulfill mechanically supportive roles. Through the judicious addition of ionic buffers and bases, less peptide can be used to attain equivalent mechanical stiffness while maintaining the porosity for supporting cell migration. The ability to modulate the mechanical properties and porosity is integral to creating organotypic constructs with mechanical properties comparable to that of the native tissue. In comparison, other peptide hydrogels, based on self-assembling α-helices, β-hairpins (G'≤2 kPa) and β-sheets (G'≤2 kPa), cannot attain such high rigidity (References: α-helices:

Banwell, E. F. et al. Rational design and application of responsive alpha-helical peptide hydrogels. Nat Mater 8, 596-600 (2009).

Yan, C. & Pochan, D. J. Rheological properties of peptide-based hydrogels for biomedical and other applications. Chem Soc Rev 39, 3528-3540 (2010). β-hairpins:

Yan, C. et al. Injectable solid hydrogel: mechanism of shear-thinning and immediate recovery of injectable β-hairpin peptide hydrogels. Soft Matter 6, 5143 (2010).

Schneider, J. P. et al. Responsive hydrogels from the intramolecular folding and self-assembly of a designed peptide. J Am Chem Soc 124, 15030-15037 (2002).

References: β-sheets:

Zhang, S., Holmes, T., Lockshin, C. & Rich, A. Spontaneous assembly of a self-complementary oligopeptide to form a stable macroscopic membrane. Proc. Natl. Acad. Sci. USA 90, 3334-3338 (1993).

Liu, J., Zhang, L., Yang, Z. & Zhao, X. Controlled release of paclitaxel from a self-assembling peptide hydrogel formed in situ and antitumor study in vitro. Int J Nanomedicine 6, 2143-2153 (2011).

Aggeli, A. et al. Responsive gels formed by the spontaneous self-assembly of peptides into polymeric beta-sheet tapes. Nature 386, 259-262 (1997).)

As a proof-of-concept, this subclass of peptides was used to demonstrate the feasibility of bio-printing to develop mini-hydrogel arrays and 3D organoid structures for screening and regenerative medicine. This subclass of peptides demonstrates good solubility in water, forming solutions with low viscosity. This facilitates the printing and prevents the clogging of the needle/printer. Upon interacting with a physiological salt solution (such as phosphate buffered saline, PBS), the peptide solution gels instantaneously. As shown in FIG. 3D, arrays of microdroplets will form mini-hydrogels that adhere to a glass or polystyrene surface upon washing with PBS.

The peptides/peptidomimetics are biocompatible. Stem cells (mesenchymal, progenitor, embryonic and induced pluripotent stem cells) and primary cells isolated from patient samples (fibroblasts, nucleus pulposus) can be mixed with the peptide during the dispensing process (FIG. 4). Following gelation, the cells are immobilized to the drop. Nanoparticles, small molecule drugs, oligonucleotides, and proteins can be similarly co-encapsulated (FIGS. 4 and 5).

Coupled with the advent of high-throughput histological screening using slide scanners, this technology can be used to evaluate different test compounds using minimal cell numbers on a single microscope slide (FIG. 6).

By incorporating cross-linkers, we can improve the mechanical stability of these mini-hydrogels. Bioactive functionalities can be also incorporated through mixing or cross-linking with polymers (FIG. 7).

We can mix different peptides/peptidomimetics/conjugates without compromising their propensity for self-assembly. This allows us to combine different compounds to access different functional groups for conjugation and vary the bulk properties.

Extending the technology towards 3D microdroplet printing and moulding, biological, organotypic constructs with distinct, multi-functional micro-niches can be obtained (FIG. 8). Multi-cellular constructs can also be obtained as the hydrogel can spatially confine different cell types during the printing process. The peptide/peptidomimetic/conjugate scaffold will provide the co-encapsulated cells with mechanical stability. Genes, small molecules and growth factors can be co-delivered to enhance cell survival, promote stem cell differentiation and modulate the host immune response. The resulting 3D biological constructs can be used as organoid models for screening drugs, studying cell behavior and disease progression, as well as tissue-engineered implants for regenerative medicine.

In addition to microdroplets, also obtain fibres ("noodles") can be obtained by extruding the peptidic solution into a high concentration salt solution (FIG. 3E). Co-encapsulation of cells and bioactive moieties can be performed. The fibrous microenvironment can give rise to new applications such as woven scaffolds, aligned scaffolds and 3D patterned co-culture scaffolds.

Cells, such as human embryonic stem cells, encapsulated in hydrogels of the invention proliferate and maintain their pluripotency, demonstrating that culturing in 3D preserves the native phenotype of primary cells (see FIG. 11). Cells can also be printed onto the surface of bioprinted hydrogels of the invention. Culturing in 3D better preserves the native phenotype of primary cells and will enable cells to be cultured in higher density (see FIG. 12).

The nanofibrous hydrogel is biocompatible, supporting the proliferation of primary (rabbit epithelial fibroblasts, human dermal fibroblasts, and kidney tubular cells) and stems cells (mesenchymal, embryonic and induced pluripotent stem cells). The cells can be cultured on hydrogel coatings or encapsulated within the hydrogel (FIG. 4). In the latter, the cells adopt a 3D morphology that is more similar to their native state. The nanofibrous scaffold provides mechanical and topographical cues that facilitate cell attachment and survival.

The need for tissue cultures which resemble native tissue limits the study of pathogen infectivity and transmission in several ways. Firstly, it restricts the amount of pathogen stock available for test—the pathogen has to be amplified in vivo, which is particularly challenging when the pathogen only infects human hosts. This is the case for diseases such as malaria, dengue and norovirus. Secondly, it is challenging to pinpoint mechanisms of viral infectivity (entry into the target cells and replication), as donor tissue would have to be obtained for confirmation. Culturing in 3D better preserves the native phenotype of primary cells and will also enable cells to be cultured at a higher density. For instance Caco2 cells cultured on the peptide receptor FUT2A, compared to constructs cultured on glass cover slips (FIG. 12). In view that FUT2A is implicated for Norovirus infectivity, monolayer cultures on tissue culture polystyrene and glass cover slips do not support studies of viral infectivity nor permit pathogen expansion. Attempts to use Cytodex microcarriers in a rotating bioreactor to culture Caco2 cells and subsequently infect them to amplify the virus demonstrate limited success. These dextran microcarriers are opaque and are incompatible with absorbance and fluorescent-based diagnostic assays. Thus, developing cell models to study viral entry into enterocytes and mechanisms of replication facilitates the development of testing protocols, effective sanitization methods and rapid diagnostic tests.

Key Features:
- A novel class of peptides/peptidomimetics/conjugates which only consists of 2 to 7 amino acids which can self-assemble into nanofibrous scaffolds, in particular 3D nanofibrous scaffolds. The significantly shorter sequence implies a lower cost and ease of synthesis and purification compared to other self-assembling peptide/conjugate technologies.
- An interesting mechanism of self-assembly into (biomimetic) nanofibrous scaffolds in aqueous conditions and polar solvents. Such scaffolds can provide mechanical and topographical cues for cellular and tissue regeneration and/or that influence cell proliferation, migration and behavior.
- A versatile material which can be formulated in different ways. Some subclasses are stimuli-responsive, which facilitates the development of bio-printing technologies. Several subclasses demonstrate stimuli-responsive behavior which can be exploited for various applications.
- A subclass of peptides demonstrates salt and pH-responsive gelation. In particular, instantaneous gelation can be obtained upon exposure to a physiologically compatible salt solution.
- When dissolved in water, the peptidic solution has low viscosity and can be easily dispensed through needles and print-heads. This minimizes the possibility of clogging.
- The stimuli-responsiveness can also be exploited to generate hydrogel fibers/'noodles'. These fibers can subsequently be aligned or woven to create innovative scaffolds for tissue engineering and disease models.
- On a macroscale, we can also use moulds (such as those made of silicone) to pattern the hydrogels in a 3D fashion.
- The hydrogels are biocompatible and can be used to encapsulate cells. Upon gelation, the resulting hydrogel is stable and not easily dissociated. Therefore, encapsulated cells cannot escape. Cells can be cultured in and/or on the hydrogels.
- Cells can be printed/deposited onto printed/fabricated scaffold. Cells can also be encapsulated during the printing process and additional cells deposited on the surface subsequently. This is advantageous for subsequent applications to develop realistic cell culture models such as gut and skin epithelia.
- A unique method for three-dimensional encapsulation of primary cells to maximize initial cell survival and promote subsequent cell proliferation and development of tissue cultures resembling native tissue. The mechanical properties of the hydrogel can also be tuned to match that of native tissue to enhance maintenance of native phenotype.
- An enabling technology which allows for the development of cell models which resemble native tissue and are susceptible towards pathogen infection and replication. This can facilitate on pathogen entry and reproduction, thereby enabling the development of testing protocols, effective sanitization methods and rapid diagnostic tests. This is integral for diseases such as malaria, dengue and norovirus which affects human hosts and demonstrate poor replication in existing cell culture and animal models.
- The cell culture models can conceivably be applied towards drug screening and in vitro technology.
- The peptide hydrogels are optically transparent, thus enabling the use of standard techniques for absorbence measurements, fluorescence and bright field imaging. Cell-based studies using high-throughput microscopy and biochemical assays to elucidate the biology of complex collections of cells and quantify their response to various stimuli in a temporal fashion are also feasible.
- The constructs are stable for long periods of culture as they do not associate without mechanical and enzymatic intervention, thereby enabling long-term studies.
- Bioactive moieties, such as oligonucleotides, proteins (growth factors, antibodies and cytokines) and small molecule drugs, as well as nano- and microparticles, can be co-encapsulated to influence cell behavior. The release of encapsulated biomolecules can also be modulated by porosity and various molecular interactions.
- Post-assembly modifications are feasible due to the presence of functional groups. Bioactive moieties such as growth factors can also be conjugated to the peptidic backbone or functional groups on the conjugate to modulate biological behavior.
- Due to stimuli-responsive nature of the peptide, the scaffold and stem cells can be bio-printed or moulded into specific shapes for developing platform technologies for large scale 3D cell culture, cell-based high-throughput screening and regenerative medicine applications.

In a second aspect, the present invention provides a novel class of hydrogel-forming hydrophobic peptides/peptidomimetics.

The inventors have found advantages and properties that the absence of a polar head group, such as hydrophilic amino acid(s), is giving to small peptides consisting solely of hydrophobic amino acids.

The absence of a polar group at the C-terminus gives rise to a new class of self-assembling peptides with different properties to the so far disclosed class of ultrashort peptides. It is not evident for a person aware of the state-of-the-art that a solely hydrophobic sequence of amino acids will be able to self-assemble to fibrous scaffolds, ending up in hydrogels. The so far explored assembly process of the currently explored type of ultrashort peptides was thought to be solely depending on amphiphilic sequences. The absence of a polar head group would have been more likely predicted to generate micelle-like structures, but not soft solid material. In addition, the absence of a polar head group leads to new material properties and gives so far unexplored possibilities to create novel smart biomaterial.

New advantages in material properties can be designed by the functionalization via the conjugation of non-amino acids such as small molecules, functional groups and short linkers. These small molecule/functional group/short linkers bestow new material properties such as bio-adhesiveness and receptor-targeting. The new peptide sequence characteristics enables the development of new (and different to the one developed so far) applications. It also simplifies the purification of the desired compound. Compared to the peptide itself, the presence of the functional group/short linker at the C-terminus enhances ease of functionalization and the ability to chemically conjugate multiple bioactive molecules (such as cytokines, prodrugs etc) to a single peptidomimetic/peptidic conjugate. We can also eliminate undesired side reactions and non-specific interactions between the peptidomimetic/peptidic conjugate and bioactive molecules of interest.

EXAMPLES

Experiments have been performed to illustrate the technical aspects of exemplary embodiments of the present invention. The following examples are described in the Experimental Methods and Results. The skilled artisan will readily recognize that the examples are intended to be illustrative and are not intended to limit the scope of the present invention.

Experimental Methods and Results

Peptides

The peptide sequences were designed to represent an amphiphilic peptide structure containing a hydrophilic head group and a hydrophobic tail. The rationale for the peptides design was to create a peptide monomer of decreasing size resembling a cone shaped structure. The hydrophobic tail differs by using different aliphatic amino acids. It is consisting of the following aliphatic amino acids such as glycine, alanine, valine, leucine and isoleucine and the hydrophilic head group is consisting of one or two polar or charged amino acids. The sequence order of the hydrophobic tail differed by using different aliphatic amino acids. The peptides were commercially synthesized from GL Biochem, Shanghai, China. In order to verify the reproducibility of the peptide hydrogel-forming behavior peptides were also synthesized from other companies (Biomatik Corp., Anaspec. Inc, USA). The peptides have a purity of equal or higher than 95% verified by High-performance liquid chromatography (HPLC) and mass spectrometry. The peptide stock solutions were dissolved in water at 5 to 10 mg/ml. Most of the peptides are acetylated at the N-terminus.

Peptide-based Hydrogel Preparation.

All peptides (GL Biochem, Shanghai, China, ≥98% purity) were freshly prepared in order to avoid premature peptide aggregation. The peptides were dissolved in water and left at room temperature to form hydrogels. Depending on the peptide concentration, the self-assembly process occurred immediately, within hours or even within days (experimental time frame for gelation). For higher peptide concentrations peptides were dissolved in milliQ water by vortexing. If a forced and accelerated hydrogel preparation was needed, the peptide solution was subjected to sonication in a water bath (Barnstead Labline 9319 UltrasonicLC60H). No significant structural differences were observed between hydrogels produced via self-assembly and those whose assembly was facilitated by sonication. Few peptides formed hydrogels more easily at elevated temperatures, i.e. at 50° C.

To study the effect of concentration variation, both $AcLD_6$ (L) and AcID3 (L) hydrogels were prepared with varying concentration as specified above. To study the effect of monovalent and divalent cations, $AcLD_6$ (L) hydrogels were prepared by dissolving peptide in 10, 50, 100 and 150 mM NaCl and $CaCl_2$ solutions. FESEM and rheology studies were further performed to characterize the morphology and strength of these hydrogels.

Preparation of gelatin and collagen gels: Gelatin (Type A, G1890; Sigma Aldrich) hydrogels was prepared by first dissolving gelatin in milli Q water by heating followed by cooling till the gelation was observed. Collagen (Type I from bovine, Advanced Biomatrix, USA) was diluted with PBS buffer to a concentration of 1.5 mg/ml and titrated to pH 7.4 using 0.1M NaOH. Gelation was achieved by incubating the solution at 37° C. for 1 hour.

Circular Dichroism (CD) Spectroscopy

Secondary peptide structures were analyzed by measuring ellipticity spectra using the Aviv Circular Dichroism Spectrometer, model 410. CD samples were prepared by diluting stock peptides solutions (5-10 mg/ml) in water. The diluted peptide solutions were filled in to a cuvette with 1 mm path length and spectra were acquired. As a blank reference water was used and the reference was subtracted from the raw data before molar ellipticity was calculated. The calculation was based on the formula: $[\theta]_\lambda = \theta_{obs} \times 1/(10 \text{ Len})$, where $[\theta]_\lambda$ is the molar ellipticity at λ in deg $cm^2$ d/mol, is the observed ellipticity at □λ in mdeg, L is the path length in cm, c is the concentration of the peptide in M, and n is the number of amino acids in the peptide. Secondary structure analysis was done using CDNN software.

Environmental Scanning Electron Microscopy (ESEM)

Samples were placed onto a sample holder of FEI Quanta 200 Environmental Scanning Electron Microscopy. The surface of interest was then examined using accelerating voltage of 10 kV at a temperature of 4° C.

Field Emission Scanning Electron Microscopy (FESEM)

Samples were frozen at −20° C. and subsequently to −80° C. Frozen samples were further freeze dried. Freeze dried samples were fixed onto a sample holder using conductive tape and sputtered with platinum from both the top and the sides in a JEOL JFC-1600 High Resolution Sputter Coater. The coating current used was 30 mA and the process lasted for 60 sec. The surface of interest was then examined with a JEOL JSM-7400F Field Emission Scanning Electron Microscopy system using an accelerating voltage of 5-10 kV.

Rheological Measurements

To determine the viscoelastic properties of the peptide-based hydrogels, hydrogels were subjected to dynamic time, strain and frequency sweep experiments using the ARES-G2 rheometer (TA Instruments, Piscataway, N.J.) with the 25.0 mm diameter titanium parallel plate geometry and a 0.8 mm gap distance. Oscillatory frequency study was performed to compare the strength of peptide based hydrogel with varying concentration of peptides, or for peptide in presence of monovalent or divalent ions. Oscillatory frequency sweep studies were performed at 0.1-100 rad/s frequency and 0.1% strain at 25° C. and 50° C.

Ac-LD$_6$[L]:
Peptide sequence: Ac-LIVAGD-COOH (SEQ ID NO: 17)
Molecular weight: 629.56
(1) Temperature Sweep Study for Ac-LD$_6$ (L) (SEQ ID NO: 17):
  (a) The peptide mixture was then placed on rheometer lower plate. Following parameters were optimized:
   Gap between two plates: 1 mm
   Strain: 10%
   Frequency: 6.28 rad/sec
   Temperature scan: 4° C. to 60° C.
   Sample volume: 500 µl
(2) Frequency Sweep Study for Ac-LD$_6$ (L)(SEQ ID NO: 17):
  Optimized parameter required to perform frequency sweep study
   Gap between two plates: 0.8 mm
   Strain: 0.1%
   Temperature: 25 and 50° C.
   Sample volume: 1 ml
   Frequency scan: 0.1 rad/sec to 100 rad/sec
   Concentration of Ac-LD-6 (L) in hydrogel: 10 mg/ml
(3) Effect of Concentration Variation of Ac-LD$_6$ (L)(SEQ ID NO: 17) on Gel Strength:
  Optimized parameters that are required to perform frequency sweep studies for measuring gel strength are as follows:
   Gap between two plates: 0.8 mm
   Strain: 0.1%
   Temperature: 25 and 50° C.
   Sample volume: 1 ml
   Frequency scan: 0.1 rad/sec to 100 rad/sec
   Concentrations of Ac-LD$_6$ (L) in hydrogels: 5 mg/ml, 10 mg/ml, 15 mg/ml and, 20 mg/ml and 30 mg/ml in water.
(4) Effect of Sodium Chloride (NaCl) on the Gel Strength of Ac-LD$_6$ (L) (SEQ ID NO: 17):
  Effect of sodium chloride on Ac-LD$_6$ (L) (SEQ ID NO: 17) based hydrogels, were studied by performing a frequency sweep study on hydrogels prepared by dispersing 10 mg of Ac-LD-6 (L) ( SEQ ID NO: 17) in varying concentration of NaCl solution for example 10 mM, 50 mM, 100 mM and 150 mM of NaCl solution using optimized procedure to form hydrogels. Optimized parameter required to perform frequency sweep study to measure gel strength in presence of NaCl are as follows:
   Gap between two plates: 0.5 mm and 0.8 mm
   Strain: 10% and 0.1% respectively
   Temperature: 25° C. and 50° C.
   Sample volume: 1 ml
   Frequency scan: 0.1 rad/sec to 100 rad/see
   Concentrations of NaCl solutions used to prepare 10 mg/ml of Ac-LD-6 (L)
   Hydrogels: 10 mM, 50 mM, 100 mM, 150 mM NaCl solution.

Ac-LIVAGK-NH, [L] (SEQ ID NO: 20) and Ac-ILVAGK-NH$_2$[L] (SEQ ID NO: 21): Preparation of hydrogels. To prepare this subclass of peptide hydrogels, the lyophilized peptide powders were first dissolved in cold milliQ water and mixed by vortexing for 30 seconds to obtain a homogenous solution. 10% volume of 9% sodium chloride or 10-times phosphate-buffered saline was subsequently added and the resultant solution vortexed for another 30 seconds to evaluate gelation. The gelation occurred between minutes to overnight, depending on the peptide concentration and buffer used. Gelation can be facilitated by sonication or heating.

Hydrogel samples were prepared in polydimethysiloxane moulds to obtain approximately 1 mm thick, 8 mm diameter discs. Dynamic strain and oscillatory frequency sweep experiments were carried out using the ARES-G2 Rheometer (TA Instruments, Piscataway, N.J.) with 8 mm titanium parallel plate geometry. The effects of varying several parameters on viscoelastic properties were studied as follows:
  (1) Effect of varying concentration
  (2) Effect of varying ionic strength of the solution (water vs saline vs PBS)
  (3) Effect of varying pH Extrusion from 27 Gauge Needle
  5 mg/mL of Ac-ILVAGK-NH$_2$ (SEQ ID NO: 21) solution at 4° C. was extruded from a 1 mL syringe with a 27 gauge needle into 10×PBS solution at room temperature.

Preparation of Hydrogel Droplets
  We obtained hydrogel arrays by simply dispensing small volume droplets (0.5, 1, 2, 5, 10 and 20 µL) of peptide solution and subsequently mixing or washing with PBS. The viscosity and rigidity increases significantly upon gelation, conferring high shape fidelity, which enables us to localize the hydrogel droplets to the site of deposition, control the internal composition and suspend encapsulated cells or bioactive moieties, two important criteria for bioinks. To date, we have generated hydrogel droplet arrays of various volumes, encapsulating small molecules, DNA, mRNA, nanoparticles, proteins and cells.

Encapsulation of Human Mesenchymal Stein Cells
  Human mesenchymal stem cells were obtained from Lonza (Basel, Switzerland) and cultured in α-MEM medium with 20% fetal bovine serum, 2% L-glutamine and 1% penicillin-streptomycin. Upon trypsinization, the cells were suspended in PBS and subsequently added into or onto peptide solutions (in PBS). The constructs were then allowed to gel at 37° C. for 15 minutes before media was added.

Hydrophobic Peptides which Self-assemble into Nanofibrous Hydrogels
  Materials. All peptides used in this study were manually synthesized by American Peptide Company (Sunnyvale, Calif.) using solid phase peptide synthesis and purified to >95% via HPLC. Amino acid and peptide content analysis were performed.

Preparation of hydrogels. To prepare the peptide hydrogels, the lyophilized peptide powders were first dissolved in milliQ water and mixed by vortexing for 30 seconds to obtain a homogenous solution. The gelation occurred between minutes to overnight, depending on the peptide concentration. Gelation can be facilitated by sonication or heating.

Functionalization of C-terminus. To functionalize the C-terminus, biotin and L-DOPA was incorporated during solid phase peptide synthesis by first reacting the Fmoc protected precursor to the Wang or Rink-amide resin. The final product was purified using HPLC/MS, lyophilized and evaluated for gelation.

Field emission scanning electron microscopy. Hydrogel samples were flash frozen in liquid nitrogen and subsequently freeze-dried. Lyophilized samples were sputtered with platinum in a JEOL JFC-1600 High Resolution Sputter Coater. Three rounds of coating were performed at different angles to ensure complete coating. The coated sample was then examined with a JEOL JSM-7400F FESEM system using an accelerating voltage of 2-5 kV.

Example 2

2.1 Methods

Materials. All peptides used in this study were manually synthesized by American Peptide Company (Sunnyvale, Calif.) using solid phase peptide synthesis and purified to >95% via HPLC. Amino acid and peptide content analysis were performed. All cell culture reagents were purchased from Invitrogen (Carlsbad, Calif.).

Preparation of hydrogels. To prepare the peptide hydrogels, the lyophilized peptide powders were first dissolved in cold milliQ water and mixed by vortexing for 30 seconds to obtain a homogenous solution. 10% volume of 9% sodium chloride or 10-times phosphate-buffered saline was subsequently added and the resultant solution vortexed for another 30 seconds to evaluate gelation. The gelation occurred between minutes to overnight, depending on the peptide concentration and buffer used. Gelation can be facilitated by sonication or heating.

Circular dichroism spectroscopy. CD spectra were collected with an Aviv 410 CD spectrophotometer fitted with a Peltier temperature controller, using rectangular quartz suprasil cuvettes with an optical path length of 5 mm. Data acquisition was performed in steps of 1.0 nm at a wavelength range from 190-260 nm with a spectral bandwidth of 1.0 nm. Samples were freshly prepared for each measurement and the sample volume in the cuvette was kept constant at 1.6 mL. All spectra were baseline-corrected using milliQ water as the baseline.

Field emission scanning electron microscopy. Hydrogel samples were flash frozen in liquid nitrogen and subsequently freeze-dried. Lyophilized samples were sputtered with platinum in a JEOL JFC-1600 High Resolution Sputter Coater. Three rounds of coating were performed at different angles to ensure complete coating. The coated sample was then examined with a JEOL JSM-7400F FESEM system using an accelerating voltage of 2-5 kV.

Rheology. Hydrogel samples were prepared in polydimethysiloxane moulds to obtain approximately 1 mm thick, 8 mm diameter discs. Dynamic strain and oscillatory frequency sweep experiments were carried out using the ARES-G2 Rheometer (TA Instruments, Piscataway, N.J.) with 8 mm titanium parallel plate geometry.

Cell culture. Human mesenchymal stem cells were obtained from Lanza (Basel, Switzerland) and cultured in α-MEM medium with 20% fetal bovine serum, 2% L-glutamine and 1% penicillin-streptomycin. The cells used in the experiments were between passage 2 and 6. Rabbit nucleus pulposus cells were obtained from the National University Hospital of Singapore under approved animal protocols. Confocal microscopy was performed using a Zeiss LSM 510 microscope at the Advanced Microscopy Laboratory in the Biopolis Shared Facilities (A*STAR, Singapore).

In vivo biocompatibility. The biocompatibility was evaluated by subcutaneously implanting 30 μL hydrogel samples in male C57BL6 mice for up to two months. Post-euthanasia, the implant site was excised for histological analysis. The experiment was carried out under IACUC protocols approved by A*STAR's Biological Resource Facility. The guinea pig maximization study was conducted by a contract research organization, Toxikon, under GLP conditions outlined in ISO standard 10993-10.

Induced disc degeneration rabbit model. In order to simulate degenerative disc disease in three lumbar discs per animal (L3/L4, L4/L5 and L5/L6), the annulus fibrosus of New Zealand White rabbits were punctured and the nucleus pulposus harvested by aspiration[27]. The experiment was carried out under IACUC protocols approved by National University of Singapore. One month post-injury, the hydrogel and cell therapy treatments were injected into two of the damaged discs, with one remaining as an untreated control. Two months post-injury, the animals were euthanized and tissue samples collected for ex vivo MRI experiments and histology. The MRI experiments were performed in the 7T Bruker Clinscan MRI system, and the images were acquired using a Transmit/Receive 72 mm volume coil. T1 and T2 weighted images were acquired with the following acquisition parameters: TR/TE=400/12 ms and TR/TE=1500/67 ms, respectively. Other relevant experimental parameters include: 70 mm FOV, 1 mm slice thickness and the final image was an average of 4.

2.2 Biocompatibility in vitro and in vivo

The peptide hydrogels demonstrated good in vivo stability, an important consideration for implants. Ideally, the hydrogels should remain stable under physiological conditions for at least 6 to 12 months, eliminating the need for repeated treatments within a short time frame. Subcutaneous implantations of hydrogel discs in healthy C57BL16 mice persisted for at least 2 months and were observed as amorphous eosinophilic polarizable material beneath the muscle layer (FIG. 13). The observed birefringency under polarized optical microscopy suggests that the peptide fibers are aligned, even in the absence of external stimuli such as magnetic or electric fields. While similar observations have been made for other self-assembling peptide amphiphiles (Wall, B. D. et al. Adv Mater 23, 5009-5014, 2011; Zhang, S. et al. Nat Mater 9, 594-601, 2010), our ultrashort peptides are significantly cheaper and easier to synthesize.

Notably, the immune response to the implants was minimal to mild, and attributed to the implantation surgery since similar inflammatory responses were observed for the sham-operated mice. A few multi-nucleated giant cell histiocytes were observed in the vicinity of several implants (FIG. 13). The bulk of the hydrogel did not elicit severe immune activation and there was no capsule formation even after 2 months. There was also no observable difference in erythrocyte or leukocyte counts between animals implanted with peptide hydrogels and control animals. Analysis of serum enzyme and metabolite concentrations further suggested that the peptides did not compromise liver function. The excellent biocompatibility of Ac-LIVAGK-NH$_2$ was affirmed by the Kligman maximization assay performed on guinea pigs. Topical applications and intradermal injections of Ac-LIVAGK-NH$_2$ (SEQ ID NO: 20) elicited no irritation or allergic reactions after 24 hours, and no reactions were observed following subsequent immune challenge 27 days later (Table 1). The animals did not exhibit any systemic signs of toxicity. Concurrent genotoxicity assays proved that Ac-LIVAGK-NH$_2$ (SEQ ID NO: 20) was non-mutagenic (Table 2). In summary, our ultrashort peptides are biocompatible in vitro and in vivo, which makes them highly suitable for applications as bioinks, cell culture substrates and implantable scaffolds.

TABLE 1

The Kligman maximisation assay proved that Ac-LIVAGK-NH$_2$ was biocompatible in vivo and did not elicit any adverse immunologic or physiological events in guinea pigs. Topical applications and intradermal injections of Ac-LIVAGK-NH$_2$ and saline did not cause any sensitization or immune reactions, even with a subsequent challenge after 27 days. No visible change was observed for animals treated with peptide and saline control. All the animals treated with dinitrochlorobenzene (DNCB) demonstrated patch (graded 1) to moderate (graded 2) erythema, giving a score of 100% sensitization.

| Treatment | Animal ID | Gender | Score Day 25 | Day 26 | Day 27 | Percent animals sensitized | Allergenic potential |
|---|---|---|---|---|---|---|---|
| 8.35 mg/mL Ac-LIVAGK-NH$_2$ | 1 | Male | 0 | 0 | 0 | 0% | Weak |
| | 2 | Male | 0 | 0 | 0 | | |
| | 3 | Male | 0 | 0 | 0 | | |
| | 4 | Male | 0 | 0 | 0 | | |
| | 5 | Male | 0 | 0 | 0 | | |
| | 6 | Female | 0 | 0 | 0 | | |
| | 7 | Female | 0 | 0 | 0 | | |
| | 8 | Female | 0 | 0 | 0 | | |
| | 9 | Female | 0 | 0 | 0 | | |
| | 10 | Female | 0 | 0 | 0 | | |
| Saline (negative control) | 11 | Male | 0 | 0 | 0 | 0% | Weak |
| | 12 | Male | 0 | 0 | 0 | | |
| | 13 | Male | 0 | 0 | 0 | | |
| | 14 | Female | 0 | 0 | 0 | | |
| | 15 | Female | 0 | 0 | 0 | | |
| Dinitrochlorobenzene (positive control) | 16 | Male | 2 | 2 | 1 | 100% | Extreme |
| | 17 | Male | 2 | 2 | 1 | | |
| | 18 | Female | 1 | 1 | 0 | | |
| | 19 | Female | 2 | 1 | 1 | | |
| | 20 | Female | 1 | 0 | 0 | | |

TABLE 2

The amidated peptides, as exemplified by Ac-LIVAGK-NH$_2$, are non-mutagenic. The chromosomal aberration assay was carried out using Chinese hamster ovary cells in the (a) absence and (b) presence of metabolic activators. The different types aberrations evaluated include chromatid gap (TG), chromosome gap (SG), chromatid break (TB), chromosome break (SB), deletion (D), triradial rearrangement (TR), quadradial rearrangement (QR), complex rearrangement (CR), ring rearrangement (R), dicentric chromosome (DC), double minute (DM), and pulverized (PV). Some cells contain more than one type of aberration.

| Treatment | Number of cells analysed | Gaps TG | SG | Breaks TB | SB | D | Inter Chromosomal Rearrangements TR | QR | CR | R | DC | Other aberrations DM | PV | Cells with aberrations (excluding gaps) |
|---|---|---|---|---|---|---|---|---|---|---|---|---|---|---|
| a. | | | | | | | | | | | | | | |
| 8.35 mg/mL Ac-LIVAGK-NH$_2$ | 200 | 3 | 2 | 3 | 2 | 0 | 0 | 0 | 0 | 0 | 0 | 0 | 0 | 5 |
| 0.075 µg/mL Mitomycin C (positive control) | 100 | 3 | 1 | 17 | 9 | 1 | 0 | 4 | 0 | 0 | 0 | 4 | 0 | 26 |
| Culture media (negative control) | 200 | 2 | 0 | 0 | 1 | 0 | 0 | 0 | 0 | 0 | 0 | 0 | 0 | 1 |
| b. | | | | | | | | | | | | | | |
| 8.35 mg/mL Ac-LIVAGK-NH$_2$ | 200 | 6 | 1 | 11 | 0 | 0 | 0 | 0 | 0 | 0 | 0 | 0 | 0 | 9 |
| 0.075 µg/mL Mitomycin C (positive control) | 100 | 3 | 0 | 33 | 7 | 2 | 10 | 2 | 2 | 0 | 0 | 0 | 0 | 30 |

TABLE 2-continued

The amidated peptides, as exemplified by Ac-LIVAGK-NH$_2$, are non-mutagenic. The chromosomal aberration assay was carried out using Chinese hamster ovary cells in the (a) absence and (b) presence of metabolic activators. The different types aberrations evaluated include chromatid gap (TG), chromosome gap (SG), chromatid break (TB), chromosome break (SB), deletion (D), triradial rearrangement (TR), quadradial rearrangement (QR), complex rearrangement (CR), ring rearrangement (R), dicentric chromosome (DC), double minute (DM), and pulverized (PV). Some cells contain more than one type of aberration.

| Treatment | Number of cells analysed | Gaps | | Breaks | | | Inter Chromosomal Rearrangements | | | | | Other aberrations | | Cells with aberrations (excluding gaps) |
|---|---|---|---|---|---|---|---|---|---|---|---|---|---|---|
| | | TG | SG | TB | SB | D | TR | QR | CR | R | DC | DM | PV | |
| Culture media (negative control) | 200 | 6 | 0 | 5 | 0 | 0 | 0 | 0 | 0 | 0 | 0 | 0 | 0 | 5 |

2.3 Injectable Scaffolds

By virtue of their self-assembling properties, stimuli-responsive ultrashort peptides are ideal candidates for injectable scaffolds. Such scaffolds can be injected as semi-viscous solutions that complete assembly in situ. Irregular-shaped defects can be fully filled, facilitating scaffold integration with native tissue. These injectable formulations offer significant advantages over ex vivo techniques of preparing nanofibrous scaffolds, such as electrospinning, which have to be surgically implanted. During the process of in situ gelation, the ability to modulate gelation rate would enable the clinician to sculpt the hydrogel construct into the desired shape for applications such as dermal fillers. Furthermore, the biocompatibility and in vivo stability bodes well for implants that need to persist for several months. Taking into consideration the stiffness and tunable mechanical properties, we are particularly interested in developing injectable therapies and implantable scaffolds that fulfill mechanically supportive roles. In comparison, other peptide hydrogels, based on self-assembling α-helices, β-hairpins (G'≤2 kPa) and β-sheets (G'≤2 kPa), cannot attain such high rigidity.

We chose to formulate a minimally invasive treatment for early stage degenerative disc disease. This chronic disease afflicts 85% of the population over the age of 50 and is attributed to the progressive structural and functional degeneration of the lumbar intervertebral disc (O'Halloran, D. M. & Pandit, A. S. Tissue Eng 13, 1927-1954, 2007). Age-related changes in the nucleus pulposus (NP) ECM (FIG. 14a) affects disc stability, leading to severe lower back pain and numbness in the lower limbs when the spinal nerve is pinched by the flanking vertebrae. There are no interventional treatments and current treatment options often require surgical intervention in the form of spinal fusions or disc replacements with a metal or ceramic implant (Lewis, G. J Biomed Mater Res B Appl Biomater 100, 1702-1720, 2012). An ideal interventional remedy should be minimally invasive, biocompatible and yet be able to provide interim mechanical support for the degenerated disc to retard disease progression.

The mechanical properties and gelation kinetics were the main considerations in selecting the appropriate peptide candidate. The mechanical properties of the hydrogel can be modulated to mimic that of native tissue by varying the peptide sequence, concentration, counter-ion and salt concentration of the solution. The storage moduli of Ac-LIVAGK-NH$_2$ (SEQ ID NO: 20) and Ac-ILVAGK-NH$_2$ (SEQ ID NO: 21) approximate that of literature reported values of 2 to 10 kPa for human NP. We had previously measured the rigidity of porcine NP to be approximately 100 Pa (Mishra, A. et al. Nano Today 6, 232-239, 2011). Nonetheless, we can reduce the peptide hydrogel rigidity to match that of the large animal model, if necessary. Other injectable therapies currently in development (O'Halloran, D. M. & Pandit, A. S. Tissue Eng 13, 1927-1954, 2007) typically employ natural and modified polymers such as alginate, collagen, gelatin and hydroxybutyl chitosan. As many of these biomaterials are derived from animal sources, they are poorly defined in terms of chemical composition, which can impact regulatory approval due to potential immunogenicity and batch-to-batch variation. Their mechanical properties are also not comparable—the storage moduli of collagen I and gelatin is less than 100 Pa (Mishra, A. et al. Nano Today 6, 232-239, 2011). A stiffer hydrogel will offer more advantages as it is better able to resist compression, and dilution effects due to mixing with the degenerated ECM. Furthermore, we anticipate that over time, the hydrogel rigidity could decline. However, this may be compensated by ECM production as the tissue recovers.

We designed an injectable therapy wherein our stimuli-responsive peptide Ac-LIVAGK-NH$_2$ (SEQ ID NO: 20) was administered as a low viscosity solution which subsequently gels in situ. This therapy was evaluated in the induced disc degeneration rabbit model. The NP of three intervertebral discs were aspirated (Ho, G., Leung, V. Y., Cheung, K. M. & Chan, D. Connect Tissue Res 49, 15-21, 2008), simulating disc degeneration. One month post-injury, the rabbits were treated with either peptide hydrogel only or hydrogel encapsulating rabbit NP cells (Table 3). 20 mg/mL of Ac-LIVAGK-NH$_2$ (SEQ ID NO: 20) dissolved in PBS was selected in view of its high rigidity upon gelation and temperature-sensitive gelation. Kept on ice, the peptide solution maintained its fluidity. The low viscosity allowed a smaller diameter (25G) gauge needle to be used, reducing the collateral damage to the surrounding annulus fibrosus. When approximately 100 µL of peptide solution was injected into a damaged NP, gelation occurred within 5 minutes, allowing the clinician to position the needle and for the fluid to completely fill the NP space. Upon retraction of the needle, there was no spillage into the surrounding tissue.

TABLE 3

Experimental set-up for treatments provided to six rabbits with induced degenerative disc disease in three lumbar discs. Two different treatments were evaluated: (1) 20 mg/mL Ac-LIVAGK-NH$_2$ peptide hydrogels, and (2) 20 mg/mL Ac-LIVAGK-NH$_2$ peptide hydrogels encapsulating donor rabbit nucleus pulposus (NP) cells. To facilitate the monitoring of the implants in this experiment, the peptide hydrogels were loaded with Gadolinium-DTPA (Gd$^{3+}$-DTPA), a T1 MRI contrast agent; while the transplanted NP cells were labeled with FITC-conjugated iron oxide nanoparticles (IODEX) for T2 weighted experiments. The treatment injected into a given disc for different animals was varied to eliminate experimental bias.

| Rabbit ID | L3/L4 | L4/L5 | L5/L6 |
|---|---|---|---|
| R245 | Peptide hydrogel | Peptide hydrogel + labeled rNP cells | Untreated |
| R328 | Untreated | Peptide hydrogel | Peptide hydrogel + labeled rNP cells |
| R331 | Peptide hydrogel + labeled rNP cells | Untreated | Peptide hydrogel |
| R332 | Peptide hydrogel | Peptide hydrogel + labeled rNP cells | Untreated |
| R333 | Untreated | Peptide hydrogel | Peptide hydrogel + labeled rNP cells |
| R334 | | Untreated | |

In view that in vivo imaging plays an increasingly significant role in monitoring tissue engineering and cellular implants, the ability to label our hydrogel constructs will enable us to infer the biodistribution of the peptides and evaluate the in vivo stability in a disease environment. Magnetic resonance imaging (MRI) is a non-invasive diagnostic commonly used to monitor disc disease progression. Conventionally, MRI relies on water content in the tissues and the signal intensity depends upon the longitudinal (T1) and transverse (T2) relaxation time of water. MR images can be enhanced using contrast agents. To facilitate monitoring of the implants in this experiment, the peptide hydrogels were loaded with Gadolinium-DTPA (Gd$^{3+}$-DTPA), a T1 MRI contrast agent which brightens the image. The transplanted NP cells were labeled with FITC-conjugated iron oxide nanoparticles (IODEX) contrastophores, which generate darker images in T2 weighted experiments (FIG. 14b).

Two months post-treatment, we euthanized the animals and harvested their vertebrae for ex vivo MRI (FIG. 14c). Healthy NP has high water content and thus gives a bright signal as visualized from the coronal T1 slices. The damaged discs treated with hydrogel appear brighter due to Gd$^{3+}$-DPTA, whereas untreated discs exhibit relatively low T1 contrast, for identical acquisition parameters. The brighter signal in hydrogel treated specimens suggests that there is no leakage of the contrast agent, and hence the retention of the hydrogel in the NP space. It also confirms that diagnostic imaging agents can be incorporated for long term monitoring of the hydrogel in patients. The concept can be extrapolated to encompass the encapsulation of bioactive moieties for cell proliferation and ECM production. Small molecule therapeutics, diagnostic agents, nucleic acids and nanoparticles can potentially be incorporated into the peptide solution. Following in situ gelation, the hydrogel would act as a reservoir for the sustained and controlled release of therapeutics that stimulate NP regeneration.

Cells such as MSC and donor NP cells can be co-adminstered to stimulate tissue regeneration. Autologous or allogenic MSC could potentially secrete factors to stimulate native cells to secrete more ECM, or differentiate into NP cells. Healthy donor NP cells could potentially repopulate the degenerated NP[33]. Due to the avascular nature of NP, it is immune-privileged and foreign tissue grafts are well-tolerated. The second experimental treatment was a cell therapy consisting of peptide hydrogel co-administered with labeled donor (rabbit) NP cells. The T2 contrast exhibited by the IODEX particles in comparison with the control discs confirms the presence of labeled cells in the treated NP (FIG. 14c). Our experiments demonstrate the potential of tracking labeled cells embedded in the hydrogels. On dissection of two discs, significant NP mass was observed for the disc treated with hydrogel incorporating cells. In comparison, an untreated damaged disc did not have any visible NP content, while the contents of a hydrogel treated disc were more fluid. This suggested that cell therapy was more efficacious in terms of promoting NP regeneration, and that the hydrogels could effectively maintain the viability of donor NP cells. Examining histology sections of treated NP, both the peptide hydrogel and cell therapy treatments were well-tolerated. No adverse cellular immune reaction was observed and histiocytes were absent. The injected peptide solution integrated with the native ECM (FIG. 14d) for all the treated discs. For damaged discs given cell therapy, faintly fluorescent cells could be observed after 2 months, implicating the survival of implanted cells.

Exploiting the salt-enhanced properties of ultrashort peptides with lysine residues, we developed an injectable treatment for degenerative disc disease that can be easily manufactured, sterilized and administered. The peptide solution can be injected as a semi-viscous fluid that would fill any defect and integrate well with host tissue. Gelation can be triggered (and completed within minutes) at body temperature or by co-injection of physiologically buffered saline. The resulting nanofibrous hydrogels are stable, bio compatible and support the growth of co-administered cells. This injectable therapy is considerably less invasive compared to the surgical alternatives available in the clinic today and can potentially be offered as an early stage interventional treatment to delay the need for surgery.

Despite the shortness of the peptide, the hydrogels possess high mechanical stiffness which will provide interim mechanical support for the degenerated disc. Furthermore, the mechanical properties can be tuned to match that of host tissue by modulating peptide sequence, concentration, and ionic environment. Considering that the storage moduli can be tuned by 3 orders of magnitude, these biomimetic hydrogels can be applied to different tissue types. We can incorporate imaging contrast agents to facilitate the monitoring of the implanted/injected constructs, as well as cells and other bioactive reagents to promote tissue regeneration. Cell attachment, proliferation and differentiation can be enhanced by conjugating or encapsulating small molecules, short peptide motifs, cytokines, growth factors and oligonucleotides. Moving forward, we can enhance the mechanical stability and incorporate bioactive properties through cross-linking (Seow, W. Y. & Hauser, C. A. Adv Healthc Mater 2, 1219-1223, 2013) and functionalization (Loo, Y., Zhang, S. & Hauser, C. A. Biotechnol Adv 30, 593-603, 2012; Wu, E. C., Zhang, S. G. & Hauser, C. A. E. Funct. Mater. 22, 456-468, 2012).

This subclass of stimuli-responsive peptides is an exciting platform technology for various biomedical applications, from matrices for drug delivery to biomimetic implants for tissue engineering, to chemically well-defined synthetic cell culture substrates for stem cells, and to peptide inks for bio-printing multi-cellular constructs for high-throughput screening, organotypic disease models and implants.

The listing or discussion of a previously published document in this specification should not necessarily be taken as an acknowledgement that the document is part of the state of the art or is common general knowledge. All documents listed are hereby incorporated herein by reference in their entirety for all purposes.

Exemplary embodiments of the invention illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A method of producing a hydrogel comprising combining in an aqueous solution or polar solution self-assembling peptides and/or peptidomimetic, that have the general formula:

$$Z_a\text{-}(X)_b\text{-}(Y)_c\text{-}Z'_d$$

wherein
Z is an N-terminal protecting group;
a is 0 or 1, optionally 1;
X is, at each occurrence, independently selected from the group consisting of aliphatic D- or L-amino acids, wherein the overall hydrophobicity decreases from N- to C-terminus;
b is an integer selected from 1, 2, 3, 4, 5, 6 or 7;
Y is selected from the group consisting of basic polar D- or L-amino acids, basic polar D- or L-amino acid derivatives;
c is 1 or 2;
Z' is a C-terminal polar head group;

d is 1; and b+c is at least 3 wherein the mixture is, dispensed through needles and print heads; and subsequently co-injected with a physiologically compatible salt solution to produce a hydrogel, wherein the peptidomimetic has a regular peptide backbone where only the basic polar D- or L-amino acids are exchanged with basic polar D- or L-amino acid derivatives.

2. The method of claim 1, wherein the aliphatic amino acids are selected from the group consisting of alanine (Ala, A), homoallylglycine, homopropargylglycine, isoleucine (Ile, I), norleucine, leucine (Leu, L), valine (Val, V) and glycine (Gly, G), and wherein all the aliphatic amino acids or a portion of the aliphatic amino acids are arranged in an order of decreasing amino acid size in the direction from N- to C-terminus, and wherein the size of the aliphatic amino acids is defined as I=L>V>A>G, and/or the aliphatic amino acids have a sequence selected from the group consisting of LIVAG (SEQ ID NO: 1), ILVAG (SEQ ID NO: 2), LIVAA (SEQ ID NO: 3), LAVAG (SEQ ID NO: 4), AIVAG (SEQ ID NO: 5), GIVAG (SEQ ID NO: 6), VIVAG (SEQ ID NO: 7), ALVAG (SEQ ID NO: 8), GLVAG (SEQ ID NO: 9), VLVAG (SEQ ID NO: 10), IVAG (SEQ ID NO: 11), LIVA (SEQ ID NO: 12), LIVG (SEQ ID NO: 13), IVA and IV.

3. The method of claim 2, wherein the aliphatic amino acids are selected from the group consisting of alanine (A), isoleucine (I), leucine (L), valine (V) and glycine (G).

4. The method of claim 3, wherein there is an A preceding the sequence at the N-terminus and/or wherein b is an integer from 1 to 7.

5. The method of claim 1, wherein the basic polar amino acids and basic polar amino acid derivatives are selected from the group consisting of ornithine (Orn), lysine (Lys, K), 2,4-diaminobutyric acid (Dab), and 2,3-diaminopropionic acid (Dap).

6. The method of claim 1, wherein c is 2 and the basic polar amino acids or basic polar amino acid derivatives are identical amino acids, or wherein c is 1 and the basic polar amino acid comprises any one of lysine, ornithine, 2,4-diaminobutyric acid (Dab) and histidine.

7. The method of claim 1, wherein:

(Y)$_c$ has a sequence selected from Lys, Orn, Dab, Cys-Lys, Cys-Orn, Cys-Dab, Cys-Dap, Lys-Lys, Lys-Orn, Lys-Dab, Lys-Dap, Ser-Lys, Ser-Orn, Ser-Dab, Ser-Dap, Orn-Lys, Orn-Orn, Orn-Dab, Orn-Dap, Dab-Lys, Dab-Orn, Dab-Dab, Dab-Dap, Dap-Lys, Dap-Orn, Dap-Dab, and Dap-Dap, and/or (X)$_b$-(Y)$_c$ has a sequence selected from the group consisting of LIVAGK (SEQ ID NO: 20), ILVAGK (SEQ ID NO. 21), AIVAGK (SEQ ID NO: 24), IVAK (SEQ ID NO: 28), IIIK (SEQ ID NO: 30), LIVAGOrn (SEQ ID NO: 31), ILVAGOrn (SEQ ID NO: 32), AIVAGOrn (SEQ ID NO: 33), LIVAGDab (SEQ ID NO: 34), ILVAGDab (SEQ ID NO: 35), AIVAGDab (SEQ ID NO: 36), LIVAGDap (SEQ ID NO: 37), ILVAGDap (SEQ ID NO: 38), AIVAGDap (SEQ ID NO: 39), IVOrn, IVDab, IVDap, IVK, VIK, VIOrn, and VIDab, and/or wherein a is 1 and said N-terminal protecting group Z has the general formula —C(O)—R, wherein R is selected from the group consisting of H, unsubstituted or substituted alkyls, and unsubstituted or substituted aryls.

8. The method of claim 7, wherein R is preferably selected from the group consisting of methyl, ethyl, propyl, isopropyl, butyl and isobutyl.

9. The method of claim 1, wherein the peptides and/or peptidomimetics undergo a conformational change during self-assembly.

10. The method of claim 1, wherein the physiologically compatible salt solution comprises phosphate buffered saline and/or has a pH of 7 to 10.

11. The method of claim 1, wherein the peptides and/or peptidomimetics exhibit stimuli-responsive gelation in the physiologically compatible salt solution at physiological conditions and/or pH above physiological pH.

12. The method of claim 1, wherein in the aqueous solution or polar solution comprises water.

13. The method of claim 1, wherein the peptide and/or peptidomimetic is present in the solution at a concentration of 0.1% to 30% (w/w) with respect to the total weight of said hydrogel.

14. The method of claim 1, further comprising subjecting the solution to gelation of the hydrogel and, prior to gelation of the hydrogel or during gelation of the hydrogel, combining the solution with cells to form a multi-cellular hydrogel.

15. The method of claim 14, wherein the cells are stem cells, or transdifferentiated progenitor cells and primary cells isolated from patient samples.

16. The method of claim 14, wherein the cells are adult stem cells, mesenchymal stem cells, progenitor stem cells, embryonic stem cells, induced pluripotent stem cells, fibroblast cells, nucleus pulposus cells, epithelial cells, hematopoietic cells or cancer cells.

17. The method of claim 14, wherein the peptides and/or peptidomimetics further comprise crosslinkers optionally short linkers, linear polymers, branched polymers, or polymers conjugated with bioactive molecules or moieties.

18. The method of claim 1, further comprising subjecting the solution to gelation conditions and adding cells to the solution before gelation or during gelation to form a multi-cellular hydrogel.

19. The method of claim 1, further comprising subjecting the solution to gelation conditions to produce the hydrogel, and adding cells to the hydrogel to form a multicellular hydrogel.

20. The method of claim 1, further comprising combining in the solution a bioactive molecule, a label, a pathogen, a quantum dot, a nanoparticle, a microparticle or a combination thereof.

21. A method of preparing continuous fibers, comprising:

(a) dissolving at least one peptide and/or peptidomimetic that have the general formula:

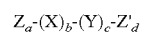

$$Z_a\text{-}(X)_b\text{-}(Y)_c\text{-}Z'_d$$

wherein

Z is an N-terminal protecting group;

a is 0 or 1, optionally 1;

X is, at each occurrence, independently selected from the group consisting of aliphatic D- or L-amino acids and aliphatic D- or L-amino acid derivatives, and wherein the overall hydrophobicity decreases from N- to C-terminus;

b is an integer selected from 1 to 7;

Y is selected from the group consisting of polar D- or L-amino acids and polar D- or L-amino acid derivatives;

c is 0, 1 or 2;

Z' is a C-terminal polar head group; and d is 1, and b+c is at least 3; wherein the peptidomimetic has a regular peptide backbone where only the basic polar D- or L-amino acids are exchanged with basic polar D- or L-amino acid derivatives and (b) dispensing the solution obtained through needles, print heads, fine tubings and/or microfluidic devices into a buffered solution to produce continuous fibers.

22. A method comprising delivering the hydrogel produced by the method of claim 1 to a subject, optionally by injecting the hydrogel into or implanting the hydrogel into the subject, wherein the hydrogel comprises a bioactive molecule.

23. A method of using a hydrogel produced by the method of claim 1 to produce 2D mini-hydrogel arrays, optionally by printing the 2D mini-hydrogels onto electrical circuits or piezoelectric surfaces that conduct current or using the hydrogel for bioprinting or biomolding.

24. The method of claim 3, wherein there is an A preceding the sequence at the N-terminus and/or wherein b is an integer from 2 to 7.

25. The method of claim 3, wherein there is an A preceding the sequence at the N-terminus and/or wherein b is an integer from 2 to 6.

26. The method of claim 1, wherein b+c is at least 3 to 9.

27. The method of claim 1, wherein b+c is at least 3 to 7.

28. The method of claim 1, wherein b+c is at least 3 to 8.

29. The method of claim 1 wherein the self-assembling peptides and/or peptidomimetic, are selected from the group consisting of:

Ac-IVK-$NH_2$; Ac-LIVAGK-$NH_2$ (SEQ ID NO: 20); Ac-ILVAGK-$NH_2$ (SEQ ID NO: 21); Ac-LIVAGOrn-$NH_2$ (SEQ ID NO: 31); Ac-ILVAGOrn-$NH_2$ (SEQ ID NO: 32); Ac-LIVAGDab-$NH_2$ (SEQ ID NO: 34); and Ac-ILVAGDab-$NH_2$ (SEQ ID NO: 35); and wherein the self-assembling peptides and/or peptidomimetic comprises less than 20 mg/ml of the total and the physiologically compatible salt solution comprises 10% volume of 9% sodium chloride or 10X phosphate-buffered saline (PBS).

* * * * *

UNITED STATES PATENT AND TRADEMARK OFFICE
CERTIFICATE OF CORRECTION

PATENT NO. : 10,179,194 B2
APPLICATION NO. : 15/039952
DATED : January 15, 2019
INVENTOR(S) : Charlotte Hauser et al.

Page 1 of 1

It is certified that error appears in the above-identified patent and that said Letters Patent is hereby corrected as shown below:

In the Claims

Column 78 Lines 27-31 should read:
16. The method of claim 14, wherein the cells are adult stem cells, mesenchymal stem cells, progenitor stem cells, embryonic stem cells, induced pluripotent stem cells, fibro-blast cells, nucleus pulposus cells, epithelial cells, hematopoietic cells or cancer cells.

Signed and Sealed this
Fourth Day of June, 2019

Andrei Iancu
*Director of the United States Patent and Trademark Office*